US011814689B2

(12) United States Patent
Wiedenheft et al.

(10) Patent No.: US 11,814,689 B2
(45) Date of Patent: Nov. 14, 2023

(54) NUCLEIC ACID DETECTION USING TYPE III CRISPR COMPLEX

(71) Applicant: Montana State University, Bozeman, MT (US)

(72) Inventors: Blake A. Wiedenheft, Bozeman, MT (US); Andrew Santiago-Frangos, Bozeman, MT (US); Anna A. Nemudraia, Bozeman, MT (US); Artem A. Nemudryi, Bozeman, MT (US)

(73) Assignee: MONTANA STATE UNIVERSITY, Bozeman, MT (US)

( * ) Notice: Subject to any disclaimer, the term of this patent is extended or adjusted under 35 U.S.C. 154(b) by 71 days.

(21) Appl. No.: 17/814,097

(22) Filed: Jul. 21, 2022

(65) Prior Publication Data

US 2023/0053573 A1 Feb. 23, 2023

Related U.S. Application Data

(60) Provisional application No. 63/320,199, filed on Mar. 15, 2022, provisional application No. 63/320,198, filed on Mar. 15, 2022, provisional application No. 63/224,356, filed on Jul. 21, 2021.

(51) Int. Cl.
| | |
|---|---|
| *C12N 9/22* | (2006.01) |
| *C12N 15/10* | (2006.01) |
| *C12Q 1/6844* | (2018.01) |
| *C12Q 1/6806* | (2018.01) |
| *C12Q 1/6876* | (2018.01) |
| *C12Q 1/70* | (2006.01) |
| *C12Q 1/6818* | (2018.01) |
| *C12Q 1/6853* | (2018.01) |

(52) U.S. Cl.
CPC ........... *C12Q 1/701* (2013.01); *C12Q 1/6806* (2013.01); *C12Q 1/6818* (2013.01); *C12Q 1/6853* (2013.01)

(58) Field of Classification Search
CPC .. C12N 2310/20; C12N 9/22; C12N 2320/11; C12Q 1/6876; G01N 1/00
See application file for complete search history.

(56) References Cited

U.S. PATENT DOCUMENTS

| 9,115,348 B2 | 8/2015 | Haurwitz et al. |
| 9,688,971 B2 | 6/2017 | Doudna et al. |
| 10,253,365 B1 | 4/2019 | Doudna et al. |
| 10,266,886 B2 | 4/2019 | Abudayyeh et al. |
| 10,337,051 B2 | 7/2019 | Doudna et al. |
| 10,494,620 B2 | 12/2019 | Doudna et al. |
| 10,494,664 B2 | 12/2019 | Doudna et al. |
| 10,648,020 B2 | 5/2020 | Zhang et al. |
| 10,844,378 B2 | 11/2020 | Siksnys et al. |
| 11,001,829 B2 | 5/2021 | Zhang et al. |
| 11,021,740 B2 | 6/2021 | Abudayyeh et al. |
| 11,118,224 B2 | 9/2021 | Doudna et al. |
| 11,174,515 B2 | 11/2021 | Abudayyeh et al. |
| 11,180,792 B2 | 11/2021 | O'Connell et al. |
| 11,299,732 B2 | 4/2022 | Marraffini et al. |
| 2014/0186843 A1 | 7/2014 | Zhang et al. |
| 2016/0017396 A1 | 1/2016 | Cann et al. |
| 2016/0068822 A1 | 3/2016 | Zhang et al. |
| 2016/0317677 A1 | 11/2016 | Bhatia et al. |
| 2018/0112255 A1 | 4/2018 | Chen et al. |
| 2018/0142222 A1 | 5/2018 | Sternberg et al. |
| 2018/0208976 A1 | 7/2018 | Doudna et al. |
| 2018/0251787 A1 | 9/2018 | Hatoum |
| 2018/0305773 A1 | 10/2018 | Abudayyeh et al. |
| 2019/0161753 A1 | 5/2019 | Terns et al. |
| 2019/0177775 A1 | 6/2019 | Doudna et al. |
| 2019/0241954 A1 | 8/2019 | Doudna et al. |
| 2019/0256900 A1 | 8/2019 | Zhang et al. |
| 2019/0300908 A1 | 10/2019 | Doudna et al. |
| 2019/0359971 A1 | 11/2019 | Zhang et al. |
| 2019/0382800 A1 | 12/2019 | Severinov et al. |

(Continued)

FOREIGN PATENT DOCUMENTS

| CN | 110982945 A | 4/2020 |
| CN | 111996236 | 11/2020 |

(Continued)

OTHER PUBLICATIONS

Broughton et al., "CRISPR-Cas12-based detection of SARS-CoV-2", Nature Biotechnology, Jul. 2020, pp. 870-874, vol. 38.
Dao Thi et al., "A colorimetric RT-LAMP assay and LAMP-sequencing for detecting SARS-CoV-2 RNA in clinical samples", Science Translational Medicine, Aug. 12, 2020, pp. 1-13, vol. 12, eabc7075.
Elbe et al., "Data, disease and diplomacy: GISAID's innovative contribution to global health", Global Challenges, Jan. 10, 2017, pp. 33-46, vol. 1(1).
Elmore et al., "Bipartite recognition of target RNAs activates DNA cleavage by the Type III-B CRISPR-Cas system", Genes & Development, Feb. 15, 2016, pp. 447-459, vol. 30(4).

(Continued)

*Primary Examiner* — Barry A Chestnut
(74) *Attorney, Agent, or Firm* — Pillsbury Winthrop Shaw Pittman LLP

(57) ABSTRACT

The disclosure relates to engineered systems and methods for detecting target nucleic acid in a sample, which may be a complex mixture. The systems and methods may improve sensitivity of target nucleic acid detection by enhancing signal generation. For example, signal generation may be enhanced through programmable capture and concentration of the target nucleic acid using an engineered type III CRISPR complex. Various ancillary nucleases such as Can1, Can2, and NucC are identified and may be used for detection. For example, binding of the engineered type III CRISPR complex may produce products that activate the identified ancillary nucleases. Different activators trigger changes in the substrate specificity of these nucleases. The activated nucleases may be used to detect programmatic detection of the target nucleic in the sample. The systems and methods are shown to detect viral RNA directly from nasopharyngeal swab samples.

22 Claims, 28 Drawing Sheets

Specification includes a Sequence Listing.

(56) References Cited

U.S. PATENT DOCUMENTS

| | | |
|---|---|---|
| 2020/0010878 A1 | 1/2020 | Doudna et al. |
| 2020/0032324 A1 | 1/2020 | Baughman et al. |
| 2020/0080137 A1 | 3/2020 | Green et al. |
| 2020/0087642 A1 | 3/2020 | Doudna et al. |
| 2020/0165594 A1 | 5/2020 | Zhang et al. |
| 2020/0181720 A1 | 6/2020 | Omar et al. |
| 2020/0231975 A1 | 7/2020 | Gootenberg et al. |
| 2020/0248229 A1 | 8/2020 | Zhang et al. |
| 2020/0254443 A1 | 8/2020 | Zhang et al. |
| 2020/0263166 A1 | 8/2020 | Zhang et al. |
| 2020/0277600 A1 | 9/2020 | Zhang et al. |
| 2020/0332272 A1 | 10/2020 | Zhang et al. |
| 2020/0370028 A1 | 11/2020 | Doudna et al. |
| 2020/0392473 A1 | 12/2020 | Zhang et al. |
| 2020/0399697 A1 | 12/2020 | Doudna et al. |
| 2021/0017508 A1 | 1/2021 | Doudna et al. |
| 2021/0071158 A1 | 3/2021 | Zhang et al. |
| 2020/1010219 | 4/2021 | Sabeti et al. |
| 2021/0102242 A1 | 4/2021 | Chen et al. |
| 2021/0108267 A1 | 4/2021 | Zhang et al. |
| 2021/0130799 A1 | 5/2021 | Siksnys et al. |
| 2021/0147915 A1 | 5/2021 | Zhang et al. |
| 2021/0163944 A1 | 6/2021 | Zhang et al. |
| 2021/0164025 A1 | 6/2021 | Blake et al. |
| 2021/0172017 A1 | 6/2021 | Jin et al. |
| 2021/0214697 A1 | 7/2021 | Doudna et al. |
| 2021/0269858 A1 | 9/2021 | Chiu et al. |
| 2021/0269866 A1 | 9/2021 | Zhang et al. |
| 2021/0292721 A1 | 9/2021 | Zhang et al. |
| 2021/0292823 A1 | 9/2021 | Zhang et al. |
| 2021/0292824 A1 | 9/2021 | Zhang et al. |
| 2021/0309981 A1 | 10/2021 | Doudna et al. |
| 2021/0317527 A1 | 10/2021 | Doudna et al. |
| 2021/0332446 A1 | 10/2021 | Wiedenheft et al. |
| 2021/0348212 A1 | 11/2021 | Fozouni et al. |
| 2021/0348243 A1 | 11/2021 | Ott et al. |
| 2021/0355487 A1 | 11/2021 | Doudna et al. |
| 2021/0371926 A1 | 12/2021 | Zhang et al. |
| 2021/0388437 A1 | 12/2021 | Doudna et al. |
| 2022/0025463 A1 | 1/2022 | Abudayyeh et al. |

FOREIGN PATENT DOCUMENTS

| | | |
|---|---|---|
| WO | 2011/143124 A2 | 11/2011 |
| WO | 2013/082519 A2 | 6/2013 |
| WO | 2013/188638 A2 | 12/2013 |
| WO | 2014/093709 A1 | 6/2014 |
| WO | 2014/145599 A2 | 9/2014 |
| WO | 2014/204727 A1 | 12/2014 |
| WO | 2015/089277 A1 | 6/2015 |
| WO | 2016/049258 A2 | 3/2016 |
| WO | 2016/094872 A1 | 6/2016 |
| WO | 2016/100974 A1 | 6/2016 |
| WO | 2016/108926 A1 | 7/2016 |
| WO | 2016/123243 A1 | 8/2016 |
| WO | 2017/205668 A1 | 11/2017 |
| WO | 2017/219027 A1 | 12/2017 |
| WO | 2018/035388 A1 | 2/2018 |
| WO | 2018/107129 A1 | 6/2018 |
| WO | 2018/170340 A1 | 9/2018 |
| WO | 2018/191388 A1 | 10/2018 |
| WO | 2019/010422 A1 | 1/2019 |
| WO | 2019/051318 A1 | 3/2019 |
| WO | 2019/071051 A1 | 4/2019 |
| WO | 2019/089808 A1 | 5/2019 |
| WO | 2019/089820 A1 | 5/2019 |
| WO | 2019/104058 A1 | 5/2019 |
| WO | 2019/126577 A2 | 6/2019 |
| WO | 2019/148206 A1 | 8/2019 |
| WO | 2019237032 | 12/2019 |
| WO | 2020/006036 A1 | 1/2020 |
| WO | 2020/006049 A1 | 1/2020 |
| WO | 2020/006067 A1 | 1/2020 |
| WO | 2020/028180 A1 | 2/2020 |
| WO | 2020/028729 A1 | 2/2020 |
| WO | 2020/041456 A1 | 2/2020 |
| WO | 2020/046809 A1 | 3/2020 |
| WO | 2020/051452 A2 | 3/2020 |
| WO | 2020/092553 A1 | 5/2020 |
| WO | 2020/092725 | 5/2020 |
| WO | 2020/106630 A1 | 5/2020 |
| WO | 2020/169970 A1 | 5/2020 |
| WO | 2020/142739 A1 | 7/2020 |
| WO | 2020/142754 A2 | 7/2020 |
| WO | 2020/181101 A1 | 9/2020 |
| WO | 2020/186231 A2 | 9/2020 |
| WO | 2020/223634 A1 | 11/2020 |
| WO | 2020/256553 A1 | 12/2020 |
| WO | 2020/257356 A2 | 12/2020 |
| WO | 2021/016453 A1 | 1/2021 |
| WO | 2021/021532 A1 | 2/2021 |
| WO | 2021/026227 A1 | 2/2021 |
| WO | 2021/046257 A1 | 3/2021 |
| WO | 2021/055874 A1 | 3/2021 |
| WO | 2021/075555 | 4/2021 |
| WO | 2021/087203 A1 | 5/2021 |
| WO | 2021/133829 A1 | 7/2021 |
| WO | 2021133977 | 7/2021 |
| WO | 2021/159020 A2 | 8/2021 |
| WO | 2021/163584 A1 | 8/2021 |
| WO | 2021/188830 A2 | 9/2021 |
| WO | 2021/207702 A1 | 10/2021 |
| WO | 2021/216772 A1 | 10/2021 |
| WO | 2021/216868 A1 | 10/2021 |
| WO | 2021/236850 A1 | 11/2021 |
| WO | 2021/243308 A2 | 12/2021 |
| WO | 2022/006536 A1 | 1/2022 |

OTHER PUBLICATIONS

Fozouni et al., "Amplification-free detection of SARS-CoV-2 with CRISPR-Cas13a and mobile phone microscopy", Cell, Jan. 21, 2021, pp. 323-333, vol. 184.

Gootenberg et al., "Multiplexed and portable nucleic acid detection platform with Cas13, Cas12a, and Csm6", Science, Apr. 27, 2018, pp. 439-444, vol. 360.

Grubaugh et al., "An amplicon-based sequencing framework for accurately measuring intrahost virus diversity using PrimalSeq and iVar", Genome Biology, 2019, pp. 1-19, vol. 20(8).

Joung et al., "Detection of SARS-CoV-2 with SHERLOCK One-Pot Testing", The New England Journal of Medicine, Sep. 16, 2020, pp. 1492-1495, vol. 353.

Lascola et al., "Viral RNA load as determined by cell culture as a management tool for discharge of SARS-CoV-2 patients from infectious disease wards", European Journal of Clinical Microbiology & Infectious Diseases, 2020, pp. 1059-1061, vol. 39.

Lazer et al., "The State of the Nation: A 50-State COVID-19 Survey Report #8: Failing the Test: Waiting Times for COVID Diagnostic Tests Across the U.S.", The COVID-19 Consortium for Understanding the Public's Policy Preferences Across States, Aug. 3, 2020, pp. 1-7.

Liu et al., "Target preference of Type III-A CRISPR-Cas complexes at the transcription bubble", Nature Communications, 2019, pp. 1-13.

Nasef et al., "Regulation of cyclic oligoadenylate synthesis by the *Staphylococcus epidermidis* Cas10-Csm complex", RNA, 2019, pp. 948-962, vol. 25(8).

Nemudryi et al., "SARS-CoV-2 genomic surveillance identifies naturally occurring truncations of ORF7a that limit immune suppression", medRxiv preprint, Mar. 10, 2021, pp. 1-11.

Notomi et al., "Loop-mediated isothermal amplification of DNA", Nucleic Acids Research, 2000, pp. 1-7, vol. 28(12), e63.

Paltiel et al., "Assessment of SARS-CoV-2 Screening Strategies to Permit the Safe Reopening of College Campuses in the United States", JAMA Network Open, Jul. 31, 2020, pp. 1-12, vol. 3(7):e2016818.

Rambaut et al., "A dynamic nomenclature proposal for SARS-CoV-2 lineages to assist genomic epidemiology", Nature Microbiology, Nov. 2020, pp. 1403-0407, vol. 5.

(56) References Cited

OTHER PUBLICATIONS

Rolando et al., "Real-time kinetics and high-resolution melt curves in single-molecule digital LAMP to differentiate and study specific and non-specific amplification", Nucleic Acids Research, Feb. 27, 2020, pp. 1-21, vol. 48(7), e42.
Samai et al., "Co-transcriptional DNA and RNA Cleavage during Type III CRISPR-Cas Immunity", Cell Press, May 21, 2015, pp. 1164-1174, vol. 161.
Sofos et al., "Structures of the Cmr-b Complex Reveal the Regulation of the Immunity Mechanism of Type III-B CRISPR-Cas", Molecular Cell, Sep. 3, 2020, pp. 741-757, vol. 79.
Staals et al., "RNA Targeting by the Type III-A CRISPR-Cas Csm Complex of Thermus thermophilus", Molecular Cell, Nov. 20, 2014, pp. 518-530, vol. 56.
Tamulaitis et al., "Programmable RNA Shredding by the Type III-A CRISPR-Cas System of *Streptococcus thermophilus*", Molecular Cell, Nov. 20, 2014, pp. 506-517, vol. 56.
Tomita et al., "Loop-mediated isothermal amplification (LAMP) of gene sequences and simple visual detection of products", Nature Protocols, Apr. 24, 2008, pp. 877-882, vol. 3(5).
Tyson et al., "Improvements to the ARTIC multiplex PCR method for SARS-CoV-2 genome sequencing using nanopore", bioRxiv, Sep. 4, 2020, pp. 1-19.
Wolfel et al., "Virological assessment of hospitalized patients with COVID-2019", Nature, May 28, 2020, pp. 465-469, vol. 581.
Yan et al., "Functionally diverse type V CRISPR-Cas systems", Science, Jan. 4, 2019, pp. 88-91, vol. 363.
Zhang, Yinhua et al., "Enhancing colorimetric loop-mediated isothermal amplification speed and sensitivity with guanidine chloride", BioTechniques, Jul. 8, 2020, pp. 179-185, vol. 69.
Zhang, Jing et al., "Multiple nucleic acid cleavage modes in divergent type III CRISPR systems", Nucleic Acids Research, Jan. 21, 2016, pp. 1789-1799, vol. 44(4).
Patent Cooperation Treaty, International Search Report and Written Opinion issued in corresponding International Application No. PCT/US2021/029219, dated Oct. 27, 2021.
Tomita, N et al., Loop-Medicated Isothermal Amplification (LAMP) of Gene Sequences and Simple Visual Detection of Products, Nature Protocols, 2008.
Fischbach, J et al., Alizarin Red S for Online Pyrophosphate Detection Identified by a Rapid Screening Method, Scientific Reports, Mar. 2017.
Abbott, TR et al., Development of CRISPR as a Prophylactic Strategy To Combat Novel Coronavirus and Influenza, bioRxIv, Mar. 2020.
East-Seletsky, A et al., Two Distinct RNase Activities of CRISPR-C2c2 Enable Guide RNA Processing and RNA Detection, Nature, Oct. 2016.
Patent Cooperation Treaty, Preliminary Report on Patentability issued in PCT/US2021/029219, dated Nov. 10, 2022, pp. 1-15.
International Search Report and Written Opinion issued in corresponding International Application No. PCT/US2022/73538, dated Oct. 27, 2022.
Sarari F. et al., CRISPR systems: Novel approaches for detection and combating COVID-19, Jan. 8, 2021, p. 7, col. 2, paragraph 2, vol. 294.
Abudayyeh et al., "New CRISPR enzyme activities add to the nucleic acid detection arsenal", Science, May 28, 2021, pp. 914-915, vol. 372 (6545).
Allan-Blitz et al.,"A Real-World Comparison of SARS-CoV-2 Rapid Antigen Testing versus PCR Testing in Florida", Journal of Clinical Microbiology, Oct. 2021, vol. 59(10).
Athukoralage et al.,"The dynamic interplay of host and viral enzymes in type III CRISPR-mediated cyclic nucleotide signalling", Biochemistry and Chemical Biology, Apr. 27, 2020, pp. 1-16.
Athukoralage et al.,"A Type III CRISPR Ancillary Ribonuclease Degrades Its Cyclic Oligoadenylate Activator", Journal of Molecular Biology, Jul. 12, 2019, pp. 2894-2899, vol. 431(15).
Athukoralage et al.,"Ring nucleases deactivate type III CRISPR ribonucleases by degrading cyclic oligoadenylate", Nature, Oct. 11, 2018, pp. 277-280, vol. 562(7726).
Bailey et al., "Fitting a mixture model by expectation maximization to discover motifs in biopolymers", Proceedings International Conference on Intelligent Systems for Molecular Biology, 1994, pp. 28-36.
Batejat et al., "Heat inactivation of the severe acute respiratory syndrome coronavirus 2", Journal of Biosafety and Biosecurity, 2021, pp. 1-3, vol. 3.
Capella-Gutierrez et al., "trimAI: a tool for automated alignment trimming in large-scale phylogenetic analyses", Bioinformatics, Jun. 8, 2009, pp. 1972-1973, vol. 25(15).
Chen et al., "CRISPR-Cas12a target binding unleashes indiscriminate single-stranded DNase activity", Science, Apr. 27, 2018, pp. 436-439, vol. 360.
Darriba et al., "ProtTest 3: fast selection of best-fit models of protein evolution", Bioinformatics, Feb. 17, 2011, pp. 1164-1165, vol. 27(8).
Drain et al., "Rapid Diagnostic Testing for SARS-CoV-2", The New England Journal of Medicine, Jan. 7, 2022, pp. 264-272, vol. 386.
East-Seletsky et al., "Two distinct RNase activities of CRISPR-C2c2 enable guide-RNA processing and RNA detection", Nature, Oct. 13, 2016, pp. 270-289, vol. 538.
Finn et al., "HMMER web server: interactive sequence similarity searching", Nucleic Acids Research, May 18, 2011, pp. W29-W37, vol. 39.
Foster et al., "Regulation of the RNA and DNA nuclease activities required for Pyrococcus furiosus Type III-B CRISPR-Cas immunity", Nucleic Acids Research, Mar. 21, 2020, pp. 4418-4434, vol. 48(8).
Garcia-Doval et al., "Activation and self-inactivation mechanisms of the cyclic oligoadenylate-dependent CRISPR ribonuclease Csm6", Nature Communications, 2020, pp. 1-9, vol. 11(1596).
Gootenberg et al., "Nucleic acid detection with CRISPR-Cas13a/C2c2", Science, Apr. 28, 2017, pp. 438-442, vol. 356.
Gouveia-Oliveira et al., "MaxAlign: maximizing usable data in an alignment", BMC Bioinformatics, Aug. 28, 2007, pp. 1-8, vol. 8(312.
Gruschow et al., "Specificity and sensitivity of an RNA targeting type III CRISPR complex coupled with a NucC endonuclease effector", Nucleic Acids Research, Dec. 6, 2021, pp. 13122-13134, vol. 49(22).
Hale et al., "RNA-Guided RNA Cleavage by a CRISPR RNA-Cas Protein Complex", Cell, Nov. 25, 2009, pp. 945-956, vol. 139.
Jain et al., "Nanopore sequencing and assembly of a human genome with ultra-long reads", Nature Biotechnology, Jan. 29, 2018, pp. 338-353, vol. 36(4).
Jia et al., "Second Messenger cA4 Formation within the Composite Csm1 Palm Pocket of Type III-A CRISPRCas Csm Complex and Its Release Path", Molecular Cell, Sep. 5, 2019, pp. 933-943, vol. 75.
Jia et al., "CRISPR-Cas III-A Csm6 CARF Domain Is a Ring Nuclease Triggering Stepwise cA4 Cleavage with ApA>p Formation Terminating RNase Activity", Molecular Cell, Sep. 5, 2019, pp. 944-956, vol. 75.
Jiang et al., "Degradation of Phage Transcripts by CRISPR Associated RNases Enables Type III CRISPR-Cas Immunity", Cell, Feb. 11, 2016, pp. 710-721, vol. 164.
Jiao et al., "Noncanonical crRNAs derived from host transcripts enable multiplexable RNA detection by Cas9", Science, May 28, 2021, pp. 941-948, vol. 372.
Kaminski et al., "CRISPR-based diagnostics", Nature Biomedical Engineering, Jul. 2021, pp. 643-656, vol. 5.
Katoh et al., "MAFFT Multiple Sequence Alignment Software Version 7: Improvements in Performance and Usability", Molecular Biology and Evolution, Jan. 16, 2013, pp. 772-780, vol. 30(4).
Kazlauskiene et al., "Spatiotemporal Control of Type III-A CRISPR-Cas Immunity: Coupling DNA Degradation with the Target RNA Recognition", Molecular Cell, Apr. 21, 2016, pp. 295-306, vol. 62.
Kazlauskiene et al., "A cyclic oligonucleotide signaling pathway in type III CRISPR-Cas systems", Science, Aug. 11, 2017, pp. 605-609, vol. 357.

(56) References Cited

OTHER PUBLICATIONS

Larremore et al., "Test sensitivity is secondary to frequency and turnaround time for COVID-19 screening", Science Advances, Jan. 1, 2021, pp. 1-10, vol. 7.
Lau et al., "Structure and Mechanism of a Cyclic Trinucleotide-Activated Bacterial Endonuclease Mediating Bacteriophage Immunity", Molecular Cell, Feb. 20, 2020, pp. 723-733, vol. 77.
Lee et al., "CRISPR-Cap: multiplexed double-stranded DNA enrichment based on the CRISPR system", Nucleic Acids Research, Sep. 12, 2018, pp. 1-13, vol. 47(1).
Li et al., "Cd-hit: a fast program for clustering and comparing large sets of protein or nucleotide sequences", Bioinformatics, May 26, 2006, pp. 1658-1659, vol. 22(13).
Liu et al., "The Molecular Architecture for RNA-Guided RNA Cleavage by Cas13a", Cell, Aug. 10, 2017, pp. 714-726, vol. 170.
Liu et al., "Accelerated RNA detection using tandem CRISPR nucleases", Nature Chemical Biology, Sep. 2021, pp. 982-988, vol. 17(982).
Liu et al., "RNA and DNA Targeting by a Reconstituted Thermus thermophilus Type III-A CRISPR-Cas System", PLOS ONE, Jan. 23, 2017, pp. 1-20.
Lowey et al., "CBASS Immunity Uses CARF-Related Effectors to Sense 30-50- and 20-50-Linked Cyclic Oligonucleotide Signals and Protect Bacteria from Phage Infection", Cell, Jul. 9, 2020, pp. 38-49, vol. 182.
Makarova et al., "Evolutionary and functional classification of the CARF domain superfamily, key sensors in prokaryotic antivirus defense", Nucleic Acids Research, Jul. 31, 2020, pp. 8828-8847, vol. 48(16).
Mcmahon et al., "Structure and mechanism of a Type III CRISPR defence DNA nuclease activated by cyclic oligoadenylate", Nature Communications, Jan. 24, 2020, pp. 1-11, vol. 11(1):500.
Minh et al., "IQ-TREE 2: New Models and Efficient Methods for Phylogenetic Inference in the Genomic Era", Molecular Biology and Evolution, Feb. 3, 2020, pp. 1530-1534, vol. 37(5).
Molina et al., "Structure of Csx1-cOA4 complex reveals the basis of RNA decay in Type III-B CRISPR-Cas", Nature Communications, Sep. 20, 2019, pp. 1-14, vol. 10(1):430.
Niewoehner et al., "Type III CRISPR-Cas systems produce cyclic oligoadenylate second messengers", Nature, Aug. 31, 2017, pp. 543-548, vol. 548(7669).
Oconnell et al., "Programmable RNA recognition and cleavage by CRISPR/Cas9", Molecular Cell, Feb. 15, 2018, pp. 906-914, vol. 69(5).
Pardee et al., "Rapid, Low-Cost Detection of Zika Virus Using Programmable Biomolecular Components", Cell, May 19, 2016, pp. 1255-1266, vol. 165.
Price et al., "FastTree 2—Approximately Maximum-Likelihood Trees for Large Alignments", PLoS ONE, Mar. 2010, pp. 1-10, vol. 5(3).
Prince-Guerra et al., "Evaluation of Abbott BinaxNOW Rapid Antigen Test for SARS-CoV-2 Infection at Two Community-Based Testing Sites—Pima County, Arizona, Nov. 3-17, 2020", Morbidity and Mortality Weekly Report, Jan. 19, 2021, pp. 100-105, vol. 70(3).
Rostol et al., "The Card1 nuclease provides defence during type III CRISPR immunity", Nature, Feb. 25, 2021, pp. 624-649, vol. 590.
Rostol et al., "Non-specific degradation of transcripts promotes plasmid clearance during type III-A CRISPR-Cas immunity", Nature Microbiology, Apr. 2019, pp. 656-662, vol. 4.
Rouillon et al., "Control of cyclic oligoadenylate synthesis in a type III CRISPR system", eLife 7:e36734, Jul. 2, 2018, pp. 1-22.
Santiago-Frangos et al., "Intrinsic signal amplification by type III CRISPR-Cas systems provides a sequence-specific SARS-CoV-2 diagnostic", Cell Reports Medicine, Jun. 15, 2021, pp. 1-14, vol. 2.
Schultzhause et al., "CRISPR-based enrichment strategies for targeted sequencing", Biotechnology Advances, Nov. 28, 2020, pp. 1-15, vol. 46(107672).
Smalakyte et al., "Type III-A CRISPR-associated protein Csm6 degrades cyclic hexa-adenylate activator using both CARF and HEPN domains", Nucleic Acids Research, 2020, pp. 9204-9217, vol. 45(16).
Sridhara et al., "Virus detection via programmable Type III-A CRISPR-Cas systems", Nature Communications, 2021, pp. 1-10, vol. 12(5653).
Steens et al., "SCOPE enables type III CRISPR-Cas diagnostics using flexible targeting and stringent CARF ribonuclease activation", Nature Communications, 2021, pp. 1-12, vol. 12(5033).
Ye et al., "HORMA Domain Proteins and a Trip13-like ATPase Regulate Bacterial cGAS-like Enzymes to Mediate Bacteriophage Immunity", Molecular Cell, Feb. 20, 2020, pp. 709-722.
Yu et al., "Two Methods for Mapping and Visualizing Associated Data on Phylogeny Using Ggtree", Mol. Biol. Evol., Oct. 23, 2018, pp. 3041-3043, vol. 35(12).
Zhu et al., "The CRISPR ancillary effector Can2 is a dual-specificity nuclease potentiating type III CRISPR defence", Nucleic Acids Research, Feb. 15, 2021, pp. 2777-2789, vol. 49(5.).
International Search Report and Written Opinion issued in corresponding International Application No. PCT/US2022/074017; dated Dec. 19, 2022.
Athukoralage et al. "Cyclic Oligoadenylate Signaling and Regulation by Ring Nucleases During Type III CRISPR Defense." May 13, 2021, vol. 27(8), pp. 855-867. Retrieved from interneton Oct. 10, 2022 <URL: https://majournal.cship.org/content/27/8/855>.
Santiago-Frangos et al. Intrinsic signal amplification by type III CRISPR-Cas systems provides a sequence-specific SARS-CoV-2 diagnostic. Cell Rep Med, May 27, 2021, vol. 2:100319, pp. 1-8, e1-e5, doi: 10.1016/J.xcrm.2021.100319 entire document.
Lauer el ai. Development and Characterization of Ni-NTa-Bearing Microspheres, Cytometry, 2002, vol. 48, pp. 136-145. entire document.
Nemudraia et al. Sequence-specific capture and concentration of viral RNA by type III CRISPR system enhances diagnostic. Res Square, Apr. 19, 2022, pp. 1-33, doi: 10.21203/rs.3.rs-1466718/v1, [retrieved on 17.11.2022]. Retrieved from the internet: <URL: hitps://www.scienceoperi.com/document_flle/999d3857-d444-4e82-8864-4fc6be 7 e9e11 /PubMe dCentral/999d3857-d444-4e82-8864-4fc6be7e9e? 1.pdf>. entire document.
Zhu et al. The CRISPR ancillary effector Can2 is a dual-specificity nuclease potentiating type III CRISPR defence Nucleic Acids Res. Feb. 15, 2021; vol. 49(5), pp. 2777-2789. doi: 10.1093/nar/gkab073 entire document.
United States Patent and Trademark Office, Official Action dated 17/814,674, dated Apr. 3, 2023, pp. 1-31.
Wang, "One-pot Detection of COVID-19 with Real-time Reverse-transcription Loop-mediated Isothermal Amplification (RT-LAMP) Assay and Visual RT-LAMP Assay," at bioRxiv, Apr. 22, 2020, pp. 1-7.
Tucker et al., "Colorimetric Determination of pH," Journal of Chemical Education, 1989, pp. 1-3, vol. 66(9).

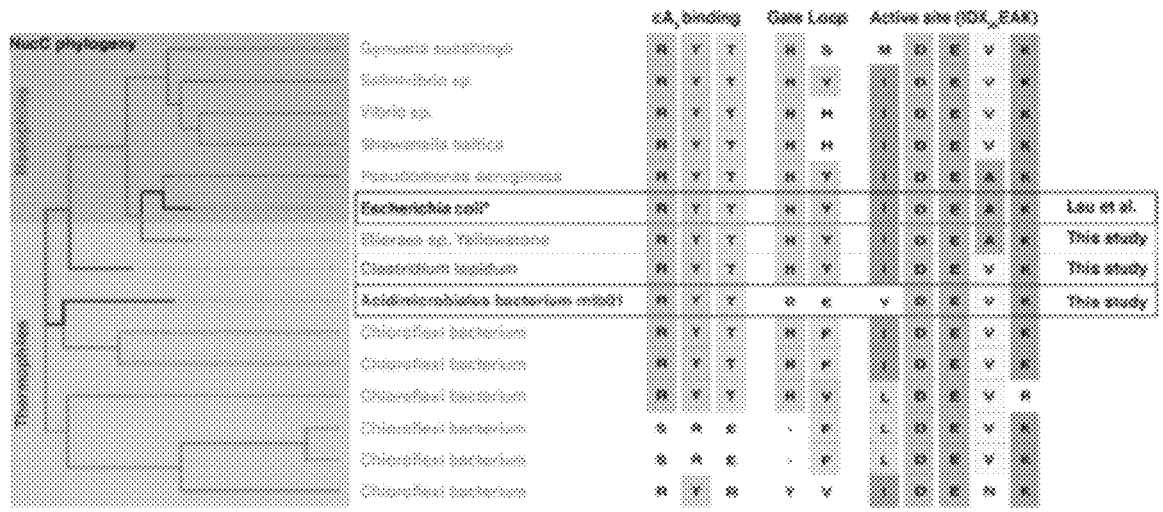
FIG. 2A
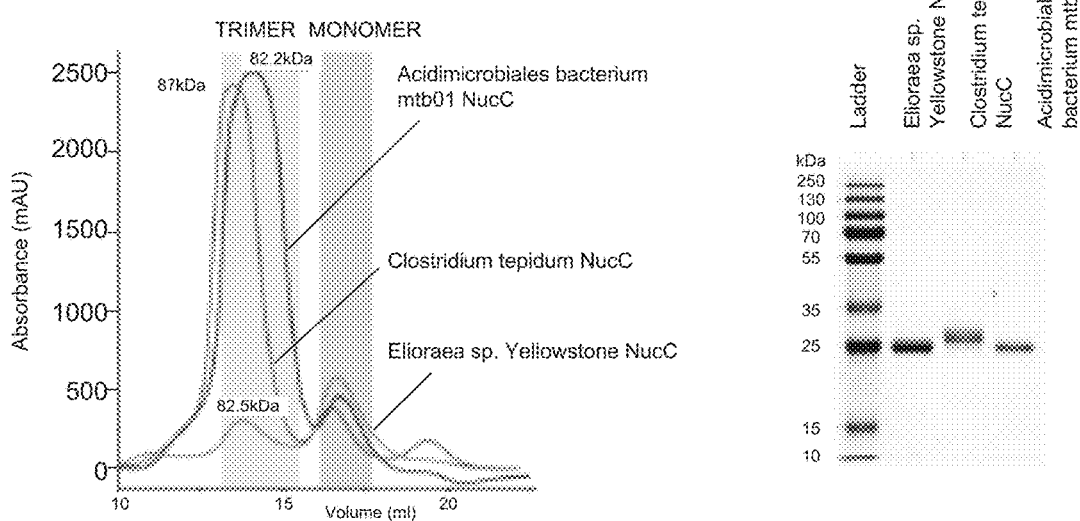
FIG. 2B
FIG. 2C

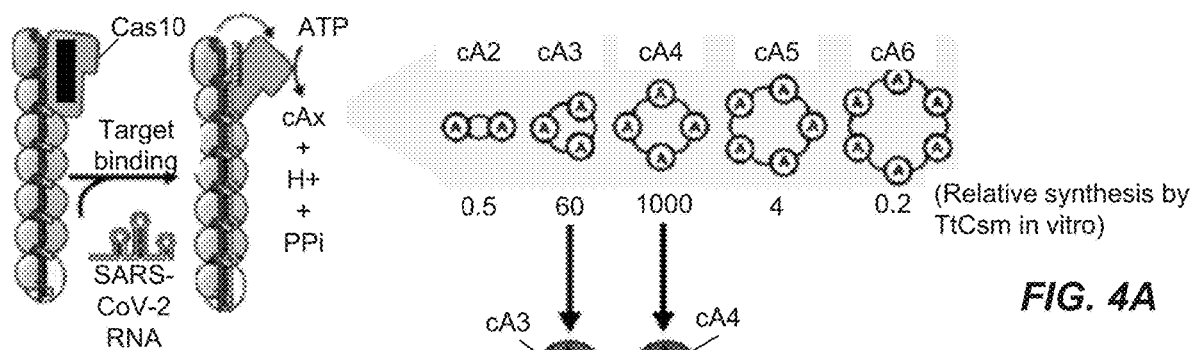
FIG. 4A
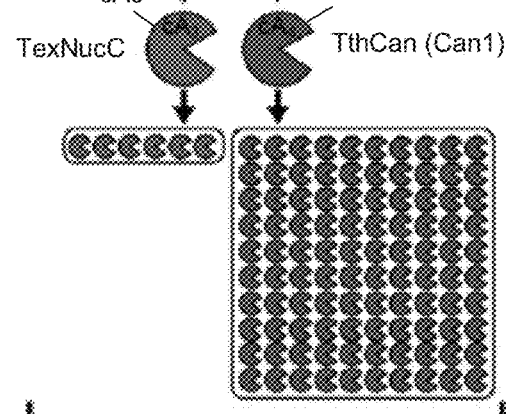
FIG. 4B
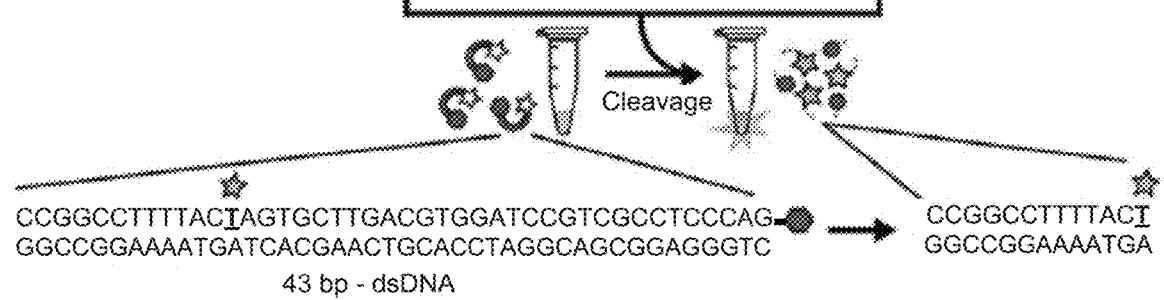
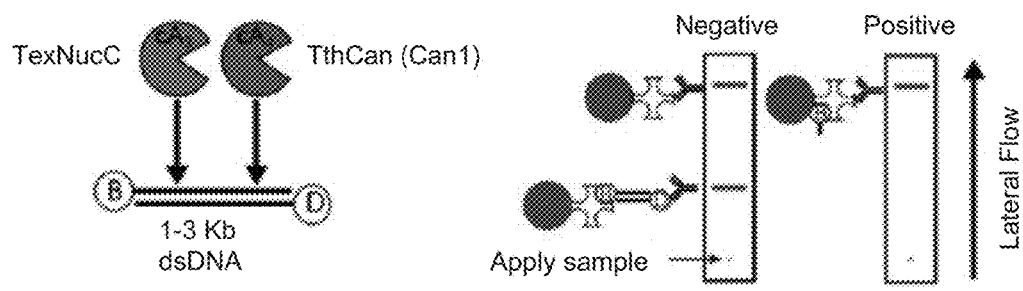
FIG. 4C

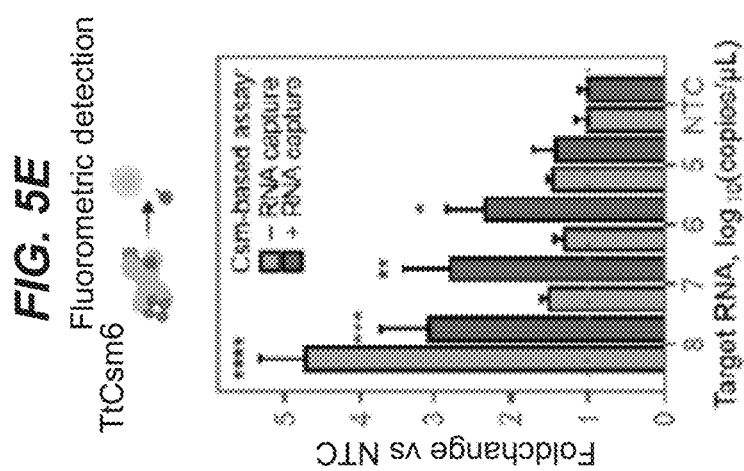
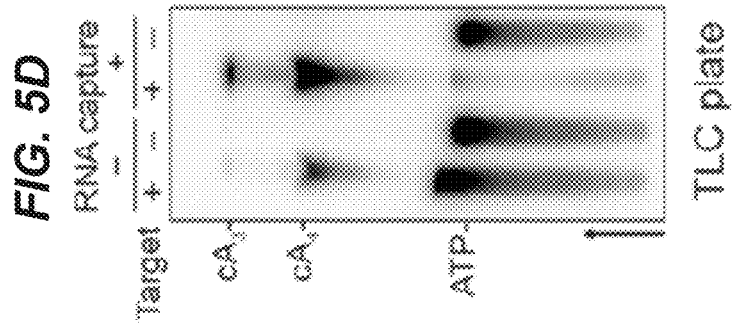
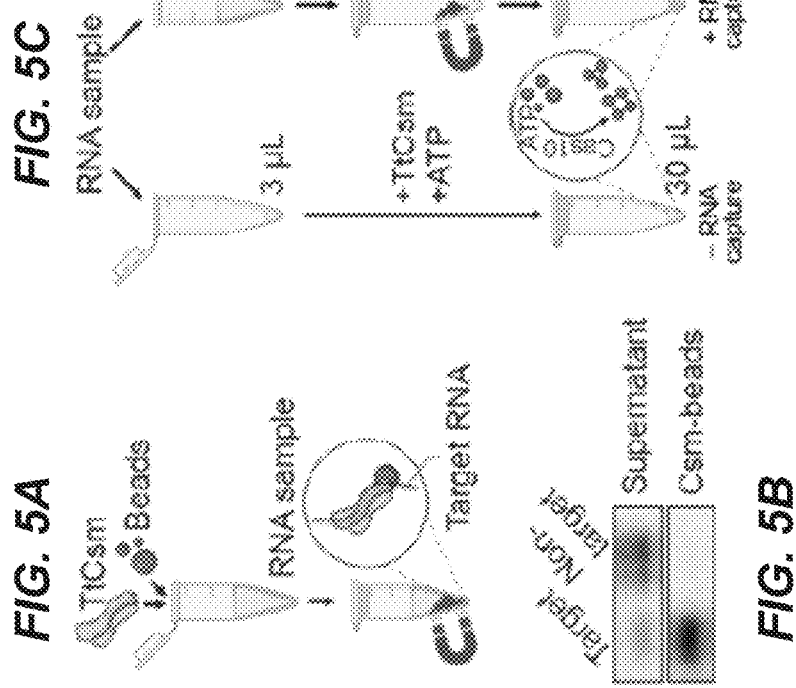

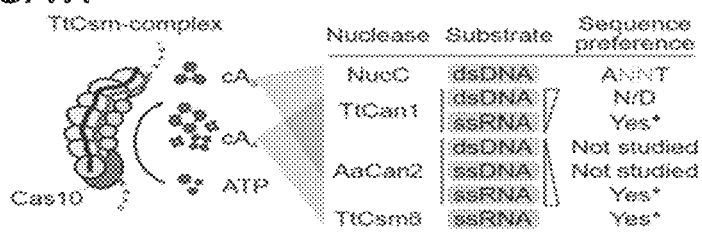
*FIG. 7A*
*FIG. 7B*
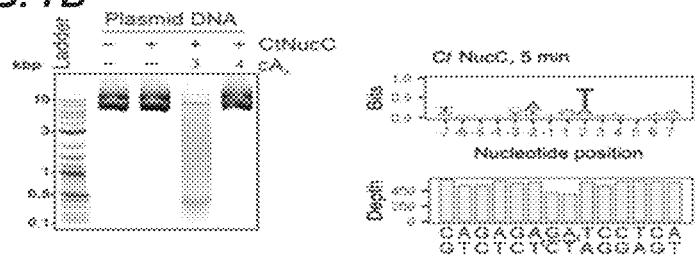
*FIG. 7C*
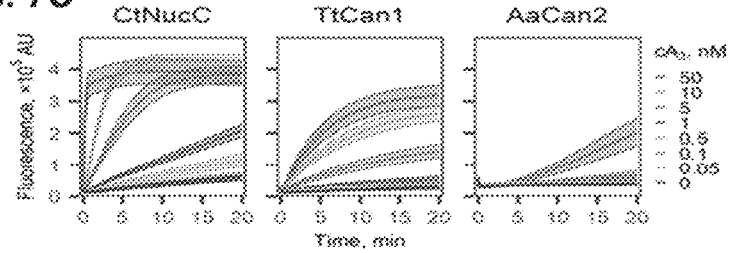
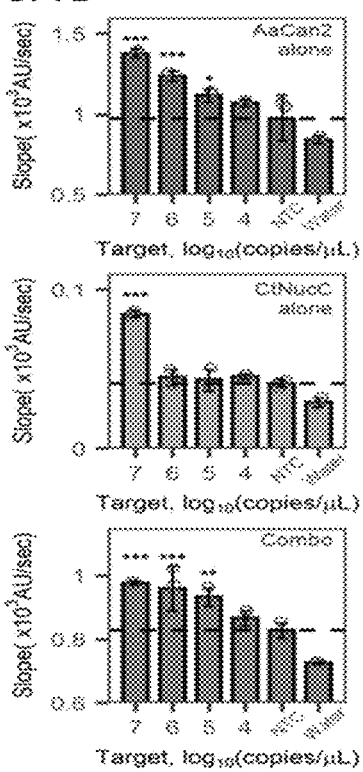
*FIG. 7D*
*FIG. 7*

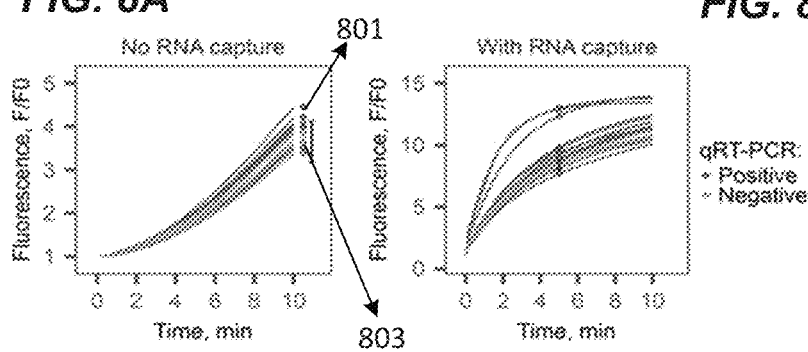
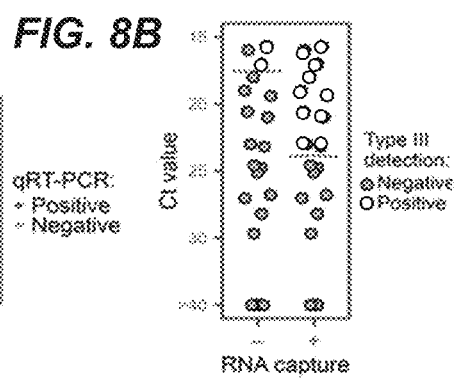
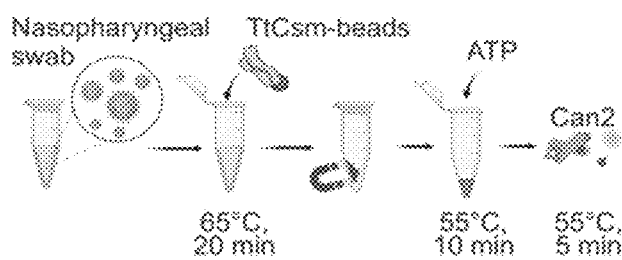
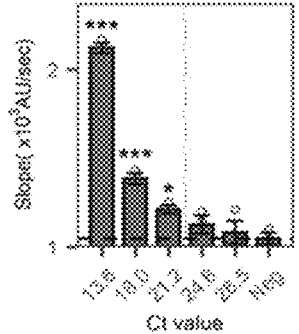

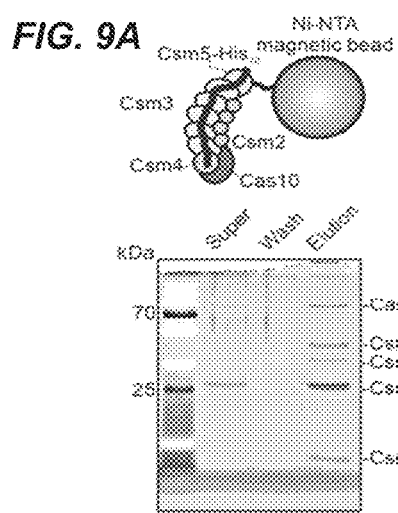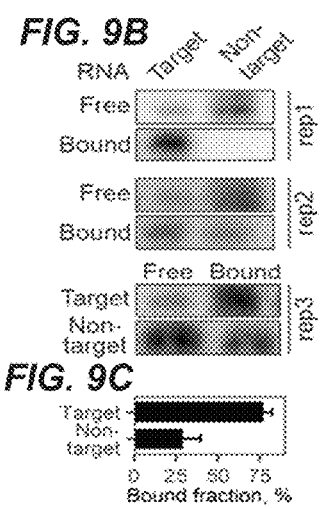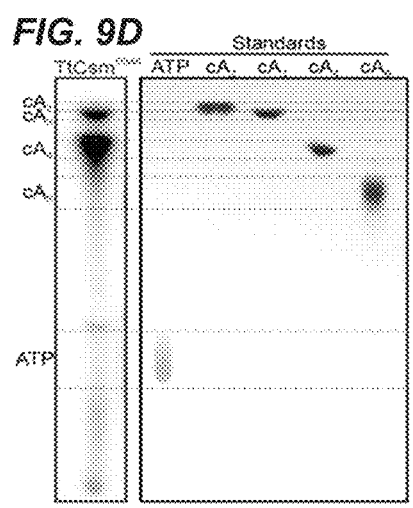
FIG. 9A  FIG. 9B  FIG. 9C  FIG. 9D

FIG. 11D 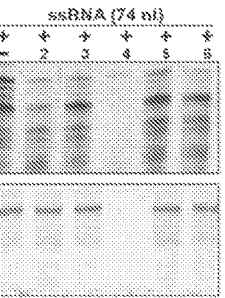 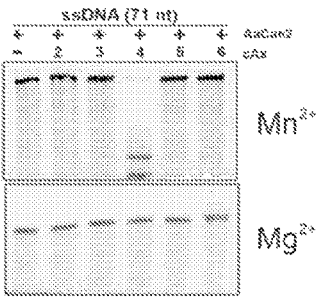

FIG. 14A
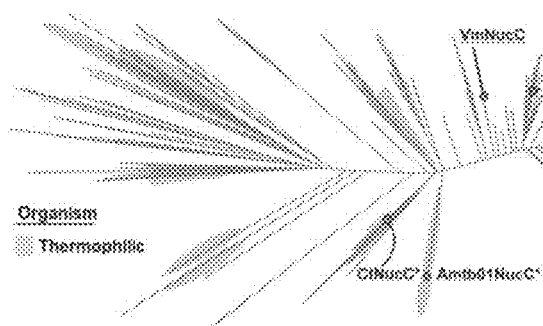
FIG. 14B
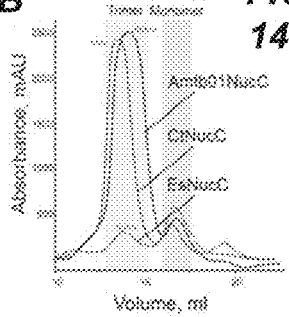
FIG. 14C
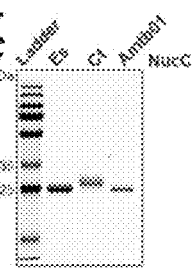
FIG. 14D
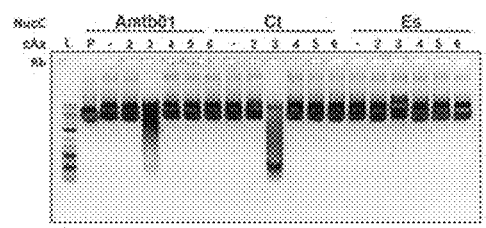
FIG. 14E
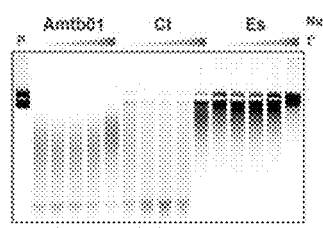
FIG. 14F
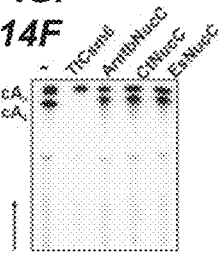
FIG. 14

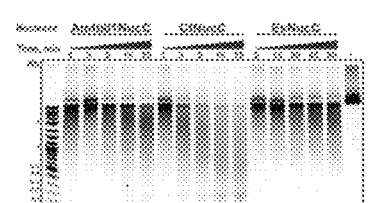
FIG. 15A
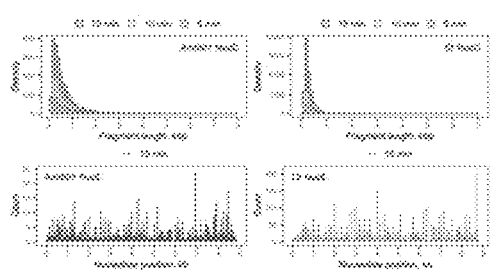
FIG. 15B
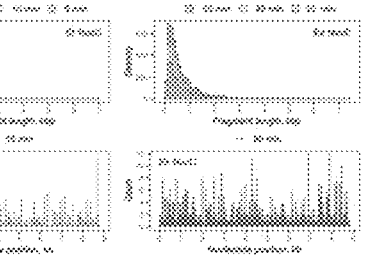
FIG. 15C
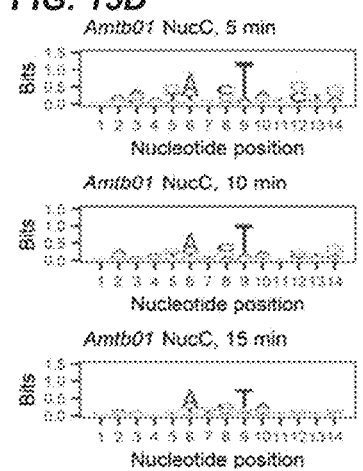
FIG. 15D
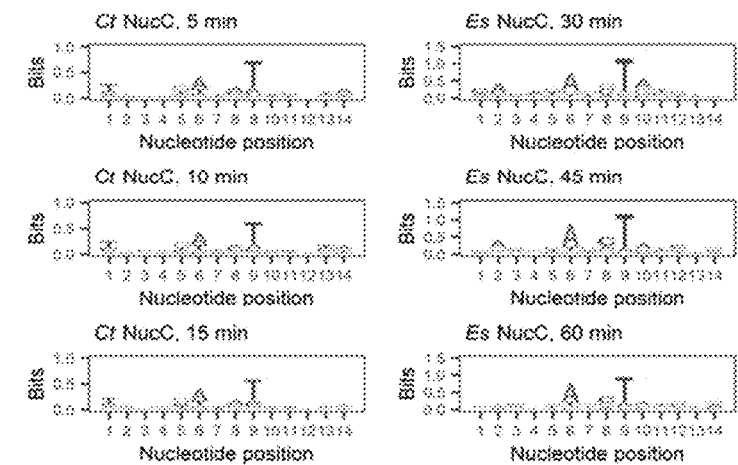
FIG. 15E

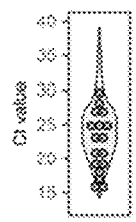
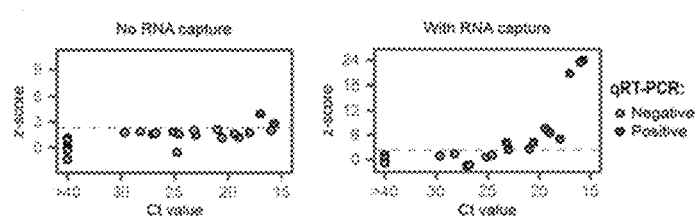
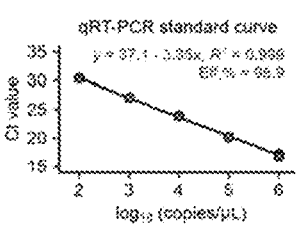
*FIG. 17A*  *FIG. 17B*  *FIG. 17C*
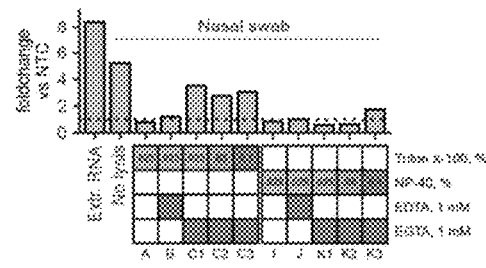
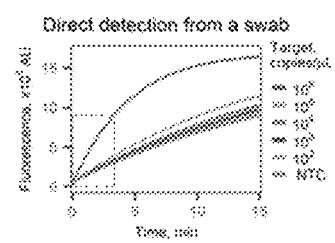
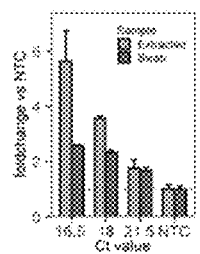
*FIG. 17D*  *FIG. 17E*  *FIG. 17F*

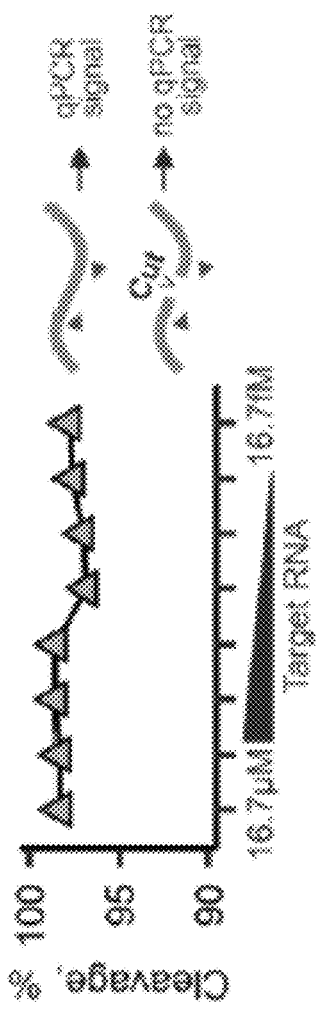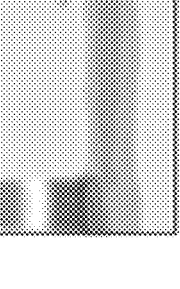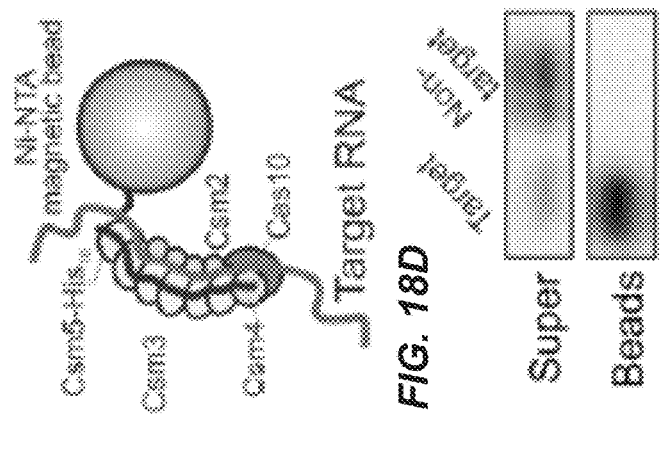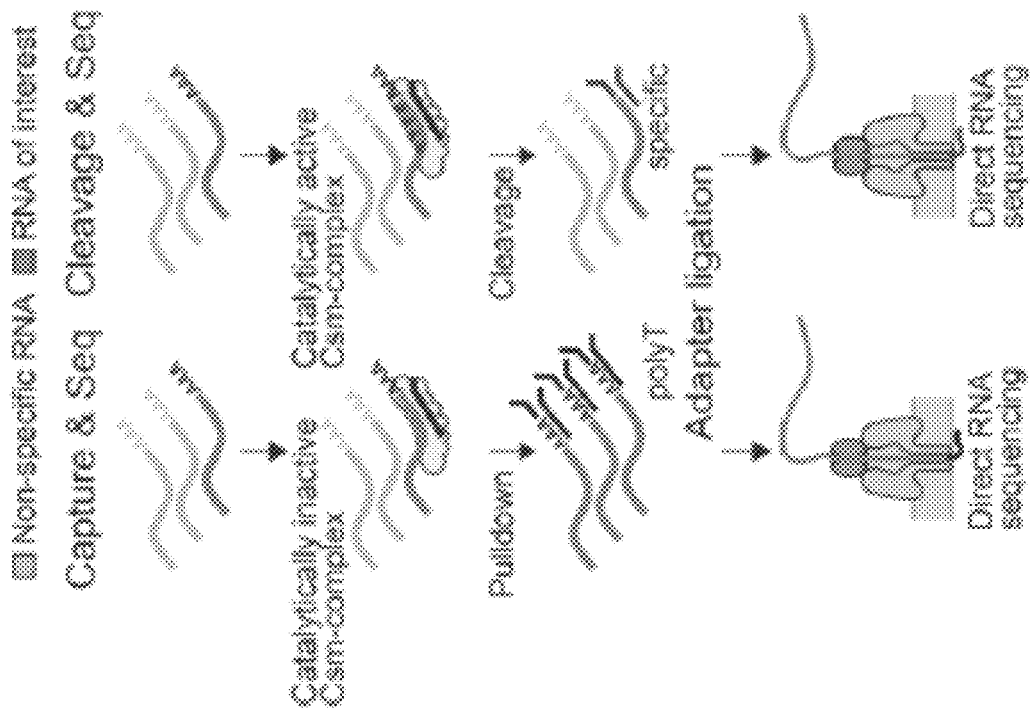

FIG. 19A
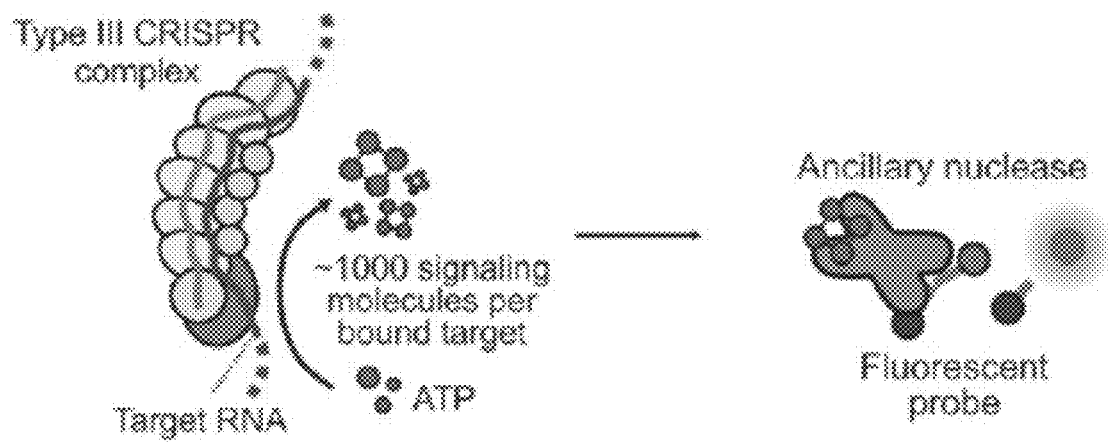
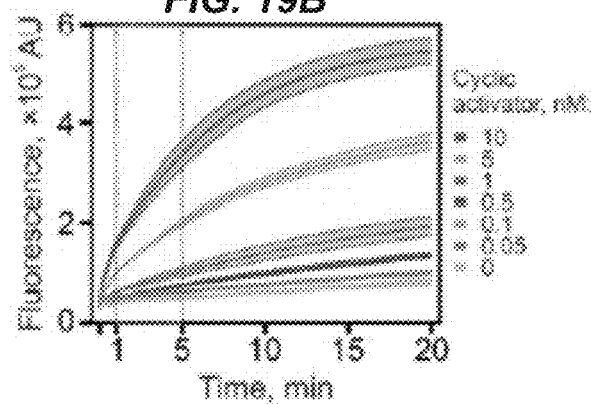
FIG. 19B
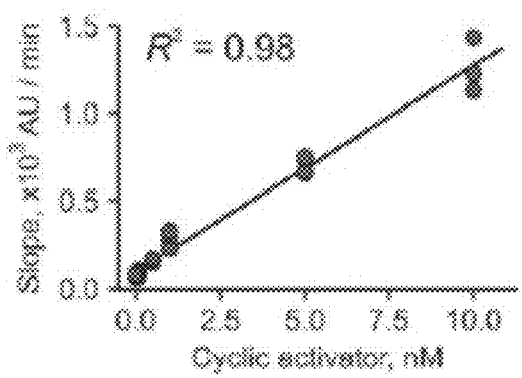
FIG. 19C
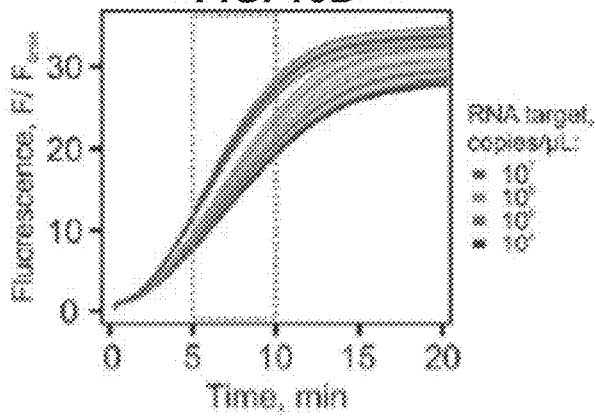
FIG. 19D
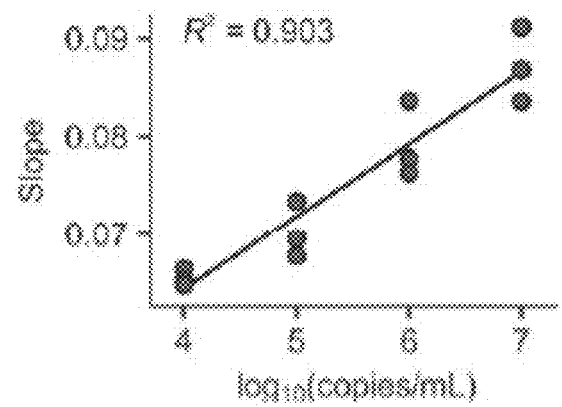
FIG. 19E

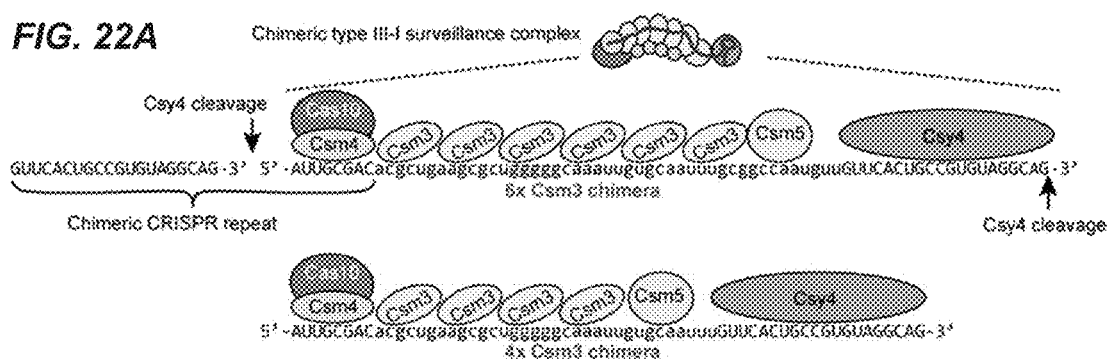
FIG. 22A
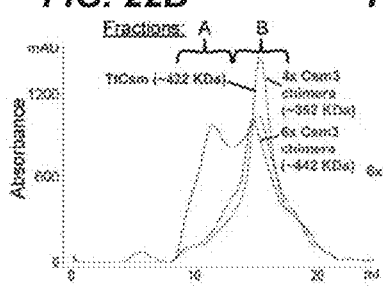
FIG. 22B
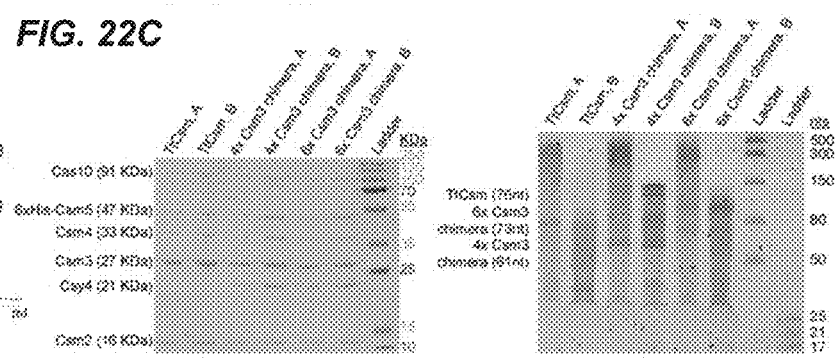
FIG. 22C
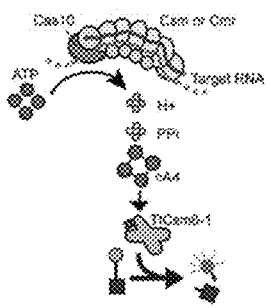
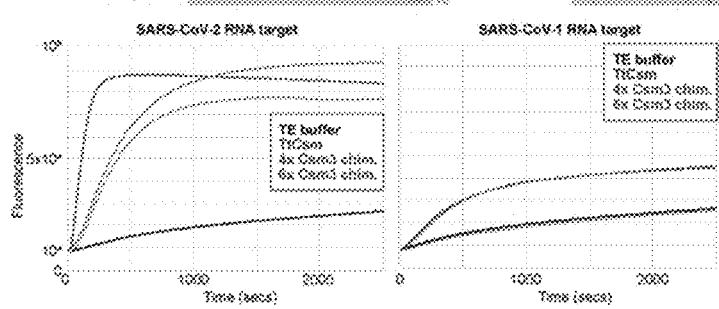
FIG. 22D

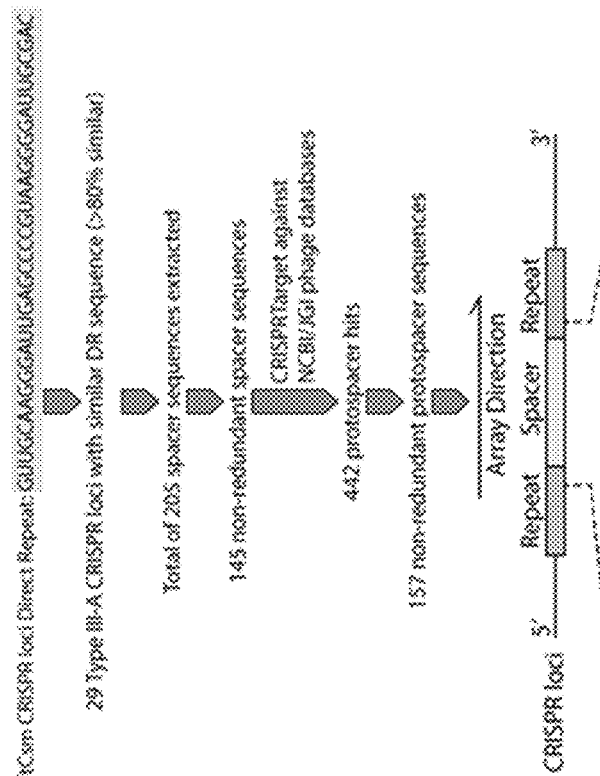
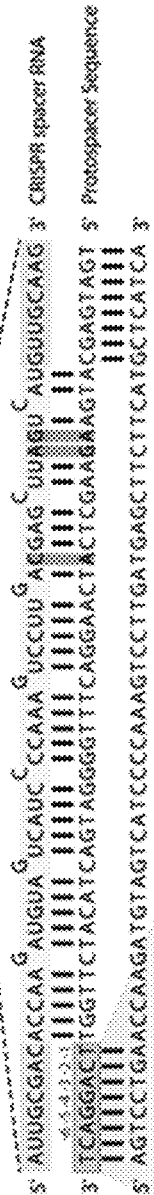
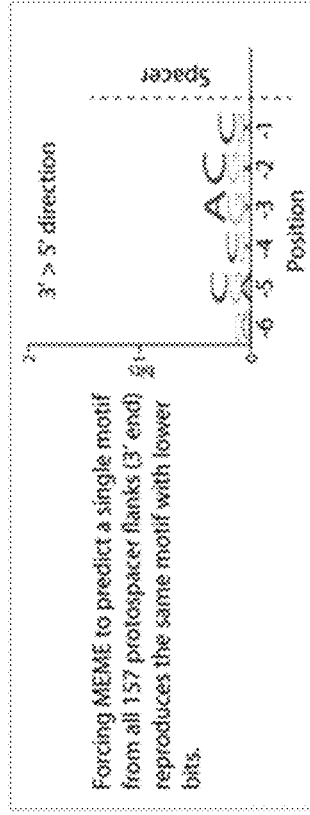
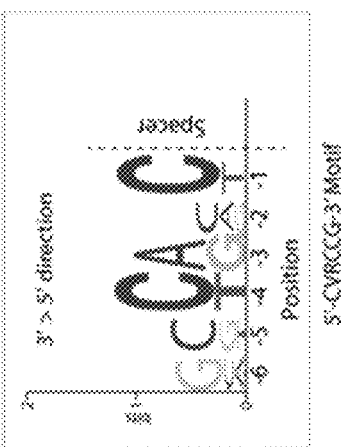
FIG. 26A
FIG. 26B

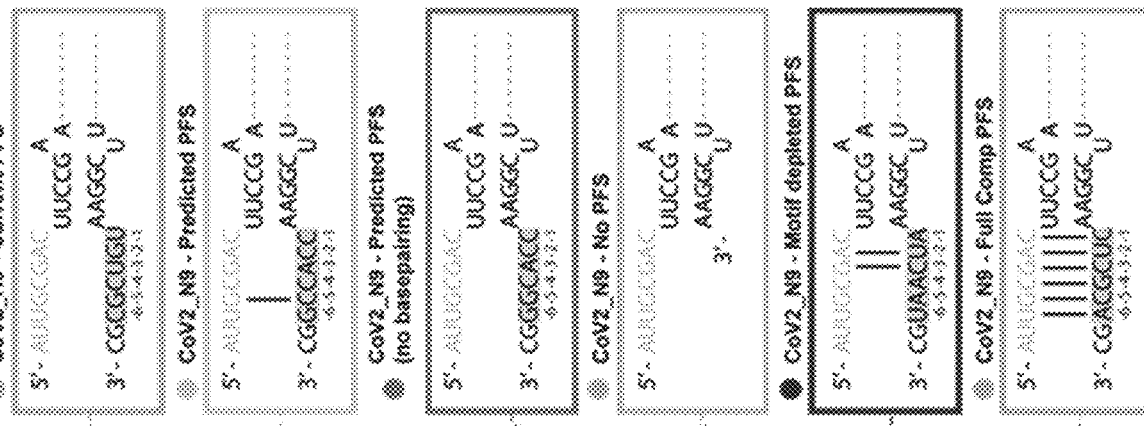
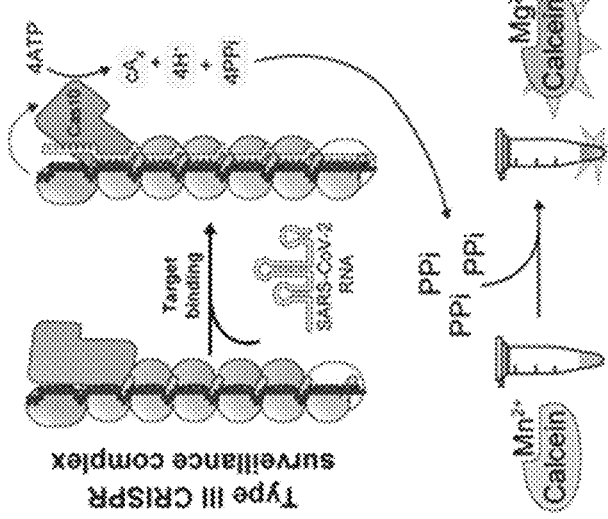
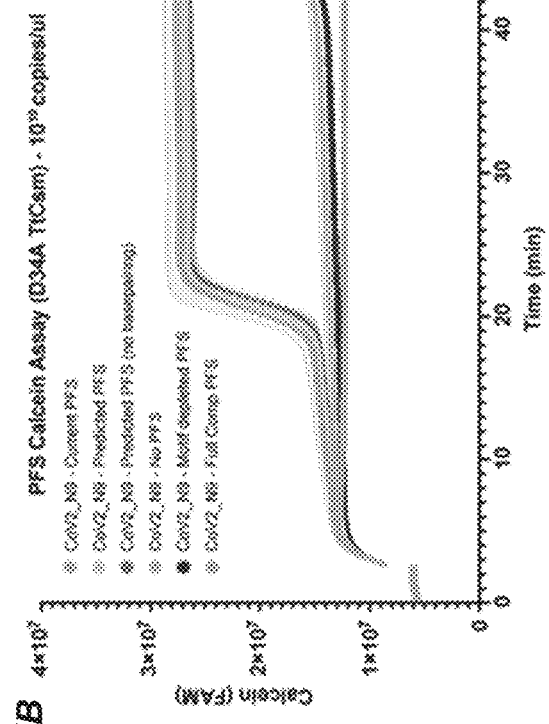
FIG. 27A
FIG. 27B
FIG. 27C

SEQUENCE LISTING

```
Sequence total quantity: 61
SEQ ID NO: 1                 moltype = RNA   length = 10
FEATURE                      Location/Qualifiers
source                       1..10
                             mol_type = other RNA
                             organism = synthetic construct
SEQUENCE: 1
ataaaaaaat                                                                      10

SEQ ID NO: 2                 moltype = RNA   length = 10
FEATURE                      Location/Qualifiers
source                       1..10
                             mol_type = other RNA
                             organism = synthetic construct
SEQUENCE: 2
ataacaacat                                                                      10

SEQ ID NO: 3                 moltype = RNA   length = 10
FEATURE                      Location/Qualifiers
source                       1..10
                             mol_type = other RNA
                             organism = synthetic construct
SEQUENCE: 3
ataagaagat                                                                      10

SEQ ID NO: 4                 moltype = RNA   length = 10
FEATURE                      Location/Qualifiers
source                       1..10
                             mol_type = other RNA
                             organism = synthetic construct
SEQUENCE: 4
ataataatat                                                                      10

SEQ ID NO: 5                 moltype = RNA   length = 10
FEATURE                      Location/Qualifiers
source                       1..10
                             mol_type = other RNA
                             organism = synthetic construct
SEQUENCE: 5
ataccaccat                                                                      10

SEQ ID NO: 6                 moltype = RNA   length = 10
FEATURE                      Location/Qualifiers
source                       1..10
                             mol_type = other RNA
                             organism = synthetic construct
SEQUENCE: 6
atacgacgat                                                                      10

SEQ ID NO: 7                 moltype = RNA   length = 10
FEATURE                      Location/Qualifiers
source                       1..10
                             mol_type = other RNA
                             organism = synthetic construct
SEQUENCE: 7
atactactat                                                                      10

SEQ ID NO: 8                 moltype = RNA   length = 10
FEATURE                      Location/Qualifiers
source                       1..10
                             mol_type = other RNA
                             organism = synthetic construct
SEQUENCE: 8
atagcagcat                                                                      10

SEQ ID NO: 9                 moltype = RNA   length = 10
FEATURE                      Location/Qualifiers
source                       1..10
                             mol_type = other RNA
                             organism = synthetic construct
SEQUENCE: 9
ataggaggat                                                                      10

SEQ ID NO: 10                moltype = RNA   length = 10
FEATURE                      Location/Qualifiers
source                       1..10
                             mol_type = other RNA
                             organism = synthetic construct
```

```
SEQUENCE: 10
atagtagtat                                                                      10

SEQ ID NO: 11         moltype = RNA   length = 10
FEATURE               Location/Qualifiers
source                1..10
                      mol_type = other RNA
                      organism = synthetic construct SEQUENCE: 11
atatcatcat                                                                      10

SEQ ID NO: 12         moltype = RNA   length = 10
FEATURE               Location/Qualifiers
source                1..10
                      mol_type = other RNA
                      organism = synthetic construct SEQUENCE: 12
atatgatgat                                                                      10

SEQ ID NO: 13         moltype = RNA   length = 10
FEATURE               Location/Qualifiers
source                1..10
                      mol_type = other RNA
                      organism = synthetic construct SEQUENCE: 13
atattattat                                                                      10

SEQ ID NO: 14         moltype = RNA   length = 10
FEATURE               Location/Qualifiers
source                1..10
                      mol_type = other RNA
                      organism = synthetic construct SEQUENCE: 14
atccccccat                                                                      10

SEQ ID NO: 15         moltype = RNA   length = 10
FEATURE               Location/Qualifiers
source                1..10
                      mol_type = other RNA
                      organism = synthetic construct SEQUENCE: 15
atccgccgat                                                                      10

SEQ ID NO: 16         moltype = RNA   length = 10
FEATURE               Location/Qualifiers
source                1..10
                      mol_type = other RNA
                      organism = synthetic construct SEQUENCE: 16
atcctcctat                                                                      10

SEQ ID NO: 17         moltype = RNA   length = 10
FEATURE               Location/Qualifiers
source                1..10
                      mol_type = other RNA
                      organism = synthetic construct SEQUENCE: 17
atcggcggat                                                                      10

SEQ ID NO: 18         moltype = RNA   length = 10
FEATURE               Location/Qualifiers
source                1..10
                      mol_type = other RNA
                      organism = synthetic construct SEQUENCE: 18
atcgtcgtat                                                                      10

SEQ ID NO: 19         moltype = RNA   length = 10
FEATURE               Location/Qualifiers
source                1..10
                      mol_type = other RNA
                      organism = synthetic construct
```

-continued

```
SEQUENCE: 19
atctgctgat                                                                        10

SEQ ID NO: 20           moltype = RNA   length = 10
FEATURE                 Location/Qualifiers
source                  1..10
                        mol_type = other RNA
                        organism = synthetic construct
SEQUENCE: 20
atcttcttat                                                                        10

SEQ ID NO: 21           moltype = RNA   length = 10
FEATURE                 Location/Qualifiers
source                  1..10
                        mol_type = other RNA
                        organism = synthetic construct
SEQUENCE: 21
atggtggtat                                                                        10

SEQ ID NO: 22           moltype = RNA   length = 10
FEATURE                 Location/Qualifiers
source                  1..10
                        mol_type = other RNA
                        organism = synthetic construct
SEQUENCE: 22
atgttgttat                                                                        10

SEQ ID NO: 23           moltype = RNA   length = 10
FEATURE                 Location/Qualifiers
source                  1..10
                        mol_type = other RNA
                        organism = synthetic construct
SEQUENCE: 23
attttttat                                                                         10

SEQ ID NO: 24           moltype = RNA   length = 14
FEATURE                 Location/Qualifiers
source                  1..14
                        mol_type = other RNA
                        organism = synthetic construct
SEQUENCE: 24
cgcgaaaaaa cgcg                                                                   14

SEQ ID NO: 25           moltype = RNA   length = 14
FEATURE                 Location/Qualifiers
source                  1..14
                        mol_type = other RNA
                        organism = synthetic construct
SEQUENCE: 25
cgcgaacaac cgcg                                                                   14

SEQ ID NO: 26           moltype = RNA   length = 14
FEATURE                 Location/Qualifiers
source                  1..14
                        mol_type = other RNA
                        organism = synthetic construct
SEQUENCE: 26
cgcgaagaag cgcg                                                                   14

SEQ ID NO: 27           moltype = RNA   length = 14
FEATURE                 Location/Qualifiers
source                  1..14
                        mol_type = other RNA
                        organism = synthetic construct
SEQUENCE: 27
cgcgaataat cgcg                                                                   14

SEQ ID NO: 28           moltype = RNA   length = 14
FEATURE                 Location/Qualifiers
source                  1..14
                        mol_type = other RNA
                        organism = synthetic construct
SEQUENCE: 28
atataccacc atat                                                                   14
```

```
SEQ ID NO: 29           moltype = RNA   length = 14
FEATURE                 Location/Qualifiers
source                  1..14
                        mol_type = other RNA
                        organism = synthetic construct
SEQUENCE: 29
atatacgacg atat                                                           14

SEQ ID NO: 30           moltype = RNA   length = 14
FEATURE                 Location/Qualifiers
source                  1..14
                        mol_type = other RNA
                        organism = synthetic construct
SEQUENCE: 30
cgcgactact cgcg                                                           14

SEQ ID NO: 31           moltype = RNA   length = 14
FEATURE                 Location/Qualifiers
source                  1..14
                        mol_type = other RNA
                        organism = synthetic construct
SEQUENCE: 31
atatagcagc atat                                                           14

SEQ ID NO: 32           moltype = RNA   length = 14
FEATURE                 Location/Qualifiers
source                  1..14
                        mol_type = other RNA
                        organism = synthetic construct
SEQUENCE: 32
atataggagg atat                                                           14

SEQ ID NO: 33           moltype = RNA   length = 14
FEATURE                 Location/Qualifiers
source                  1..14
                        mol_type = other RNA
                        organism = synthetic construct
SEQUENCE: 33
cgcgagtagt cgcg                                                           14

SEQ ID NO: 34           moltype = RNA   length = 14
FEATURE                 Location/Qualifiers
source                  1..14
                        mol_type = other RNA
                        organism = synthetic construct
SEQUENCE: 34
cgcgatcatc cgcg                                                           14

SEQ ID NO: 35           moltype = RNA   length = 14
FEATURE                 Location/Qualifiers
source                  1..14
                        mol_type = other RNA
                        organism = synthetic construct
SEQUENCE: 35
cgcgatgatg cgcg                                                           14

SEQ ID NO: 36           moltype = RNA   length = 14
FEATURE                 Location/Qualifiers
source                  1..14
                        mol_type = other RNA
                        organism = synthetic construct
SEQUENCE: 36
cgcgattatt cgcg                                                           14

SEQ ID NO: 37           moltype = RNA   length = 14
FEATURE                 Location/Qualifiers
source                  1..14
                        mol_type = other RNA
                        organism = synthetic construct
SEQUENCE: 37
atatcccccc atat                                                           14

SEQ ID NO: 38           moltype = RNA   length = 14
FEATURE                 Location/Qualifiers
source                  1..14
                        mol_type = other RNA
                        organism = synthetic construct
SEQUENCE: 38
atatccgccg atat                                                           14
```

```
SEQ ID NO: 39              moltype = RNA   length = 14
FEATURE                    Location/Qualifiers
source                     1..14
                           mol_type = other RNA
                           organism = synthetic construct
SEQUENCE: 39
atatcctcct atat                                                          14

SEQ ID NO: 40              moltype = RNA   length = 14
FEATURE                    Location/Qualifiers
source                     1..14
                           mol_type = other RNA
                           organism = synthetic construct
SEQUENCE: 40
atatcggcgg atat                                                          14

SEQ ID NO: 41              moltype = RNA   length = 14
FEATURE                    Location/Qualifiers
source                     1..14
                           mol_type = other RNA
                           organism = synthetic construct
SEQUENCE: 41
atatcgtcgt atat                                                          14

SEQ ID NO: 42              moltype = RNA   length = 14
FEATURE                    Location/Qualifiers
source                     1..14
                           mol_type = other RNA
                           organism = synthetic construct
SEQUENCE: 42
atatctgctg atat                                                          14

SEQ ID NO: 43              moltype = RNA   length = 14
FEATURE                    Location/Qualifiers
source                     1..14
                           mol_type = other RNA
                           organism = synthetic construct
SEQUENCE: 43
cgcgcttctt cgcg                                                          14

SEQ ID NO: 44              moltype = RNA   length = 14
FEATURE                    Location/Qualifiers
source                     1..14
                           mol_type = other RNA
                           organism = synthetic construct
SEQUENCE: 44
atatggtggt atat                                                          14

SEQ ID NO: 45              moltype = RNA   length = 14
FEATURE                    Location/Qualifiers
source                     1..14
                           mol_type = other RNA
                           organism = synthetic construct
SEQUENCE: 45
cgcggttgtt cgcg                                                          14

SEQ ID NO: 46              moltype = RNA   length = 14
FEATURE                    Location/Qualifiers
source                     1..14
                           mol_type = other RNA
                           organism = synthetic construct
SEQUENCE: 46
cgcgtttttt cgcg                                                          14

SEQ ID NO: 47              moltype = DNA   length = 62
FEATURE                    Location/Qualifiers
source                     1..62
                           mol_type = other DNA
                           organism = synthetic construct
SEQUENCE: 47
tgaactgaac tgaactgaac tgaactgaac tagttcagtt cagttcagtt cagttcagtt        60
ca                                                                       62

SEQ ID NO: 48              moltype = DNA   length = 58
FEATURE                    Location/Qualifiers
source                     1..58
                           mol_type = other DNA
                           organism = synthetic construct
```

```
SEQUENCE: 48
gataatacga ctcactatag ggaactgatt acaaacattg ccgcaaatt gcacaatt        58

SEQ ID NO: 49           moltype = DNA   length = 56
FEATURE                 Location/Qualifiers
source                  1..56
                        mol_type = other DNA
                        organism = synthetic construct
SEQUENCE: 49
gcgcgacatt ccgaagaacg ctgaagcgct gggggcaaat tgtgcaattt gcggcc         56

SEQ ID NO: 50           moltype = DNA   length = 58
FEATURE                 Location/Qualifiers
source                  1..58
                        mol_type = other DNA
                        organism = synthetic construct
SEQUENCE: 50
gataatacga ctcactatag ggaactgatt acaaacattg ccgcaaatt gcacaatt        58

SEQ ID NO: 51           moltype = DNA   length = 56
FEATURE                 Location/Qualifiers
source                  1..56
                        mol_type = other DNA
                        organism = synthetic construct
SEQUENCE: 51
gcgtgacatt ccaaagaatg cagaggcact tggagcaaat tgtgcaattt gcggcc         56

SEQ ID NO: 52           moltype = DNA   length = 741
FEATURE                 Location/Qualifiers
source                  1..741
                        mol_type = other DNA
                        organism = synthetic construct
SEQUENCE: 52
atgacaccag ccaatggact tgaggcttat ttcgcggctc ttcaagaccg tttgcaggcg     60
tcgattaaag ttgcagcagt attggatcac ccgggtgcga aggagatga gacggagatt     120
agttgggaac gcctgttgga cggtcacctt ccccgccgct accaagttgt accgaagtgc    180
atgtttgttg atcataccgg gaagttatca caagaagtag acttggcact tgtgatcgt     240
caatatagca ctctggctct ggaatctcag tcgcgtacag tcgtccctgc ggaagcggct    300
tacgccgtgt ttgaggtaaa accggaactt aaccgtgaaa atgttttata tgctgcggaa    360
aaagctgctt ccgtgcgcgt tttagcccgc acgtctgcac cgattacgga tgctcgtggt    420
gttattgagg agccccgccg tccgtcgccg attattgcgg gacttcttac gacgcgtgca    480
ggttggtctc ctactttggg cgatgccttc tcggcggcgc ttaaagatca gaacagcaat    540
ggattactga acttgggctg tgtactggga gagatcggct ggagggtgaa atatgaaaac    600
aacatcccac gctgggccgc ctcgactccc agtcgcgcgc tggtgttttt ttatttgcgt    660
ctgctgtccg ctcttcagcg tgtgggcaca gtacccgcta tggactacga ccaatggtca    720
gcatttttat cgcatgactg a                                              741

SEQ ID NO: 53           moltype = AA    length = 246
FEATURE                 Location/Qualifiers
source                  1..246
                        mol_type = protein
                        organism = Acidimicrobiales sp.
SEQUENCE: 53
MTPANGLEAY FAALQDRLQA SIKVAAVLDH PGAKGDETEI SWERLLDGHL PRRYQVVPKC     60
MFVDHTGKLS QEVDLALCDR QYSTLALESQ SRTVVPAEAA YAVFEVKPEL NRENVLYAAE    120
KAASVRVLAR TSAPITDARG VIEEPRRPSP IIAGLLTTRA GWSPTLGDAF SAALKDQNSN    180
GLLNLGCVLG EIGWEVKYEN NIPRWAASTP SRALVFFYLR LLSALQRVGT VPAMDYDQWS    240
AFLSHD                                                               246

SEQ ID NO: 54           moltype = DNA   length = 777
FEATURE                 Location/Qualifiers
source                  1..777
                        mol_type = other DNA
                        organism = synthetic construct
SEQUENCE: 54
atgaaatcca caggacgtcg tcttttttggc aagcaagggg ggtcggacat gggtcagatt    60
gatatcaaga gcttgttcta tagccttcaa acgcagatgt gtgcaaaatt atctaccaac    120
cgtcagcaca tccaacaccc tggattaaaa gggggactcat ccgagttgaa ttggattgag   180
tggcttaaaa cgtacctgcc taaacgctac agtgtcgata aagcatttat cattgattgt    240
gacggaaata tgtctgacca aatcgacgta gtaatctacg atcaacagta ttcgcccttc    300
gttttcaacc aggataacgc ctattatatc ccagccgagt cggtgtacgc tattttcgaa    360
gttaagcaag aaatcaacaa agagaacatt atctacgccg tgataagac caagtcggtc    420
cgcagtctga aacgcacttc cacggccatt cctcacgcag gaggttacta tgcgcctaaa    480
ccgcacaaca aatcctgag cggcatctta actttatcga gcgtatggaa tccgccttta    540
ggcaagtcat tgaagaagc tatctactct ttagaagatg agtcaaagtt agatatcggc     600
tgtatcttag ctgaagggtc attccttgca gattataaga atgatgttct gatgaaatcg    660
accgaagaag aatccttgat ttttttcttt ctgaaattac tgatcgagtt acaatctctg    720
gggaccactc cggcaattga tattaattgc tacggtcgcg ccctggattc aattttaa     777
```

```
SEQ ID NO: 55               moltype = AA  length = 242
FEATURE                     Location/Qualifiers
source                      1..242
                            mol_type = protein
                            organism = Clostridium tepidum
SEQUENCE: 55
MGQIDIKSLF YSLQTQMCAK LSTNRQHIQH PGIKGDSSEL NWIEWLKTYL PKRYSVDKAF    60
IIDCDGNMSD QIDVVIYDQQ YSPFVFNQDN AYYIPAESVY AIFEVKQEIN KENIIYAGDK   120
TKSVRSLKRT STAIPHAGGY YAPKPHNKIL SGILTLSSVW NPPLGKSFEE AIYSLEDESK   180
LDIGCILAEG SFLADYKNDV LMKSTEEESL IFFFLKLLIE LQSLGTTPAI DINCYGRALD   240
SI                                                                 242

SEQ ID NO: 56               moltype = DNA  length = 744
FEATURE                     Location/Qualifiers
source                      1..744
                            mol_type = other DNA
                            organism = synthetic construct
SEQUENCE: 56
atgagtggtt tcagtttacc aaagttgctg gcggggctgc acgacaccat tgaacatcgc    60
cttaagctgg cccgtgaaac gatgggacat ccggttaaca aaggcgatgc ttctgaggca   120
gtatggctga atctgttaca aacgtatctg ccccgtcgct acaaagcggc caaggcgcat   180
gtagtttgata gtaccggggc attctccgag cagattgata tagtcgtttt cgatcgccag   240
tacagcccat tggttttcca acatgagggg caaacaatca ttccagccga agtgtatat   300
gcagtctttg aggctaagca gagtattgct gcacctgaga tcacttacgc acaccgcaag   360
gtagcgagcg tgcgccgctt gcatcgcacg agccttccga tcccacatgc aggcggaaca   420
tatcctccga agccgttatc gcgtatcttg gcaggattat taacgttgga gtcggcatgg   480
aacccgccgc ttgggcaaac gcttattgac aacttgtgtg ccggcgacga cgattcccgt   540
cttgacttag gatgtgttgc agcacatggc gtctttgcct gtgaccaggc gggtgtatat   600
tggattcgtc cgcaagggaa ggcggcgaca gcattcttat tcgagttaat cgcccgtttg   660
caggagacgg ctaccgtctc gatgatcgac attcgcgcgt acgctcgctg gttaaccgct   720
gccccagaac agccttccac ctga                                          744

SEQ ID NO: 57               moltype = AA  length = 247
FEATURE                     Location/Qualifiers
source                      1..247
                            mol_type = protein
                            organism = Elioraea sp.
SEQUENCE: 57
MSGFSLPKLL AGLHDTIEHR LKLARETMGH PVNKGDASEA VWLDLLQTYL PRRYKAAKAH    60
VVDSTGAFSE QIDVVVFDRQ YSPLVFQHEG QTIIPAESVY AVFEAKQSIA APEITYAHRK   120
VASVRRLHRT SLPIPHAGGT YPPKPLSRIL AGLLTLESAW NPPLGQTLID NLCAGDDDSR   180
LDLGCVAAHG VFACDQAGVY WIRPQGKAAT AFLFELIARL QETATVSMID IRAYARWLTA   240
APEQPST                                                            247

SEQ ID NO: 58               moltype = DNA  length = 1134
FEATURE                     Location/Qualifiers
source                      1..1134
                            mol_type = other DNA
                            organism = synthetic construct
SEQUENCE: 58
atgagtcaca ttcatgtctg tcttgtatct gaccaagcaa ttccaaatct gacaacagct    60
cttcaattta accccgatac tacggtgtta ttatccacaa acgaaatgaa ggacaaagcc   120
aaacgttttg aaaccgtatt gaagaacaaa ggtttaaagg taaaaacctt gaagatctcg   180
gcgtatgaca tcaacgacgt gattacagtt tcggaatcct tgttaatga ttgtaaaggc   240
tgcaaagtgt cccttaacat tacagggggc actaagattg gacgcttgg taccttccag   300
gtcttttaca ctgcgagcaa accgattttt tatgtcaaca cgaaggacaa cgagatcatt   360
aaactgtatc ccgagaaaga acagcagaag taccccgattg agattagcat ttcaatcaag   420
gactatttgg cagtgtacgg attcaacgtt aagagttatg tcaaggacga ctcctacatc   480
tacaaacgta agaaggtaac tgactatctt gcaaatctgg taatccatcg tcccaatatc   540
atcggtgaaa tcaactataa gttacaaaat tttgaagaaa agtcctatcc tctgaagatt   600
aacatcacta aaaataagca ggtcattaag ctttatgata ttttaaagga ttccggcctt   660
gttaaaatcc gcaataaaag tacgatcgaa atcccagatg ttgagactgc aaagtatttg   720
aatggcattt ggttcgagga atatgtttat atgatggcta agtcccttgg cgccgatgaa   780
gtgaaattga atgtgaaagg ggtatgggac acagtcggaa agcatccgcc gactaacgag   840
tttgatattt tgattagcaa gggtaaccgt ttatttata tcagttgtaa gactgcgaat   900
ccggatcgta agattgatga tacgatgag caaatcggga ggaatacct gtacgaactt   960
gactcaatta gcgattcagc gttggggctt tttggtaaac gtatgctggc ttcagcccgc  1020
gcgattaaga atgactacgt ccgtaagcgt gcagagatcc tgaagatcga cattgccgac  1080
ggccaaaaca tcgccactct gaaggggaaa cttcaacagt ggctttcgaa atga        1134

SEQ ID NO: 59               moltype = AA  length = 377
FEATURE                     Location/Qualifiers
source                      1..377
                            mol_type = protein
                            organism = Archaeoglobi archaeon
SEQUENCE: 59
MSHIHVCLVS DQAIPNLTTA LQFNPDTTVL LSTNEMKDKA KRLETVLKNK GLKVKTLKIS    60
AYDINDVITV SESLLNDCKG CKVSLNITGG TKIGTLGTFQ VFYTASKPIF YVNTKDNEII   120
KLYPEKEQQK YPIEISISIK DYLAVYGFNV KSYVKDDSYI YKRKKVTDYL ANLVIHRPNI   180
```

```
IGEINYKLQN FEEKSYPLKI NITKNKQVIK LYDILKDSGL VKIRNKSTIE IPDVETAKYL  240
NGIWFEEYVY MMAKSLGADE VKLNVKGVWD TVGKHPPTNE FDILISKGNR LFYISCKTAN  300
PDRKIDDTDE TIGKEYLYEL DSISDSALGL FGKRMLASAR AIKNDYVRKR AEILKIDIAD  360
GQNIATLKGK LQQWLSK                                                 377

SEQ ID NO: 60          moltype = DNA  length = 1911
FEATURE                Location/Qualifiers
source                 1..1911
                       mol_type = other DNA
                       organism = synthetic construct
SEQUENCE: 60
atgcaagccc cggtgtatct gtgcttgctg ggaaacgacc cagctcctgc ctacctgggt   60
ctgaaggttg tggaacgtga ggctggccgc gtggcgaagg ccgtgttcta ttcctttccc  120
gcatggaatg aggaaatatg gaagaaacgc caggctttct tccgtttatt gtcggagaag  180
ggggtgttat atgaggaacg tcctttggag aaaggtcttg aagaggcgga ggcccgtgaa  240
gtctgggtta atcttacggg tggggctaag tattgggcgg tccgcttttt gggtcactgg  300
cgccgtcctg gtgcgcgtgt attcttggtc gaaggccacc gcgctctgga ggcaccgcgt  360
gcgcttttcc tttggccgcg cgaagaggag cgctcattgg aggcggaagc gcttactctt  420
gaagagtatg cccgcttata tcttgagccc ttgggcgaag cctgggagcg tgtctctccg  480
ccaggagctt ttccgcccgg agcgcaggct gcgcgtcttc cgggccgcga gggcggtgtt  540
ttcgttgtac accgcggcct gccgtactgg tattgggtgc gtcctcactt gggcggcgaa  600
gcaaaagaca tgtcccgtaa agctctgagt gctttcagcg gggcggcgaa gcgcctgggg  660
ggacagttat gtcttcctgt cgttccctat cacaaagcgc atttgcgctc ccgccacccg  720
aaggaacgtg aaaatgtttt tgctcgctgg cgtgcatggg cgcgtgaata cggggtattt  780
ttagtagatc cagggcgtcc cctggaggaa gaagtcgcgt ccctgatcaa gggtaaagcc  840
tccaagaaag ctttgccgct gccccaagaa ggtccgctgt tacttgcgct ggtgtcggag  900
caagccgtgc ccctttatgc cgcctatctg cacgcaggac ctcgtgaagt ctatctgttg  960
acgacacccg aaatggaatc acgtctgcgt tgggccgaag cctccttccg tggaaagggt 1020
gtacgtgtcc atcgttcttt cctttccggt ccttgggcgt tgcgcgaggt ccgtgacttg 1080
ttggcaccga tggtagaaga agcgttgcgt cgtggccatc cagtacacgc caatcttaac 1140
agtggaacaa ctgcaatggc cttgggcctg tatctggcat tacgtgatgg agcccgcgcg 1200
cattatctgg atggagatcg tttattgctt ttagacgggg gagaggcgga ggtcccatgg 1260
gaagagggcc gcccagagga tcttcttgct ctgcgtggtt accgttttga ggaggaatat 1320
cccgacgctc gccccgatcc tggcttattg gcgctggcag aggagatctt acgtcgctgg 1380
gatgaggttc aaactagttg ggaggcttct ccactggttc gtcgttttct taagttctgg 1440
aaaaaacgtt ttggacaagc gttttcccccg aagcgtttaa gccgcctgaa ggggttaccg 1500
ttggaatatg cagtgtactc tcatttaaat gcacatttag ctcccaaggg cggccaggct 1560
cgtatgggcg gacaccttgt acctttgggt gggaatgaag cccttgctcc caatcgact  1620
gaagtagatg gcgtcttctt tcaccgcggc gcgttatggt tcgtcgagtg caagcccacg 1680
gatgaaggac ttcgtgagcg tgctccgatc atgcgggagt tggtccgtag cgtaggcggc 1740
gttgaagctc gcggtttaat ggtcgcacgc cgttggcgcg gggcacccc  tcctgcctct 1800
ccaaacttag tttatatggc actggaaggc ggagaaggag taggggtata ccgcttccca 1860
gaagaattag agaaagcact ttctcgtaat cctgcaccac gccgtgggta a          1911

SEQ ID NO: 61          moltype = AA  length = 636
FEATURE                Location/Qualifiers
source                 1..636
                       mol_type = protein
                       organism = Thermus thermophilus
SEQUENCE: 61
MQAPVYLCLL GNDPAPAYLG LKVVEREAGR VAKAVFYSFP AWNEEYGKKR QAFFRLLSEK   60
GVLYEERPLE KGLEEAEARE VWVNLTGGAK YWAVRFLGHW RRPGARVFLV EGHRALEAPR  120
ALFLWPREEE RSLEAEALTL EEYARLYLEP LGEAWERVSP PGAFPPGAQA ARLPGREGGV  180
FVVHRGLPYW YWVRPHLGGE AKDMSRKALS AFSGEAKRLG GQLCLPVVPY HKAHLRSRHP  240
KERENVFARW RAWAREYGVF LVDPGRPLEE EVASLIKGKA SKKALPLPQE GPLLLALVSE  300
QAVPLYAAYL HAGPREVYLL TTPEMESRLR WAEAFFRGKG VRVHRSFLSG PWALREVRDL  360
LAPVVEEALR RGHPVHANLN SGTTAMALGL YLALRDGARA HYLDGDRLLL LDGGEAEVPW  420
EEGRPEDLLA LRGYRFEEEY PDARPDPGLL ALAEEILRRW DEVQTSWEAS PLVRRFLKFW  480
KKRFGQAFPP KRLSRLKGLP LEYAVYSHLN AHLAPKGGQA RMGGHLVPLG GNEALAPQST  540
EVDGVFFHRG ALWFVECKPT DEGLRERAPI MAELVRSVGG VEARGLMVAR RWRGAPPPAS  600
PNLVYMALEG GEGVGVYRFP EELEKALSRN PAPRRG                            636
```

NUCLEIC ACID DETECTION USING TYPE III CRISPR COMPLEX

CROSS-REFERENCE TO RELATED APPLICATIONS

This application claims the benefit of priority of U.S. Provisional Application No. 63/224,356, filed on Jul. 21, 2021, U.S. Provisional Application No. 63/320,198, filed on Mar. 15, 2022, and U.S. Provisional Application No. 63/320,199, filed on Mar. 15, 2022, each of which are incorporated by reference in their entireties herein for all purposes.

SEQUENCE LISTING

The contents of the electronic sequence listing (065869-0570295_SEQUENCE_LISTING.xml; 61,386 bytes; and Date of Creation: Sep. 16, 2022) is herein incorporated by reference in its entirety.

BACKGROUND

Detecting target nucleic acids of interest, such as ribonucleic acid (RNA) or deoxyribonucleic acid (DNA), from a complex mixture may be difficult because of the noise in the complex mixture. For example, a complex mixture such as a nasal swab from a human or other type of sample from a subject may include various substances. These substances may include a target nucleic of interest to be detected, other nucleic acids, and/or other substances. Any target nucleic acid in the sample may have a relatively small concentration compared to the concentration of other substances. This in turn may result in a low detection signal being produced, resulting in low signal-to-noise. While PCR and similar techniques may be able to amplify targets and therefore improve signal-to-noise, they may require complex laboratory processes that take too long for efficient identification and dissemination of target nucleic acids.

SUMMARY

The disclosure relates to using an engineered type III Clustered Regularly Interspaced Short Palindromic Repeat (CRISPR) complex to improve detection signals for a target nucleic acid such as RNA or DNA in a sample. The target nucleic acid may be RNA or DNA. The sample may include a complex mixture. The complex mixture may be a sample from a subject to detect whether the sample includes the target nucleic acid. The target nucleic acid to be detected may be nucleic acid from a pathogen or other foreign organism or may be nucleic acid from the subject.

Improving the detection signal from the target nucleic acid may include capturing and concentrating the target nucleic acid using the engineered type III CRISPR complex, which binds to the target nucleic acid through a CRISPR guide engineered to be complementary to at least a portion of the target nucleic acid. The bound engineered type III CRISPR complex may be used to pull down the target nucleic acid from the sample, which may be a complex mixture. Capture and concentration of the target nucleic acid by the engineered type III CRISPR complex may improve signal generation for detection without prior amplification of the target nucleic acid in the sample.

Improving the detection signal from the target nucleic acid in the sample may include adding a nuclease that is activated by the bound engineered type III CRISPR complex. An engineered detection system may detect nuclease activity. Addition of an appropriate nuclease may improve signal generation for detection without prior amplification of the target nucleic acid in the sample, which may be a complex mixture.

In one aspect, the disclosure relates to methods and engineered complexes to amplify signal generation for detection using capture and concentration alone. In another aspect, the disclosure relates to methods and engineered complexes for identification and addition of one or more nucleases that are activated by the bound engineered type III CRISPR complex and detection of the activated nucleases. In another aspect, the disclosure relates to methods and engineered complexes that use both capture and concentration using the engineered type III CRISPR complex, and identification and addition of one or more nucleases that are activated by the bound engineered type III CRISPR complex and detection of the activated nucleases.

The various capture and concentrate methods disclosed herein, improve upon detection methods describe in U.S. patent application Ser. No. 17/240,858, filed Apr. 26, 2021, the content of which is incorporated by reference in its entirety herein for all purposes.

In some aspects, the techniques described herein relate to a method, wherein the detectable activity includes generation of pyrophosphate.

In some aspects, the techniques described herein relate to a method, wherein the generation of pyrophosphate is detectable via chelation of Manganese ions from solution, leading to Calcein binding to Magnesium ions instead, resulting in an increase in fluorescence.

In some aspects, the techniques described herein relate to a method, wherein the detectable activity includes generation of protons.

In some aspects, the techniques described herein relate to a method, wherein the generation of protons is detectable via a pH-sensitive dye.

In some aspects, the techniques described herein relate to a method, wherein the pH-sensitive dye includes Phenol Red, also known as Phenolsulfonphthalein, CAS Number 143-74-8.

In some aspects, the techniques described herein relate to a method, wherein the generation of protons is detectable via a semiconductor.

In some aspects, the techniques described herein relate to a method of programmatically capturing and detecting target nucleic acid in a sample based on an engineered type III CRISPR complex, the method including: capturing the target nucleic acid in the sample using the engineered type III CRISPR-Cas complex, the engineered type III CRISPR-Cas complex including: a CRISPR guide including a CRISPR guide sequence engineered to be complementary to the target nucleic acid; concentrating the captured target nucleic acid to amplify detectable activity of the engineered type III CRISPR-Cas complex; and detecting the captured and concentrated target nucleic acid based on the detectable activity of the engineered type III CRISPR-Cas complex.

In some aspects, the techniques described herein relate to a method, wherein the sample includes a complex mixture and wherein the capturing and concentrating are performed without prior amplification of the target nucleic acid in the complex mixture.

In some aspects, the techniques described herein relate to a method, wherein the detectable activity includes generation of a linear or cyclic oligonucleotide.

In some aspects, the techniques described herein relate to a method, wherein the generation of the linear or cyclic oligonucleotide is detectable via a nuclease that is activated by the linear or cyclic oligonucleotide.

In some aspects, the techniques described herein relate to a method, wherein the nuclease includes a Can nuclease and wherein the type III CRISPR system includes the Can nuclease.

In some aspects, the techniques described herein relate to a method, wherein the Can nuclease includes Can1 and/or Can2.

In some aspects, the techniques described herein relate to a method, wherein the nuclease includes a NucC nuclease and wherein the type III CRISPR system includes the NucC nuclease.

In some aspects, the techniques described herein relate to a method, wherein contacting the nucleic acid in the sample with the engineered type III CRISPR-Cas complex includes: contacting the captured and concentrated nucleic acid with a fluorophore and a quencher tethered together by a nucleic acid tether, wherein the activated nuclease cleaves the nucleic acid tether to thereby release the fluorophore from the quencher; and detecting a level of fluorescence of the released fluorophore.

In some aspects, the techniques described herein relate to a method, wherein the tether includes a ribonucleic acid and/or a deoxyribonucleic acid tether.

In some aspects, the techniques described herein relate to a method, wherein the engineered type III CRISPR complex is Histidine-tagged (His-tagged), and wherein capturing the target nucleic acid includes: incubating the sample with the His-tagged engineered type III CRISPR complex to bind the His-tagged engineered type III CRISPR complex with the target nucleic acid; and binding the His-tagged engineered type III CRISPR complex with bound target nucleic acid to magnetic particles.

In some aspects, the techniques described herein relate to a method, wherein the magnetic particles include Ni-NTA beads.

In some aspects, the techniques described herein relate to a method, wherein concentrating the captured target nucleic acid includes: applying a magnet to generate a pellet including the His-tagged engineered type III CRISPR complex bound to the target nucleic acid and the magnetic particles.

In some aspects, the techniques described herein relate to a method, wherein the detectable activity includes generation of a linear or cyclic oligonucleotide that is detectable via a nuclease activated by the linear or cyclic oligonucleotide, the method further including: resuspending the pellet in a solution including reaction buffer containing ATP to activate polymerase activity of the His-tagged engineered type III CRISPR complex, wherein the polymerase activity generates the linear or cyclic oligonucleotide that activates the nuclease.

In some aspects, the techniques described herein relate to a method, further including: adding the nuclease, a fluorophore, and a quencher tethered together by a nucleic acid tether, wherein the activated nuclease cleaves the nucleic acid tether to release the fluorophore; and detecting a level of fluorescence of the released fluorophore.

In some aspects, the techniques described herein relate to a method, wherein the linear or cyclic oligonucleotide includes cA3 and/or cA4 that activates a NucC nuclease.

In some aspects, the techniques described herein relate to a method, wherein the linear or cyclic oligonucleotide includes cA3 and/or cA4 that activates a Can nuclease.

In some aspects, the techniques described herein relate to a method, wherein the sample is a complex mixture obtained from a subject.

In some aspects, the techniques described herein relate to a method, wherein the sample includes a nasopharyngeal swab sample.

In some aspects, the techniques described herein relate to a method, wherein the target nucleic acid in the sample includes ribonucleic acid (RNA).

In some aspects, the techniques described herein relate to a method, wherein the RNA includes at least a portion of an RNA genome of a virus.

In some aspects, the techniques described herein relate to a method, wherein the viral RNA includes an RNA from the genome of severe acute respiratory syndrome coronavirus 2 (SARS-CoV-2).

BRIEF DESCRIPTION OF THE FIGURES

Features of the present disclosure may be illustrated by way of example and not limited in the following figure(s), in which like numerals indicate like elements, in which:

FIG. 2A shows a phylogeny of thermostable NucC proteins.

FIG. 2B shows size exclusion chromatography (SEC) profiles for NucC proteins derived from *Elioraea* sp.

FIG. 2C shows an SDS-PAGE of purified trimeric NucC homologs.

FIG. 4A shows a schematic of an example of a type III-CRISPR surveillance complex coupled with NucC and Can DNases for detection of SARS-CoV-2 RNA.

FIG. 4B shows a schematic of activated TexNucC and TthCan DNases cleavage of a fluorescent DNA reporter (43 bp dsDNA) with an internal fluorophore (fluorescein) and a 3' terminal quencher (BHQ-1), to produce a fluorescent signal.

FIG. 4C shows a schematic of activated TexNucC and TthCan DNase cleavage of a 1-3 Kb dsDNA substrate tagged with biotin at one 5' end and digoxigenin at the other 5' end.

FIG. 5A shows a schematic of an example of type III CRISPR-based RNA concentration.

FIG. 5B shows an image of a UREA-PAGE for target and non-target RNA.

FIG. 5C Csm-based direct RNA detection using 3 μL of sample is compared to an assay with additional RNA capture and concentration step.

FIG. 5D shows an image of a TLC plate comparing results with and without RNA capture.

FIG. 5E shows a plot of TtCsm6-based fluorescent readout is used to sense cA4 generated by TtCsm$^{Csm3-D34A}$ with or without RNA capture step as shown in FIG. 5C.

FIG. 7A shows a schematic illustrating that target bound TtCsm complex generates cA3 and cA4 (primary product).

FIG. 7B shows cleavage results of CtNucC.

FIG. 7C shows plots of CtNucC (300 nM), TtCan1 (300 nM) and AaCan2 (300 nM) cleavage assays with fluorescent dsDNA reporter in the presence of varying cA3 activator concentrations.

FIG. 7D shows plots of TtCsm RNA detection assays coupled with AaCan2 (ssRNA reporter), CtNucC (dsDNA reporter) and combination of AaCan2 and CtNucC (both reporters).

FIG. 8A shows plots of positive SARS-CoV-2 and negative RNA samples tested with TtCsm-AaCan2 detection assay with and without upstream RNA capture step.

FIG. 8B shows a scatter plot of a distribution of Ct values (N1 CDC primers) of RNA samples tested in FIG. 8A.

FIG. 8C shows a schematic of an example of a TtCsm-based RNA capture assay from a nasopharyngeal swab coupled with AaCan2-based fluorescent detection.

FIG. 8D shows a plot of nasopharyngeal swab sample positive for SARS-CoV-2 with RT-qPCR used to make 10-fold serial dilutions in a negative nasopharyngeal swab.

FIG. 9A shows a schematic of TtCsm-complex bound to a Ni-NTA magnetic bead and an image of an SDS-PAGE of TtCsm complex after pull-down with NI-NTA magnetic beads.

FIG. 9B shows results of sequence-specific RNA enrichment with TtCsm$^{Csm3-D34A}$ complex tested using P32 5'-end labeled in vitro transcribed (IVT) RNA fragments.

FIG. 9C shows a plot of RNA bands shown in FIG. B quantified using ImageJ.

FIG. 9D shows an image of a TLC plate of TtCsm$^{Csm3-D34A}$-complex products, including cA3 and cA4.

FIG. 11D shows results of cleavage assays with AaCan2 (200 nM) in in the presence cyclic oligoadenylates with 2-6 bases (cA2-cA6, 45 nM) and in a buffer having $Mg^{2+}$.

FIG. 14A shows an example of a maximum-likelihood phylogeny of NucC orthologs.

FIG. 14B shows size-exclusion chromatography (SEC) profiles of purified NucC orthologs.

FIG. 14C shows an example of SDS-PAGE of purified NucC orthologs.

FIG. 14D shows an example of plasmid (Addgene #105621, 1 ug) digestion with thermostable NucC orthologs (45 nM) in the presence of cyclic oligoadenylates with 2-6 bases (cA2-cA6, 45 nM).

FIG. 14E shows DNase activity of NucC orthologs was tested across a temperature range.

FIG. 14F shows cA3 and cA4 hydrolysis by EsNucC, CtNucC and Amtb01NucC.

FIG. 15A shows an example of a time-course plasmid (Addgene #105621) digestion with thermostable NucC homologs in the presence of cA3.

FIG. 15B shows an example of plasmid DNA cleavage fragments shown in a were end-prepped and deep-sequenced using Oxford Nanopore.

FIG. 15C shows an example of cleavage maps for nucleases.

FIG. 15D shows an example of sequence logos.

FIG. 15E shows a plot of sequencing depth at cut sites.

FIG. 17A shows a Violin plot of a distribution of Ct values in 858 RNA samples collected and tested with RT-qPCR (N1 diagnostic primers, CDC) over a period of time.

FIG. 17B shows a plot of results of RNA samples that were tested with qRT-PCR (x-axis) and TtCsm-based detection assay (y-axis) with and without upstream RNA capture step.

FIG. 17C shows a plot of results of serial dilutions of SARS-CoV-2 RNA standard which was used to generate a standard curve with N1 CDC primers and probe mix.

FIG. 17D shows a plot of results of Csm-based target RNA concentration followed by Csm-based detection with TtCsm6 and a fluorescent reporter was performed from a mock sample with and without lysis buffer (no lysis).

FIG. 17E shows a plot of results of TtCsm-based RNA capture assays coupled with AaCan2 readout performed using nasopharyngeal swab sample positive for SARS-CoV-2 with RT-qPCR and its 10-fold serial dilutions in a negative nasopharyngeal swab.

FIG. 17F shows an example of a plot of fold change vs non-targeting control (NTC) vs Ct value.

FIG. 18A shows a schematic example of a capture & sequence approach that uses the type-III CRISPR-Cas complex (e.g., Csm or Cmr) to pulldown specific RNAs from total RNA, and then all mRNAs in the enriched sample are sequenced.

FIG. 18B shows a schematic example of His-tagged Csm-complex bound to Nickel-derivatized (Ni-NTA) magnetic bead.

FIG. 18C shows an example of an image of an SDS-PAGE of Csm-complex after pull-down with nickel-derivatized magnetic beads.

FIG. 18D shows an example of results of sequence-specific RNA enrichment with TtCsm$^{Csm3-D34A}$ complex was tested using $^{32}$P 5'-end labeled IVT RNA fragments.

FIG. 18E shows a plot illustrating Csm-complexes efficiently cut target at femtomolar concentrations.

FIG. 19A shows a schematic example of type III CRISPR RNA detection technology.

FIG. 19B shows a plot of kinetics of fluorescence ssRNA reporter cleavage by AaCan2 (300 nM) over a range of cyclic activator (i.e., cA4) concentrations.

FIG. 19C shows a plot of reaction rates quantified in FIG. 19A.

FIG. 19D shows a plot of target RNA presence detected with TtCsm-complex (25 nM) in real time with AaCan2-based fluorometric readout.

FIG. 19E shows a plot of reaction rates quantified in FIG. 19D.

FIG. 22A shows a schematic of the RNA spacer and guide design.

FIG. 22B shows an example plot of results of size exclusion chromatography of wildtype TtCsm complex (blue) overlayed with 6×Csm3 and 4×Csm3 chimeric complexes.

FIG. 22C shows SDS-PAGE and Urea-PAGE gels of the proteins and RNAs present in fractions A and B of the three different protein complexes.

FIG. 22D shows a schematic and plots of 4×Csm3 and 6×Csm3 chimeric complexes.

FIG. 26A shows an example of a workflow to identify a conserved protospacer flanking sequence specific to a subset of type III CRISPR surveillance complexes.

FIG. 26B shows an example of the PFS identified by MEME for a subset of 157 protospacer sequences and for all protospacer sequences.

FIG. 27A shows a schematic of the Calcein-based assay to measure ATP polymerization by target-RNA bound type III CRISPR surveillance complexes.

FIG. 27B shows plots of Calcein-based assays to measure ATP polymerization by the "N9" guided TtCsm complex mixed with $10^{10}$ copies of one of six different target RNA sequences.

FIG. 27C shows a schematic that describes the differences in the PFS between each of the otherwise identical six target RNA sequences.

DETAILED DESCRIPTION

Figure 1A:
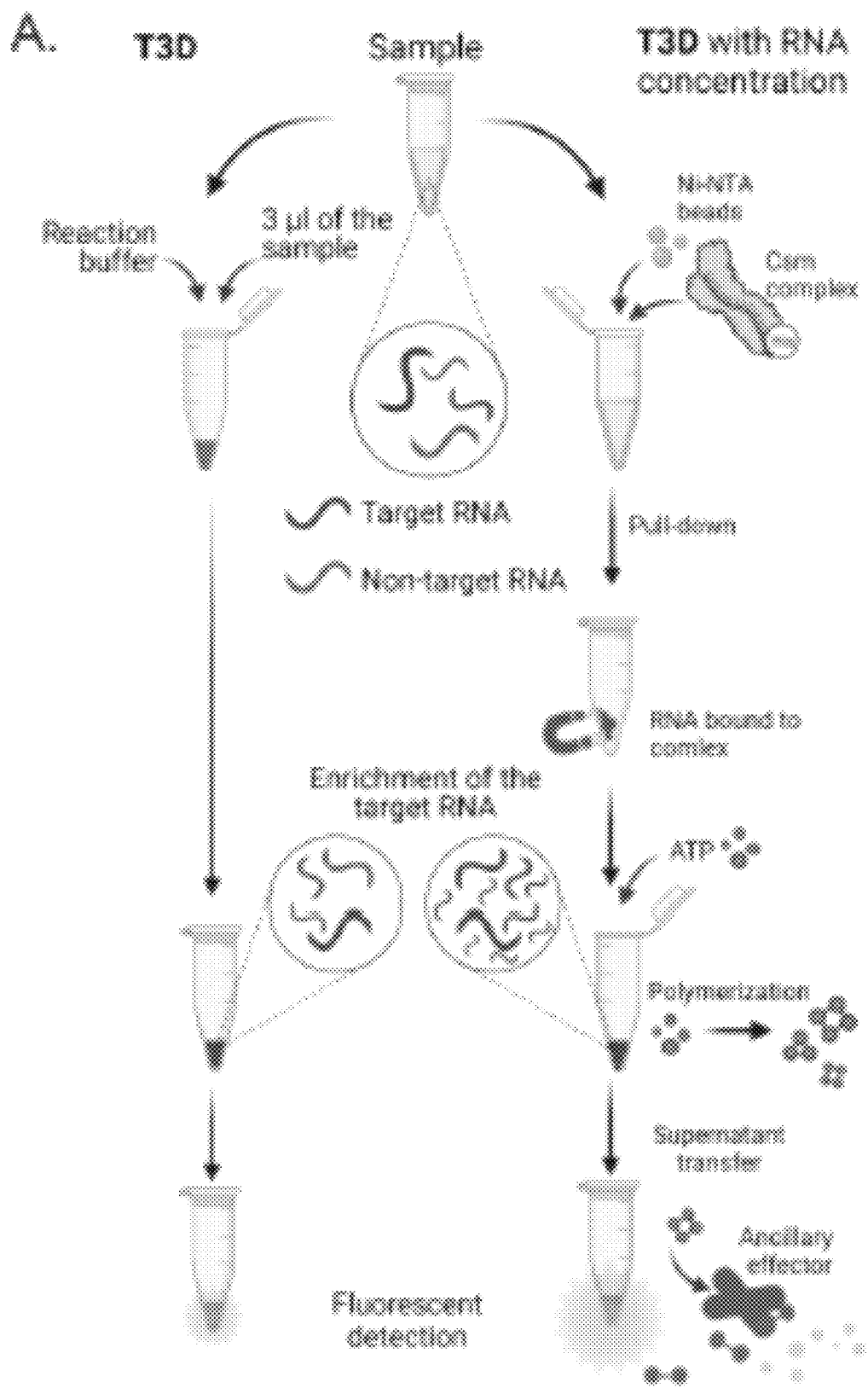
FIG. 1A shows an example of Type III CRISPR-based RNA concentration and enhanced detection.

There is an urgent need for inexpensive new technologies that enable fast, reliable, and scalable detection of RNA. U.S. patent application Ser. No. 17/240,858, filed Apr. 26, 2021, the entirety of which is incorporated by reference for all purposes, disclosed repurposing the type III CRISPR-Cas system for sequence specific detection of SARS-CoV-2 in an assay that can be performed in one hour or less. However, direct detection of RNA using type III CRISPR-based diagnostics (T3D) may not be sufficiently sensitive for many applications. To improve T3D sensitivity, we have developed a method that enables target RNA concentration and combines ancillary nucleases (i.e., Csm6, NucC and Can1), which are activated by cA4 and cA3, respectively.

Although qPCR (quantitative polymerase chain reaction) remains the "gold standard" for nucleic acid detection, it requires sophisticated equipment, trained personnel, efficient specimen transport to high-complexity labs, and reliable reporting systems [Reference 1]. While the complexity and turnaround times necessary for qPCR are acceptable for many diagnostic applications, the SARS-CoV-2 (Severe Acute Respiratory Syndrome Coronavirus 2) pandemic reveals an urgent need for diagnostics that are easy to distribute, simple to perform, and fast enough to stop transmission of a contagious disease [Reference 1]. Although rapid antigen tests and isothermal amplification methods have helped address this need, these and other emerging methods have limitations related to sensitivity, versatility, or specificity [References 2,3].

CRISPR RNA-guided diagnostics (CRISPR-dx) are a diverse group of nascent technologies that aim to address current limitations by providing a versatile and programmable platform that is sufficiently sensitive for clinical applications and stable enough for distribution [References 4,5]. The first CRISPR-based viral diagnostic came from Collins and colleagues in 2016, when they demonstrated that Cas9 could be used to discriminate between different variants of the Zika virus [Reference 6]. This approach relies on converting viral RNA to DNA using reverse transcriptase, followed by isothermal DNA amplification prior to sequence-based discrimination by Cas9. The exclusive recognition of double-stranded DNA (dsDNA) by Cas9 seemed to be an intrinsic limitation for diagnostic applications that require RNA detection. However, Beisel and colleagues recently developed a creative method that uses the trans-acting CRISPR-RNA (tracrRNA) to capture complementary RNA guides derived from RNA viruses [Reference 7]. In this system, the engineered tracrRNA-crRNA hybrid guides Cas9 to a complementarity dsDNA reporter. While this approach enables RNA detection, Cas9 is a single turn-over enzyme, which may limit sensitivity. In contrast to Cas9, target recognition by type V (Cas12-DETECTR) and type VI (Cas13-SHERLOCK) CRISPR-systems activates a multi-turnover non-sequence-specific "collateral nuclease" activity that amplifies the signal by cleaving thousands of reporter molecules for every target bound [References 8,9].

Like type VI, type III systems also recognize complementary RNA. However, unlike any other CRISPR system, target recognition by type III complexes simultaneously activates polymerase and HD-nuclease domains in the Cas10 subunit [References 10-12]. The polymerase domain has been estimated to generate ~1000 cyclic oligoadenylates per bound RNA [Reference 13], which trans-activate and allosterically regulate diverse multi-turnover ancillary nucleases that provide defense from invading genetic parasites [References 14,15]. This biochemical cascade exponentially amplifies the signal when type III complex detects target RNA, suggesting that these systems have the potential to enhance the sensitivity of CRISPR-based diagnostics. However, initial efforts to implement this approach failed to be sufficiently sensitive for clinical applications without prior amplification of the target RNA [References 16-18]. Part of what was limiting sensitivity in this first-generation diagnostic was the use of Csm6, an ancillary nuclease that also degrades the cyclic nucleotide activator [References 19-23].

Recently, Malcolm White's lab demonstrated that alternative ancillary nucleases, which efficiently cleave reporters but do not cleave the signaling molecule, can be used to enhance the sensitivity of type III-based diagnostics [Reference 24].

Despite innovations leading to new and improved CRISPR-based diagnostics, point-of-care testing requires new strategies that simplify the workflow and increase the sensitivity without prior RNA purification or amplification (e.g., PCR, LAMP, NASB, RPA, etc.). Here, we bring CRISPR-dx closer to a deployable diagnostic by developing a type III CRISPR-based method for sequence-specific capture and concentration of RNA from heterogeneous samples. To improve sensitivity, we purify several different ancillary nucleases (i.e., Can1, Can2, and NucC), systemically test nuclease activation using a series of cyclic oligoadenylates (i.e., cA3-cA6), test for ring nuclease activity and determine how cyclic oligoadenylates, as well as metal-preferences impact substrate cleavage activities. We show that the Can1 nuclease from $T.$ $thermophilus$ (TtCan1) and the Can2 ortholog from Archaeoglobi (AaCan2) are activated by more than one cyclic nucleotide species (i.e., cA3 and cA4) and that substrate specificity of these nucleases changes according to the bound activator. This observation helps explain how diverse cyclic nucleotides (i.e., cA3-cA6) produced by a single type III surveillance complex integrate distinct activities from a single effector. Finally, we demonstrate how the type III complex can be used to bypass RNA extraction methods, and that coupling type-III-based RNA capture with the AaCan2 nuclease further increases the sensitivity of SARS-CoV-2 RNA detection in patient swabs to $5 \times 10^4$ copies/ul.

FIG. 1A shows an example of Type III CRISPR-based RNA concentration and enhanced detection. Overview of two Csm-based RNA detection methods. In previous versions of the type III CRISPR-based diagnostic (T3D) (doi.org/10.1016/j.xcrm.2021.100319), 3 µL of total RNA is used as input for the reaction (left column). Here, we demonstrate that the type III CRISPR complex from $Thermus$ $thermophilus$ (e.g., TtCsm) can be used to pull-down and concentrate specific RNA targets from a complex mixture. His-tagged Csm complex is mixed with the extracted sample and incubated for 20 min at 60° C. for target RNA binding. The Histidine (His)-tagged complex is then isolated using Ni-NTA magnetic beads. The beads are concentrated using a magnet, and the supernatant is decanted. The pellet is then resuspended in a small volume of the reaction buffer containing ATP to activate polymerase activity of Cas10. Polymerization products (e.g., cA3 and cA4) activate ancillary nuclease (e.g., Csm6, NucC, Can, etc) that cleave a nucleic acid tether connecting a fluorophore and a quencher. Cleave of the tether releases a fluorescent signal.

Figure 1B:
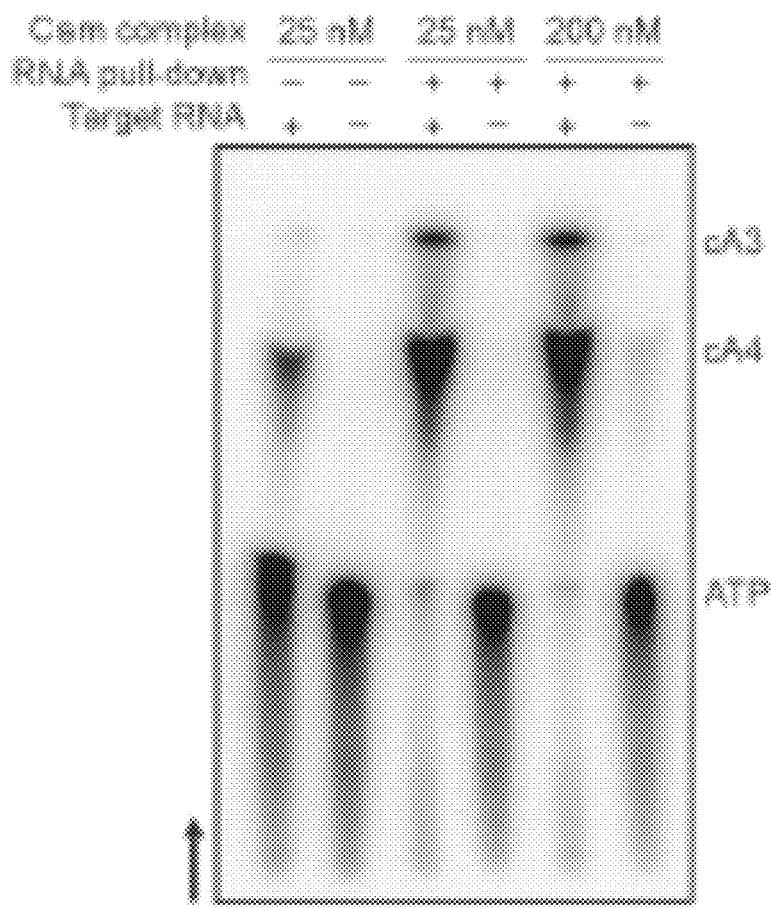
FIG. 1B shows an image of a thin-layer chromatography (TLC) plate illustrating Cas10-mediated polymerase activity measured using alpha-labeled P32 ATP.

FIG. 1B shows an image of a thin-layer chromatography (TLC) plate illustrating Cas10-mediated polymerase activity measured using alpha-labeled P32 ATP. Products of polymerization reaction are resolved using TLC. Black arrow shows migration of solvent in TLC plate. Csm concentration are shown across the top. The addition of 25 nM Csm followed by pulldown (lanes 3 and 4) results in a signal that is stronger than in standard T3D (left two lanes). Pulldown using 200 nM Csm also enhances the signal, but signal is also evident in the negative control, suggesting that 200 nM Csm is too high a reliable diagnostic under these reaction conditions.

Figure 1C:
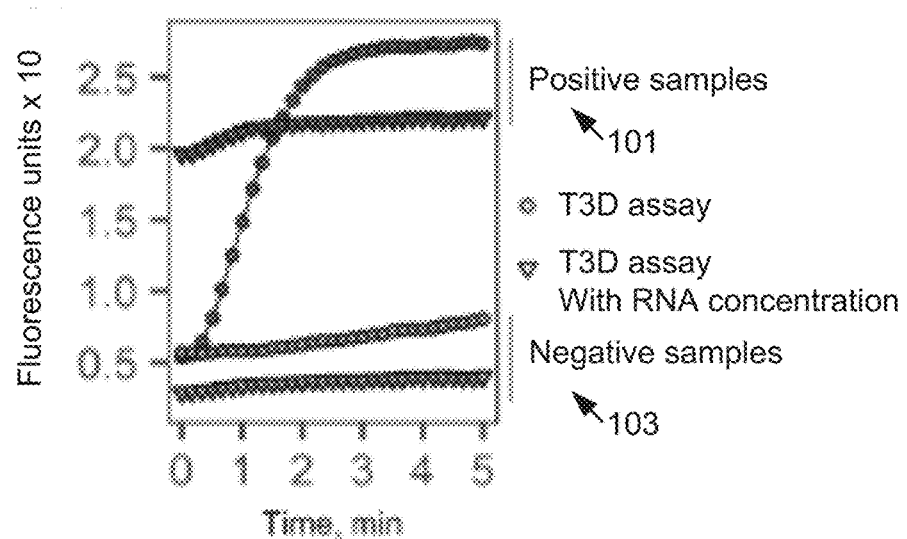
FIG. 1C shows a plot comparing two Csm-based RNA detection methods (T3D and T3D with type-III concentration) using a fluorescent detection assay.

FIG. 1C shows a plot comparing two Csm-based RNA detection methods (T3D and T3D with type-III concentration) using a fluorescent detection assay. Fluorescence (y-axis) was measured over time (x-axis) using QuantStudio 3 qPCR instrument. Human RNA (100 ng/µL) mixed with 2 nM target RNA (i.e., SARS-CoV-2 N gene RNA) (101) or human RNA only (103) were used for the assay. In T3D reaction that do not include type-III concentration (circles), 3 µL of RNA were combined with 25 nM TthCsm complex, ATP and ancillary nuclease in a reaction buffer. Binding to the target (N gene) stimulates polymerization of cyclic oligoadenylates (e.g., cA3 and cA4) that activate the ancillary nuclease, which cleaves reporter and releases a fluorophore. In T3D assay with type-III concentration (T3C) (triangles), 120 µL of RNA sample were mixed with 25 nM TthCsm complex and concentrated with beads. Concentrated beads were resuspended in 30 µL of polymerization buffer with ATP. Polymerization products were combined with ancillary nuclease and fluorescent reporter and imaged. T3D assay with pulldown had high fluorescence levels at 0 min, suggesting that most of the reporter was cleaved before first fluorescence reading (10 sec).

FIG. 2A shows a phylogeny of thermostable NucC proteins. NucC homologs were identified by Lau et al., were used to query the non-redundant database at NCBI. This resulted in a list of 685 putative NucC homologs. Nine of the 685 sequences were derived from organisms with optimal growth temperatures between 45 and 60° C. The new thermal stable sequences were then aligned with NucC protein sequences reported previously by Lau et al. The alignment was used to generate a NucC phylogeny and the resides involved in either cA3 binding, gate loop formation, and the nuclease active site are shown next to each branch. We picked three thermostable NucC homologs for expression and purification in E. coli.

FIG. 2B shows size exclusion chromatography (SEC) profiles for NucC proteins derived from Elioraea sp. Yellowstone (WP_141855040.1), Clostridium tepidum (WP_195923598.1) and Acidimicrobiales bacterium mtb01 (TEX45487.1). NucC homologs from Clostridium tepidum and Acidimicrobiales bacterium mtb01 elute with retention times consistent with trimer formation, while a smaller fraction of these proteins are monomeric in solution. In contrast, the NucC protein from Elioraea sp. Yellowstone purified mostly as monomer, while we observed small peak for the trimer.

FIG. 2C shows an SDS-PAGE of purified trimeric NucC homologs. Expected band size for was 27 kda for both Elioraea sp. Yellowstone and Acidimicrobiales bacterium mtb01 NucC, while NucC from Clostridium tepidum is expected to be slightly larger (29 kda).

Figure 3A:
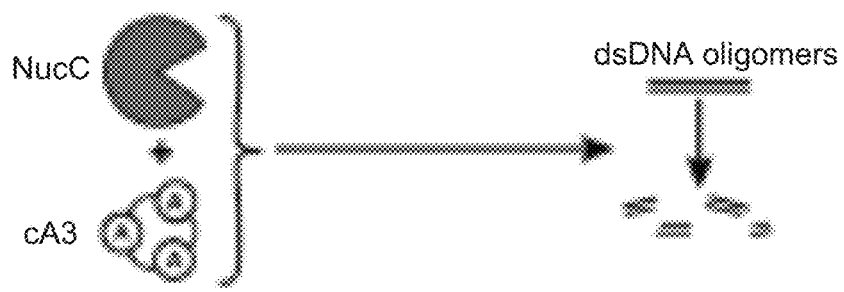
FIG. 3A shows a schematic of thermostable NucC variants degrading DNA substrates larger than 30 bp.

FIG. 3A shows a schematic of thermostable NucC variants degrading DNA substrates larger than 30 bp. An assay was performed to test degradation of short dsDNA oligomers by NucC in presence of cA3.

Figure 3B:
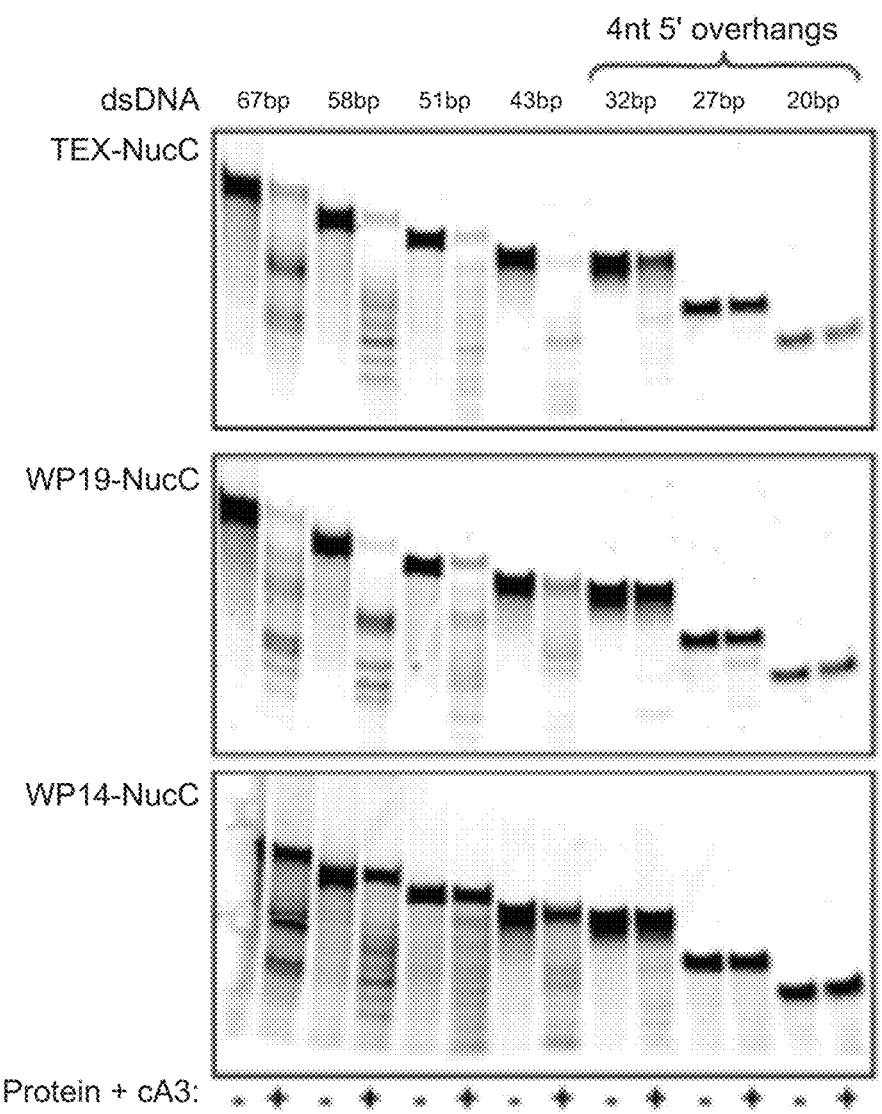
FIG. 3B shows an image of denaturing urea polyacrylamide gel showing NucC variants preferentially cleave dsDNA substrates larger than 30 bp in the presence of cA3.

FIG. 3B shows an image of denaturing urea polyacrylamide gel showing NucC variants preferentially cleave dsDNA substrates larger than 30 bp in the presence of cA3. TEX-NucC appears to be the most active variant, and cleaves the 43 bp substrate relatively efficiently. 10 µL, reactions contained 300 nM NucC variant, 4.5-12.6 µM dsDNA oligomers, 200 nM cA3 and were incubated at 40° C. for 30 minutes, and were analyzed on a denaturing urea polyacrylamide gel stained with SYBR gold.

FIG. 4A shows a schematic of an example of a type III-CRISPR surveillance complex coupled with NucC and Can DNases for detection of SARS-CoV-2 RNA. TtCsm binding of SARS-CoV-2 RNA allosterically activates Cas10 to polymerize ATP into cyclic oligoadenylates (cA2-cA6). cA3 and cA4 are the main products, as determined by mass spec. cA3 activates the DNase TexNucC, and cA4 activates the DNase TthCan. Neither TexNucC or TthCan are expected to cleave the activating cAx ligands via ring nuclease activity or via their DNase domains, thereby preserving the signals generated by the TtCsm complex.

FIG. 4B shows a schematic of activated TexNucC and TthCan DNases cleavage of a fluorescent DNA reporter (43 bp dsDNA) with an internal fluorophore (fluorescein) and a 3' terminal quencher (BHQ-1), to produce a fluorescent signal. FIG. 4C shows a schematic of activated TexNucC and TthCan DNase cleavage of a 1-3 Kb dsDNA substrate tagged with biotin at one 5' end and digoxigenin at the other 5' end. A sample negative for SARS-CoV-2 leaves the tagged dsDNA substrate intact, which causes accumulation of streptavidin-tagged gold nanoparticles (purple) at the anti-digoxigenin line of a lateral flow strip. Whereas a sample positive for SARS-CoV-2 degrades the dsDNA that tethers biotin to digoxigenin, which causes the disappearance of a purple line at the anti-digoxigenin line. An internal-control, anti-streptavidin line at the top of the lateral flow strip still appears.

FIGS. 1-4 and their sub-parts show that type III CRISPR systems may be repurposed to isolate and concentrate RNAs that contain sequences complementary to the guide. Although specific nucleic acids such as SARS-CoV-2 RNA is illustrated in the foregoing figures and throughout this disclosure, other types of nucleic acids may be similarity isolated and concentrated. Furthermore, other RNA-guided RNA binding proteins may be repurposed in similar ways. Isolation and concentration of specific RNA will be a valuable for many applications and we have demonstrated that this approach significantly increases diagnostic sensitivity. The disclosure also shows that NucC nuclease cleaves dsDNA substrates that are longer than 30 bps. This nuclease and those with similar activities (such as Can nucleases like Can1) may be repurposed to exploit the full repertoire of products generated by the Cas10 polymerase and that the integration of these enzymes will further improve sensitivity of nucleic acid detection methods.

FIG. 5A shows a schematic of an example of type III CRISPR-based RNA concentration. Schematic of Type III CRISPR-based RNA concentration. RNase-dead Type III CRISPR complex from Thermus thermophilus (e.g., TtCsm$^{Csm3-D34A}$) is added to a sample to bind complementary target RNA. The His-tagged complex is concentrated using nickel-derivatized magnetic beads and a magnet.

FIG. 5B shows an image of a UREA-PAGE for target and non-target RNA. RNA enrichment with TtCsm$^{Csm3-D34A}$ complex was tested using 25 nM P32 5'-end labeled RNA. Target and non-target RNA fragments were mixed with 125 nM TtCsm$^{Csm3-D34A}$ complex, incubated at 65° C. for 20 min prior to concentration of the His-tagged complex with nickel-derivatized magnetic beads. After the pull-down, RNAs phenol-chloroform extracted from supernatants and the Csm-beads were resolved using UREA-PAGE.

FIG. 5C Csm-based direct RNA detection using 3 µL of sample is compared to an assay with additional RNA capture and concentration step. Magnetic beads decorated with TtCsmCsm3-D34A are added to the sample. After concentrating beads with a magnet, the supernatant is decanted. The pellet is then resuspended in a small volume of the reaction buffer containing ATP to activate polymerase activity of Cas10. Polymerization products (e.g., cA3 and cA4) are used for the downstream detection assays.

FIG. 5D shows an image of a TLC plate comparing results with and without RNA capture. TtCsm$^{Csm3-D34A}$ polymerization reactions were performed with $\alpha$-$^{32}$P-ATP as shown in FIG. 5C and products were resolved using thin-layer chromatography (TLC). Black arrow shows migration of solvent in the TLC plate. Bands were annotated using chemically synthesized standards, examples of which are shown in FIG. 15D. 3 µL (−RNA capture) or 120 µL (+RNA capture) of SARS-CoV-2 N-gene RNA ($10^{10}$ copies/µL) diluted in total human RNA (293T cells) were used for reactions.

FIG. 5E shows a plot of TtCsm6-based fluorescent readout (top panel) is used to sense cA4 generated by TtCsm$^{Csm3-D34A}$ with (red bars) or without RNA capture step (blue bars) as shown in FIG. 5C. SARS-CoV-2 N-gene RNA diluted in total human RNA (HEK293T cells) was used as a target. Fluorescence was measured with qPCR instrument and normalized to the no target control (NTC, 293T RNA only). In each assay, means (n=3) were compared with one-way ANOVA. Pairwise comparisons between target RNA dilutions and NTC were performed using post hoc Dunnett's test. Data are shown as mean±SD. *$p<0.05$; $p<0.005$; *$p<0.001$; ****$p<0.0001$ Can1 and Can2 ancillary nucleases demonstrate different substrate specificity depending on the activator.

Figure 6A:
FIG. 6A shows a schematic of a domain organization of Can1 and Can2 proteins.

FIG. 6A shows a schematic of a domain organization of Can1 and Can2 proteins. Can2 proteins have two domains—CARF and PD-(D/E)XK superfamily nuclease domain.

Can1 is predicted to derive from Can2 by gene duplication [Reference 30]. In FIG. 6A, NLD stands for nuclease-like domain.

Figure 6B:
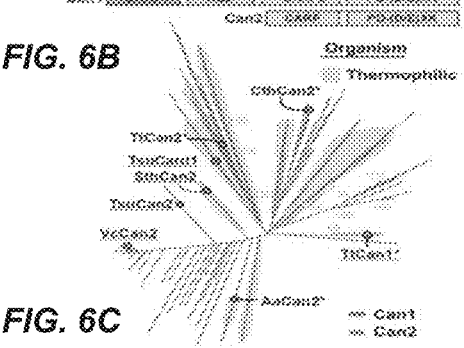
FIG. 6B shows a schematic of a maximum-likelihood phylogeny of 204 Can1 (CARF2 nuclease and PD-(D/E)XK domain) and 2,121 Can2 proteins.

FIG. 6B shows a schematic of a maximum-likelihood phylogeny of 204 Can1 (CARF2 nuclease and PD-(D/E)XK domain) and 2,121 Can2 proteins. Previously studied effectors are underlined on the tree. Effectors annotated with a "*" are chosen for purification and in vitro experiments.

Figure 6C:
FIG. 6C shows an example results of Plasmid (15 nM), ssRNA (425 nM), and ssDNA (425 nM) cleavage assay with TtCan1 (200 nM) in the presence of cA3 or cA4 (20 nM).

FIG. 6C shows an example results of Plasmid (15 nM), ssRNA (425 nM), and ssDNA (425 nM) cleavage assay with TtCan1 (200 nM) in the presence of cA3 or cA4 (20 nM). The reactions were incubated 15 min at 60° C.

Figure 6D:
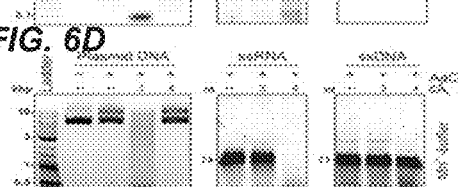
FIG. 6D shows an example of results of cleavage assays with AaCan2 (200 nM) in the presence cA4 or cA3 (20 nM).

FIG. 6D shows an example of results of cleavage assays with AaCan2 (200 nM) in the presence cA4 or cA3 (20 nM). Assays were performed with 15 nM plasmid DNA (left), 425 nM ssRNA or ssDNA (right) for 15 min at 55° C.

Figure 6E:
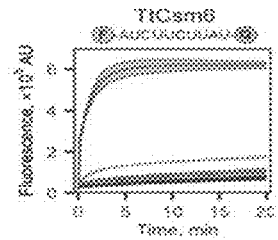
FIG. 6E shows plots of results of TtCsm6 (300 nM) and AaCan2 (300 nM) cleavage assays.

FIG. 6E shows plots of results of TtCsm6 (300 nM) and AaCan2 (300 nM) cleavage assays. Assays were performed with fluorescent ssRNA reporter (top) in the presence of varying cA4 activator concentrations (as shown in the sidebar). Data is shown as mean (center line) of three replicates ±sd (ribbon). Optimal fluorescent reporter (top) was determined using RNA library screen, an example of which is show in FIG. 12.

Figure 6F:
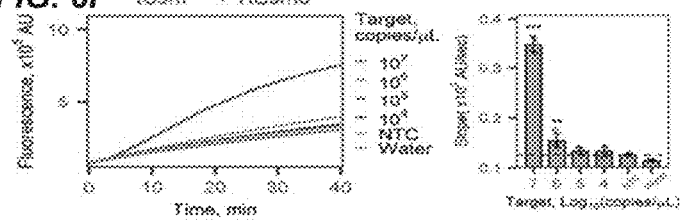
FIG. 6F shows plots of TtCsm RNA detection assays coupled with TtCsm6.

FIG. 6F shows plots of TtCsm RNA detection assays coupled with TtCsm6. TtCsm6-based readouts were performed using samples with target RNA concentration ranging from $10^7$ to $10^2$ copies/μL.

Figure 6G:
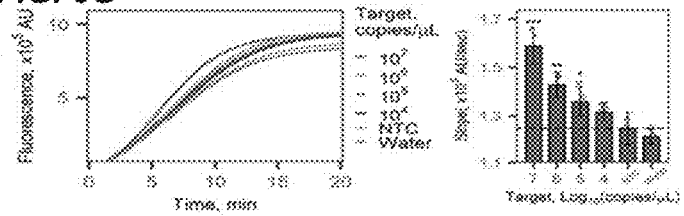
FIG. 6G shows plots of TtCsm RNA detection assays coupled with AaCan2.

FIG. 6G shows plots of TtCsm RNA detection assays coupled with AaCan2. AaCan2-based readouts were performed using samples with target RNA concentration ranging from $10^7$ to $10^2$ copies/μL.

Referring to both FIGS. 6F and 6G, samples were prepared by spiking IVT fragment of SARS-CoV-2 N gene in total RNA extracted from nasopharyngeal swab patient sample negative for SARS-CoV-2. Cleavage of fluorescent RNA reporter was detected by measuring fluorescence every 10 sec in a real-time PCR instrument (left). Data were plotted as mean of 4 replicates. Simple linear regression was used to calculate slopes for linear regions of the curves. Bars show mean values (n=4)±sem (right). Data was analyzed with one-way ANOVA followed by multiple comparisons to NTC sample using one-tailed post-hoc Dunnett's test. * $p<0.001$;  $p<0.01$; * $p<0.05$ Incorporation of cA3-Activated Nucleases into a Csm-Based RNA Detection Assay.

FIG. 7A shows a schematic illustrating that target bound TtCsm complex generates cA3 and cA4 (primary product). The schematics summarize cA3- and cA4-dependent activities of CARF-nucleases biochemically tested in this study. N/D—not detected; Asterisk (*) indicates nucleases that were tested against RNA reporter library (an example of which is shown in FIG. 12) and displayed preference for specific sequences.

FIG. 7B shows cleavage results of CtNucC. Left panel: CtNucC (15 nM) is activated by cA3 (20 nM) and cleaves plasmid DNA into short fragments in 15 min. Right panel: The deep sequencing of DNA fragments generated after 5 min of incubation with CtNucC revealed the preferential cleavage sites (ANNT). The pattern in the sequencing depth support the model where CtNucC cleaves DNA with dinucleotide 3'-overhangs.

FIG. 7C shows plots of CtNucC (300 nM), TtCan1 (300 nM) and AaCan2 (300 nM) cleavage assays with fluorescent dsDNA reporter in the presence of varying cA3 activator concentrations. Different concentrations are shown. Data is shown as mean (center line) of three replicates±sem (ribbon).

FIG. 7D shows plots of TtCsm RNA detection assays coupled with AaCan2 (ssRNA reporter), CtNucC (dsDNA reporter) and combination of AaCan2 and CtNucC (both reporters). Reactions were performed using samples with target RNA concentration ranging from $10^7$ to $10^2$ copies/μL. Samples were prepared by spiking IVT fragment of SARS-CoV-2 N gene in total RNA of SARS-CoV-2 negative nasal swab. Cleavage of the fluorescent reporter was detected by measuring fluorescence every 10 sec in a real-time PCR instrument. Simple linear regression was used to determine slopes for 3 replicates. See FIG. 16 for fluorescent curves used in the analysis. Data were plotted as mean (n=3)±sd and analyzed with one-way ANOVA. All samples were compared to the non-target RNA control (NTC) using one-tailed post-hoc Dunnett's test. * $p<0.001$;  $p<0.01$; * $p<0.05$.

TtCsm-Based RNA Capture Directly Detects SARS-CoV-2 in Clinical Samples

FIG. 8A shows plots of positive SARS-CoV-2 and negative RNA samples tested with TtCsm-AaCan2 detection assay with and without upstream RNA capture step. Seventeen SARS-CoV-2 positive (801) and six negative (803) RNA samples were tested with TtCsm-AaCan2 detection assay with and without upstream RNA capture step.

Vertical dotted lines show timepoints that were used to analyze type III detection results. Error bars show detection threshold set as mean (n=6) of negative samples±2.33 SD (p-value<0.01). Samples with fluorescence higher than upper boundary of this interval were considered positive in type III detection assay.

FIG. 8B shows a scatter plot of a distribution of Ct values (N1 CDC primers) of RNA samples tested in FIG. 8A. Unfilled circles represent samples that tested positive in type III detection, filled circles represent samples that tested negative.

FIG. 8C shows a schematic of an example of a TtCsm-based RNA capture assay from a nasopharyngeal swab coupled with AaCan2-based fluorescent detection.

FIG. 8D shows a plot of nasopharyngeal swab sample positive for SARS-CoV-2 with RT-qPCR (Ct=13.6) used to make 10-fold serial dilutions in a negative nasopharyngeal swab (Ct>40). A total of 120 μL of the sample was used for direct detection with TtCsm-based RNA capture assay depicted in FIG. 8C. Bars show mean values (n=3)±sem of the slopes calculated with simple linear regression of fluorescent readings measured every 10 seconds within the first 5 minutes of the experiment (FIG. 17C). All slopes were compared to the negative control (NTC) with one-way ANOVA and post-hoc one-tailed Dunnett's test. * $p<0.001$;  $p<0.01$; * $p<0.05$.

Detection of Small RNAs (miRNA, siRNA, piRNA, Etc.)

MicroRNAs (miRNAs) are important early biomarkers of cancer, glaucoma and infectious diseases [References 7-10]. However, the small size (~22 nucleotides) and sequence homology (e.g. single-nucleotide variation) of these biomarkers makes them difficult to detect using traditional PCR, Cas13 or isothermal amplification methods [References 11-13]. Small type III surveillance complexes can be produced with guide RNAs that are shorter (i.e., 20-30 nts) than the median size of spacers sequences typically seen in type III CRISPR systems (~40 bp) (as shown in FIG. 3B), to enable facile, sensitive and specific detection of small RNA biomarkers critical to human health. Type III CRISPR concentration followed by buffer exchange is expected to enable testing for small RNA biomarkers directly from complex patient samples (i.e., saliva, urine, blood) that typically require upstream purification before similar diagnostic tests (i.e., PCR).

FIG. 9A shows a schematic of TtCsm-complex bound to a Ni-NTA magnetic bead and an image of an SDS-PAGE of TtCsm complex after pull-down with NI-NTA magnetic beads. After binding, beads were separated with a magnet, and supernatant ("Super") was decanted. The beads were washed once ("Wash"), and the protein was eluted using 250 mM imidazole ("Elution").

FIG. 9B shows results of sequence-specific RNA enrichment with TtCsm$^{Csm3-D34A}$ complex tested using P32 5'-end labeled in vitro transcribed (IVT) RNA fragments. Target and non-target RNA fragments were mixed with TtCsm$^{dead}$ complex, incubated at 65° C. for 20 min and pulled-down using a Ni-NTA magnetic beads. After the magnetic pull-down, RNA was phenol-chloroform extracted from supernatants ("Free") and bead pellets ("Bound"). Extracted RNA was resolved using UREA-PAGE, exposed to a phosphor screen, and imaged on Typhoon imager (Amersham). Three replicates are shown.

FIG. 9C shows a plot of RNA bands shown in FIG. B quantified using ImageJ. The bound fraction was calculated for each replicate as follows: [bound/(bound+free)*100%]. Bars show mean of 3 replicates±SEM.

FIG. 9D shows an image of a TLC plate of TtCsm$^{Csm3-D34A}$-complex products, including cA3 and cA4. TtCsm$^{Csm3-D34A}$ complex (25 nM) was mixed with target RNA (10$^{11}$ copies/ul) to activate Cas10 subunit. Polymerization reaction was performed with α-$^{32}$P-ATP. Reaction products were phenol-chloroform extracted and resolved on the same thin-layer chromatography (TLC) plate with chemically synthesized standards. Radiolabeled products (left) were imaged with Typhoon phosphor imager. Chemically synthesized standards (cA2-cA6) were visualized using UV shadowing (right).

Figure 10A:
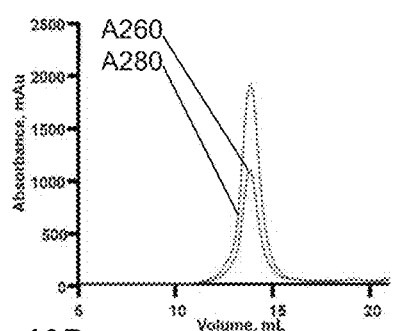
FIG. 10A shows a size-exclusion chromatography (SEC) profile of purified TtCan1 protein.

Purification and Biochemical Characterization of *Thermus thermophilus* Can1 (TtCan1) Nuclease Activities FIG. 10A shows a size-exclusion chromatography (SEC) profile of purified TtCan1 protein. SEC was performed using a Sepharose 200 Increase 10/300 GL size-exclusion column (Cytiva).

Figure 10B:
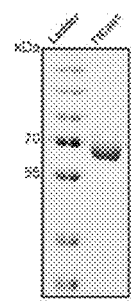
FIG. 10B shows an example of SDS-PAGE of purified TtCan1.

FIG. 10B shows an example of SDS-PAGE of purified TtCan1. Expected size is 71 kDa.

Figure 10C:
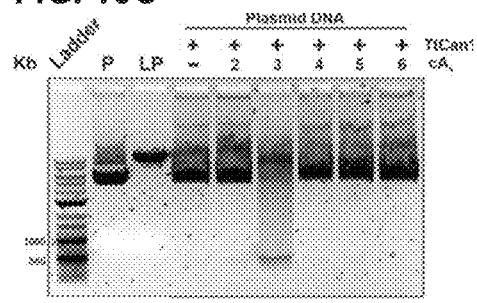
FIG. 10C shows an example of plasmid digestion with TtCan1 in the presence of cyclic oligoadenylates with 2-6 bases (cA2-cA6, 45 nM) at 60° C., 5 min incubation.

FIG. 10C shows an example of plasmid (1 ug) digestion with TtCan1 (200 nM) in the presence of cyclic oligoadenylates with 2-6 bases (cA2-cA6, 45 nM) at 60° C., 5 min incubation.

Figure 10D:
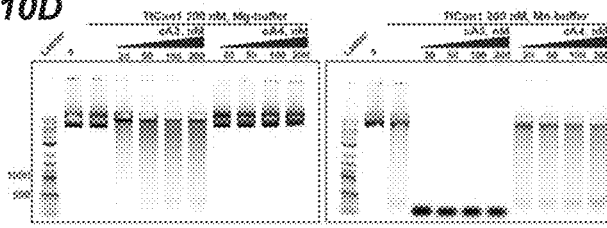
FIG. 10D shows an example of plasmid digestion with TtCan1 in the presence of two different metal ions.

FIG. 10D shows an example of plasmid (1 ug) digestion with TtCan1 in the presence of two different metal ions (Mg$^{2+}$ or Mn$^{2+}$) at 60° C., 15 min incubation.

Figure 10E:
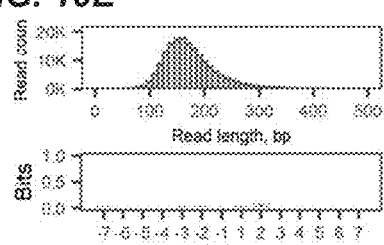
FIG. 10E shows an example of digested plasmid DNA fragments shown in FIG. 10D (cA3 activator) were prepped and sequenced with Oxford Nanopore.

FIG. 10E shows an example of digested plasmid DNA fragments shown in FIG. 10D (cA3 activator) were prepped and sequenced with Oxford Nanopore. Top panel: read size distribution. Bottom: web logos were generated by aligning sequences surrounding 5'- and 3'-ends of reads (i.e., cut sites) f FIG. 10F shows testing ssDNA and ssRNA nuclease activities of TtCan1 (200 nM) in the presence of cyclic oligoadenylates with 2-6 bases (cA2-cA6, 45 nM) and in buffers having Mn$^{2+}$.

Figures 10F, 10G:
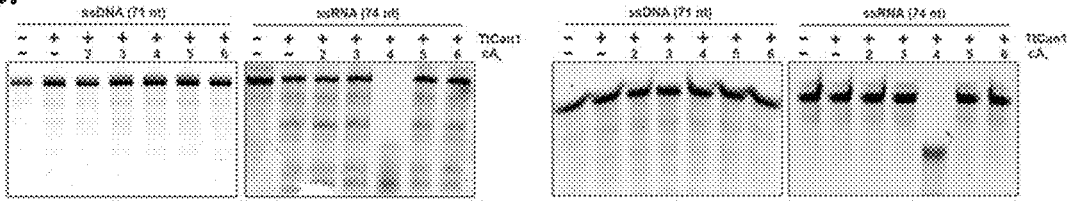
FIG. 10F shows testing ssDNA and ssRNA nuclease activities of TtCan1 in the presence of cyclic oligoadenylates with 2-6 bases (cA2-cA6, 45 nM) and in buffers having $Mn^{2+}$.
FIG. 10G shows testing ssDNA and ssRNA nuclease activities of TtCan1 in the presence of cyclic oligoadenylates with 2-6 bases (cA2-cA6, 45 nM) and in buffers having $Mg^{2+}$.

FIG. 10G shows testing ssDNA and ssRNA nuclease activities of TtCan1 (200 nM) in the presence of cyclic oligoadenylates with 2-6 bases (cA2-cA6, 45 nM) and in buffers having Mg$^{2+}$. Referring to both FIGS. 10F and 10G, the reactions were performed at 60° C. for 15 minutes.

Figure 10H:
FIG. 10H shows an example of results of cA3 and cA4 hydrolysis by TtCsm6 and TtCan1.

FIG. 10H shows an example of results of cA3 and cA4 hydrolysis by TtCsm6 and TtCan1. α-$^{32}$P-labeled cA3 and cA4 were produced using TtCsm$^{dead}$ complex in the presence of target RNA and phenol-chloroform extracted. Radiolabeled cA3 and cA4 were mixed with nucleases (500 nM) and incubated for 1 hour at 55° C. Reaction products were phenol-chloroform extracted and resolved using thin-layer chromatography (TLC).

Purification and Biochemical Characterization of Archaeoglobi Archaeon JdFR-42 Can2 (AaCan2) Nuclease Activities.

Figure 11A:
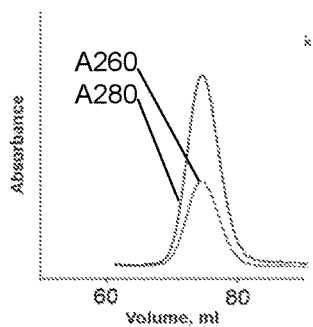
FIG. 11A shows a size-exclusion chromatography (SEC) profile of purified AaCan2 protein.

FIG. 11A shows a size-exclusion chromatography (SEC) profile of purified AaCan2 protein. SEC was performed using a Sepharose 200 Increase 10/300 GL size-exclusion column (Cytiva).

Figure 11B:
FIG. 11B shows an image of an SDS-PAGE of purified AaCan2.

FIG. 11B shows an image of an SDS-PAGE of purified AaCan2. Expected size is 42.8 kDa.

Figure 11C:
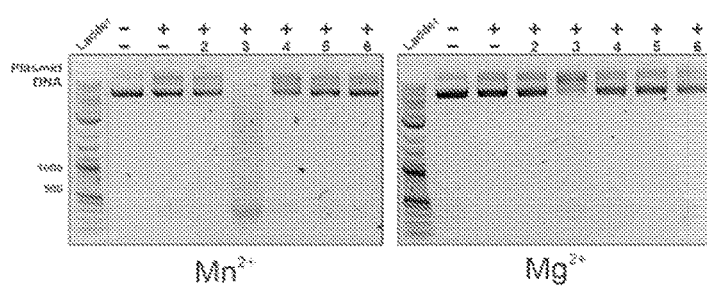
FIG. 11C shows results of cleavage assays with AaCan2 (200 nM) in in the presence cyclic oligoadenylates with 2-6 bases (cA2-cA6, 45 nM) and in a buffer having $Mn^{2+}$.

FIG. 11C shows results of cleavage assays with AaCan2 (200 nM) in in the presence cyclic oligoadenylates with 2-6 bases (cA2-cA6, 45 nM) and in a buffer having Mn$^{2+}$.

FIG. 11D shows results of cleavage assays with AaCan2 (200 nM) in in the presence cyclic oligoadenylates with 2-6 bases (cA2-cA6, 45 nM) and in a buffer having Mg$^{2+}$.

Referring to both FIGS. 11C and 11D, assays were performed with 425 nM ssRNA or ssDNA, 15 nM plasmid DNA for 15 min at 55° C.

Figure 11E:
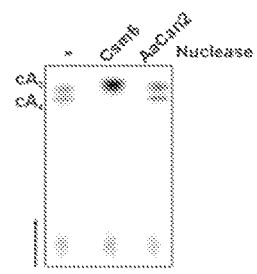
FIG. 11E shows results of cA3 and cA4 hydrolysis by TtCsm6 and AaCan2.

FIG. 11E shows results of cA3 and cA4 hydrolysis by TtCsm6 and AaCan2. The assay was performed as described in FIG. 10H.

Figure 12A:
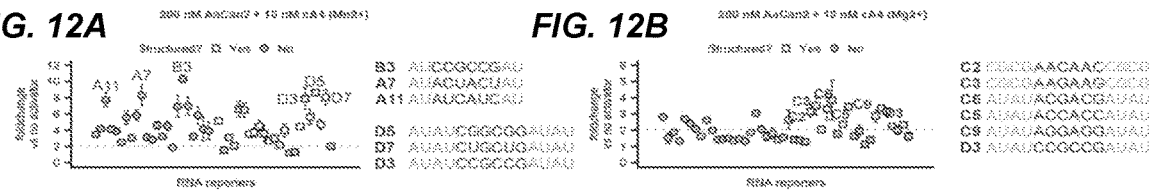
FIG. 12A shows a plot of a library of 46 synthetic RNAs tethered to a 5'fluorophore and 3'quencher screened with AaCan2 in the presence of cA4 in a buffer having $Mn^{2+}$.
Figure 12B:
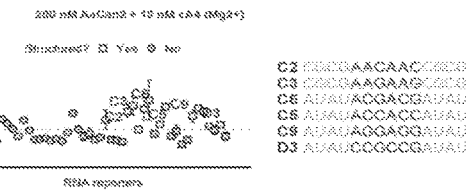
FIG. 12B shows a plot of a library of 46 synthetic RNAs tethered to a 5'fluorophore and 3'quencher screened with AaCan2 in the presence of cA4 in a buffer having $Mg^{2+}$.

Screening a library of synthetic RNA reporters reveals sequence cleavage preference for AaCan2 and TtCan1. FIG. 12A shows a plot of a library of 46 synthetic RNAs tethered to a 5'fluorophore and 3'quencher screened with AaCan2 in the presence of cA4 in a buffer having Mn$^{2+}$. FIG. 12B shows a plot of a library of 46 synthetic RNAs tethered to a 5'fluorophore and 3'quencher screened with AaCan2 in the presence of cA4 in a buffer having Mg$^{2+}$ FIG. 12C shows a plot of a library of 46 synthetic RNAs tethered to a 5' fluorophore and 3' quencher screened with TtCan1 in the presence of cA4.

Figure 12C:
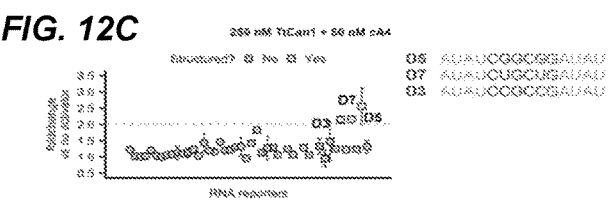
FIG. 12C shows a plot of a library of 46 synthetic RNAs tethered to a 5'fluorophore and 3'quencher screened with TtCan1 in the presence of cA4.

Referring to FIGS. 12A-C, reactions were incubated at 55° C. (AaCan2) or 60° C. (TtCan1) in a qPCR instrument with fluorescent readings taken every 10 seconds. Fluorescence at 10 minute incubation time was normalized to the no activator control. Data are shown as mean±SD (n=3).

Nucleases AaCan2, TtCsm6 and TtCan1 Demonstrate Different Sensitivity to cA4.

Figure 13:
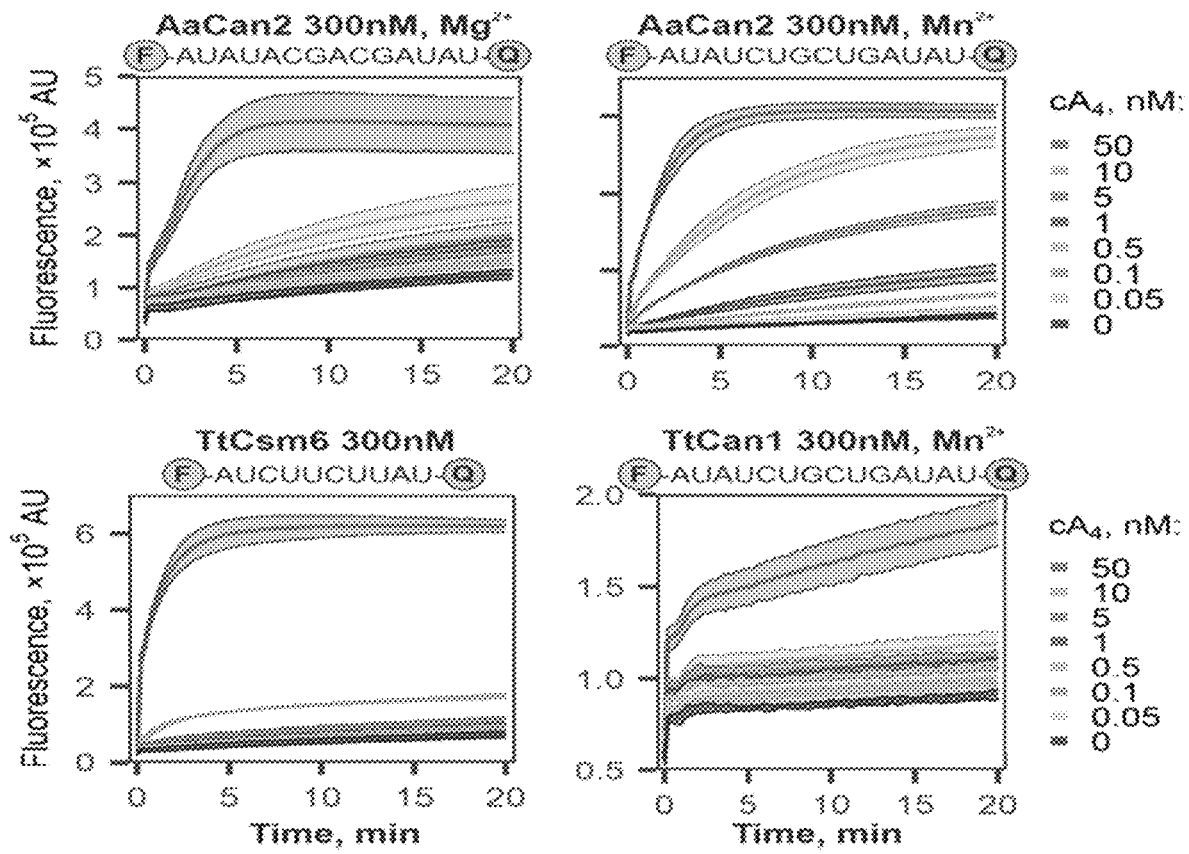
FIG. 13 shows results of AaCan2, TtCsm6 and TtCan1 cleavage assays with fluorescent ssRNA reporter in the presence of varying cA4 activator concentrations.

FIG. 13 shows results of AaCan2 (300 nM), TtCsm6 (300 nM) and TtCan1 (300 nM) cleavage assays with fluorescent ssRNA reporter (300 nM) in the presence of varying cA4 activator concentrations. (shown with different shading). Data is shown as mean (center line) of three replicates±SD (ribbon). Optimal fluorescent reporters (top) were identified using RNA library screen shown in the FIG. 12.

Purification and Biochemical Characterization of Thermostable NucC Orthologs

FIG. 14A shows an example of a maximum-likelihood phylogeny of NucC orthologs. Previously studied effectors are underlined on the tree. Effectors labeled with an asterisk (*) are chosen for purification and in vitro experiments.

FIG. 14B shows size-exclusion chromatography (SEC) profiles of purified NucC orthologs. SEC was performed using a Sepharose 200 Increase 10/300 GL size-exclusion column (Cytiva).

FIG. 14C shows an example of SDS-PAGE of purified NucC orthologs. Expected size of EsNucC, CtNucC and Amtb01NucC are ~27.5 kDA, ~29 kDa and ~27.4 kDa, respectively.

FIG. 14D shows an example of plasmid (Addgene #105621, 1 ug) digestion with thermostable NucC orthologs (45 nM) in the presence of cyclic oligoadenylates with 2-6 bases (cA2-cA6, 45 nM). L—DNA ladder, P—Plasmid DNA.

FIG. 14E shows DNase activity of NucC orthologs was tested across a temperature range (45-60° C.). The plasmid (1 ug) was mixed with 45 nM EsNucC+45 nM cA3, 15 nM CtNucC+15 nM cA3 or 45 nM Amtb01NucC+45 nM cA3 for 15 min. P—Plasmid DNA.

FIG. 14F shows cA3 and cA4 hydrolysis by EsNucC, CtNucC and Amtb01NucC. The assay was performed as described in FIG. 10H.

Thermostable NucC homologs Amtb01NucC, EsNucC, and CtNucC demonstrate sequence cleavage preference of plasmid DNA FIG. 15A shows an example of a time-course plasmid (Addgene #105621) digestion with thermostable NucC homologs in the presence of cA3. The plasmid (1 ug) was mixed with EsNucC (45 nM)+cA3 (45 nM), CtNucC (15 nM)+cA3 (15 nM) or Amtb01NucC (45 nM)+cA3 (45 nM) for different periods of time.

FIG. 15B shows an example of plasmid DNA cleavage fragments shown in a were end-prepped and deep-sequenced using Oxford Nanopore. Plots show distribution of the read length generated from fragments after different digestion times.

FIG. 15C shows an example of cleavage maps for nucleases. Position of read ends (cut sites) were identified and counted to generate cleavage maps for each nuclease. Resulting maps show cut sites at the longest incubation time tested:15 minutes of digestion with Amtb01NucC and CtNucC, and after one hour—with EsNucC.

FIG. 15D shows an example of sequence logos. Seven nucleotide sequences from both ends of the 5% most frequently cut sites were extracted and used to generate the sequence logos. Resulting sequence logos indicate enrichment for A at −1 position (nucleotide 6) and T at +1 position (nucleotide 9).

FIG. 15E shows a plot of sequencing depth at cut sites. Sequences of top cleaved site are shown for each nuclease. Sequencing depth shows a pattern (i.e., reduced sequencing depth at cut site) which is consistent with 3'-end overhang removal during end-prep step with T4 DNA polymerase when sequencing libraries were prepared.

Integration of cA3-Activated Nucleases into Csm-Based RNA Detection Assay.

Figure 16A:
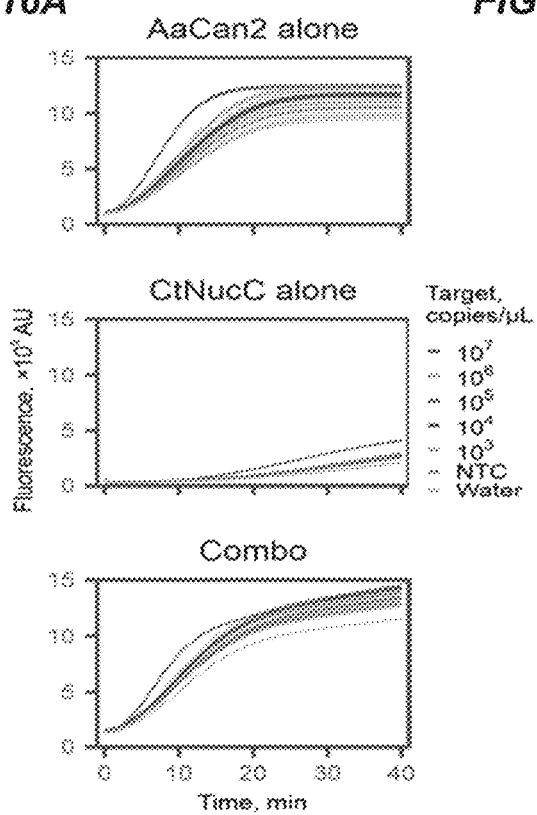
FIG. 16A shows a plot of TtCsm RNA detection assays coupled with AaCan2 (ssRNA reporter), CtNuCC (dsDNA reporter) and combination of AaCan2 and CtNucC (both reporters).

FIG. 16A shows a plot of TtCsm RNA detection assays coupled with AaCan2 (ssRNA reporter), CtNucC (dsDNA reporter) and combination of AaCan2 and CtNucC (both reporters). Reactions were performed using samples with target RNA concentration ranging from $10^7$ to $10^2$ copies/μL. Samples were prepared by spiking IVT fragment of SARS-CoV-2 N gene in total RNA of SARS-CoV-2 negative nasal swab. Cleavage of the fluorescent reporter was detected by measuring fluorescence every 10 sec in a real-time PCR instrument. Data is shown as mean (center line) of three replicates±sd (ribbon).

Figure 16B:
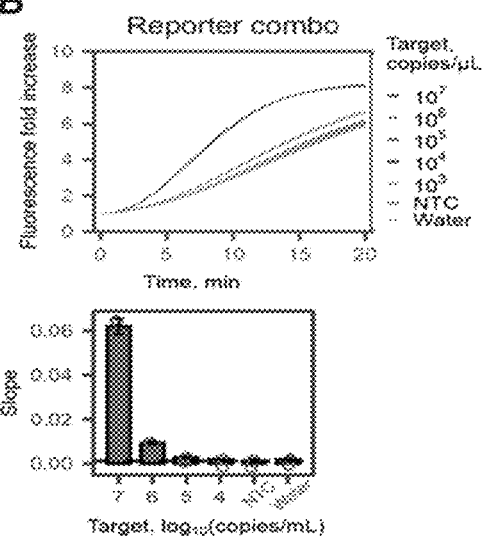
FIG. 16B shows a plot of TtCsm RNA detection assays coupled with AaCan2 and two reporters (ssRNA and dsDNA).

FIG. 16B shows a plot of TtCsm RNA detection assays coupled with AaCan2 and two reporters (ssRNA and dsDNA). The assay was performed as described in FIG. 15A.

TtCsm-Based RNA Capture Assay Directly Detects SARS-CoV-2 in Clinical Patient Samples FIG. 17A shows a Violin plot of a distribution of Ct values in 858 RNA samples collected and tested with RT-qPCR (N1 diagnostic primers, CDC) over the period from January to December of 2021. A subset of RNA samples (blue dots) was used to validate Csm-based direct RNA capture and detection.

FIG. 17B shows a plot of results of RNA samples that were tested with qRT-PCR (x-axis) and TtCsm-based detection assay (y-axis) with and without upstream RNA capture step. RNA samples with Ct values <40 were considered positive for SARS-CoV-2. Single technical replicates are shown for qRT-PCR and TtCsm-based detection assay. Z-scores were calculated for all samples as follows: z-score= (sample slope−mean of slopes in 6 negative control replicates)/(standard deviation of slopes in 6 negative control replicates). Samples with z-scores>2.33, i.e. deviating more than 2.33 SD from the mean of negative control (n=6), were considered positive in the Csm-based assay.

FIG. 17C shows a plot of results of serial dilutions of SARS-CoV-2 RNA standard (RGTM 10169, NIST) which was used to generate a standard curve with N1 CDC primers and probe mix (IDT, #10006713). Each reaction was performed in 3 technical replicates (filled circles). Standard curve was used to quantify viral RNA concentrations.

FIG. 17D shows a plot of results of Csm-based target RNA concentration followed by Csm-based detection with TtCsm6 and a fluorescent reporter was performed from a mock sample with and without lysis buffer (no lysis). The mock sample was made by spiking SARS-CoV-2 RNA fragment (final concentration $10^6$ copies/μL) into a nasopharyngeal swab negative for SARS-CoV-2. Fluorescence at 10 min incubation time was measured with qPCR instrument and normalized to the no target control (nasopharyngeal swab). Positive control (first bar) is a Csm-based RNA capture and detection from extracted RNA.

FIG. 17E shows a plot of results of TtCsm-based RNA capture assays coupled with AaCan2 readout performed using nasopharyngeal swab sample positive for SARS-CoV-2 with RT-qPCR (Ct~13.6) and its 10-fold serial dilutions in a negative nasopharyngeal swab (120 μL). Cleavage of fluorescent RNA reporter was detected by measuring fluorescence every 10 sec in a real-time PCR instrument (left). Data were plotted as mean of 3 replicates (centerline) ±sem (ribbon). Linear regions of the curves used for linear regression in the figure are boxed.

FIG. 17F shows an example of a plot of fold change vs non-targeting control (NTC) vs Ct value. Three clinical nasopharyngeal swab samples (120 μL) positive for SARS-CoV-2 with qPCR (Ct ~16.5, 18, 21.5) and RNA (120 μL) extracted from these samples were used for TtCsm-based RNA capture and TtCsm6-based detection. NTC was a qPCR-negative nasopharyngeal swab.

Use of Type III Csm-Complexes for Enrichment and Direct Sequencing of Target RNAs from Complex Mixtures FIG. 18A shows a schematic example of a capture & sequence approach that uses the type-III CRISPR-Cas complex (e.g., Csm or Cmr) to pulldown specific RNAs from total RNA, and then all mRNAs in the enriched sample are sequenced. In the Cleavage & Seq approach, the Csm or Cmr-complex is used to cleave off the polyA tail from the target mRNA and then sequence specific adapter is ligated. Only target RNA is sequenced.

FIG. 18B shows a schematic example of His-tagged Csm-complex bound to Nickel-derivatized (Ni-NTA) magnetic bead.

FIG. 18C shows an example of an image of an SDS-PAGE of Csm-complex after pull-down with nickel-derivatized magnetic beads. After binding, beads were separated with a magnet, and supernatant ("Super") was decanted. The beads were washed once ("Wash"), and the protein was eluted using 250 mM imidazole ("Elution").

FIG. 18D shows an example of results of sequence-specific RNA enrichment with TtCsm$^{Csm3-D34A}$ complex was tested using $^{32}$P 5'-end labeled IVT RNA fragments. Target and non-target RNA fragments were mixed with TtCsm$^{Csm3-D34A}$ complex, incubated at 65° C. for 20 min and pulled-down using Ni-NTA magnetic beads. After the magnetic pull-down, RNA was phenol-chloroform extracted from supernatants ("Free") and bead pellets ("Bound"). Extracted RNA was resolved using UREA-PAGE, exposed to a phosphor screen, and imaged on Typhoon imager (Amersham).

FIG. 18E shows a plot illustrating Csm-complexes efficiently cut target at femtomolar concentrations. X-axis shows 10-fold dilutions of target RNA, y-axis shows cleavage efficiency measured with RT-qPCR and calculated with ΔCt method as follows: Cleavage, $\% = 2\textasciicircum-(Ct_{cleaved\ sample} - Ct_{uncleaved\ control}) \times 100\%$.

Type-III-Based RNA Capture & Seq and Type-III-Based RNA Cleavage & Seq

Direct sequencing of RNA (without synthesis) is a powerful technology that enables unbiased detection and quantification of native RNAs, as well as detecting base modifications. However, these sequencing methods are often untargeted, which limits the utility for studying RNAs that are not highly abundant. Current techniques for RNA enrichment (i.e., oligo-capture) rely on hybridization between the nucleic acid probe and target sequence. Oligo-capture requires thermal annealing and is prone to off-targets, which restricts its applications. CRISPR-Cas complexes preorder the guide RNA (i.e., CRISPR RNA, crRNA) into a helical configuration, which facilitates hybridization with the complementary target. We have developed two approaches for sequence-specific enrichment of rare RNAs from complex mixtures (e.g., total RNA extracted from clinical samples) using type III CRISPR RNA-guided complexes (Type-III-based RNA Capture & Seq and Type-III-based RNA Cleavage & Seq; FIGS. 18A-E).

The Capture & Seq approach uses type-III Csm-complexes to pull down specific RNAs from total RNA, and then all RNAs in the enriched sample are sequenced (as shown in FIG. 18A, left). To capture target RNA, His-tagged Csm-complex with inactivated RNase activity is added to extracted RNA and incubated for 20 minutes to allow binding. The bound RNA is concentrated using nickel-derivatized magnetic beads and RNA is extracted (as shown in FIGS. 18B and 18C). Csm-complex efficiently captures target RNA, while non-target RNA primarily remains in the supernatant (as shown in FIG. 18D).

In the Cleavage & Seq approach, the type III-complex (i.e., Csm or Cmr) is used to cleave off the polyA tail from target mRNA and then sequence-specific DNA adapter is ligated with T4 ligase. In this case, only target RNA is passed through the pore and sequenced in the Oxford Nanopore device (as shown in FIG. 18A, right). Csm-complexes efficiently cleave (>95%) target RNA at femtomolar concentrations, which is comparable to the concentration of low abundant transcripts in total RNA samples extracted from human cells (as shown in FIG. 18E).

Improving Sensitivity and Demonstrating Quantitative Detection of RNA Using Type III CRISPR Systems The Type III CRISPR-Cas systems have recently been repurposed for sequence-specific detection of SARS-CoV-2 genomic RNA. Here we present new information that enables more sensitive, rapid, and specific detection RNA with Type III CRISPR-Cas systems.

The binding of Type III surveillance complexes to target RNA, activates two activities in the Cas10 subunit, an HD nuclease activity and a polymerase activity. The activated Cas10 subunit polymerizes nucleotide triphosphates (e.g., ATP) into a mixture of linear (e.g., Ax, where "x" is the number of adenosines in the polymer) and cyclic oligonucleotides (cAx). The addition of a single NTP (e.g., ATP) to any growing oligonucleotide causes the release of pyrophosphate and a proton. Each of the three Cas10 products can be measured to detect RNA [References 1-4].

Type III CRISPR Diagnostics for Quantitative Detection of RNA

Quantitative reverse transcription PCR (RT-qPCR) remains the "gold standard" for RNA quantification. However, in this method RNA is not measured directly but first is converted to DNA. Therefore, results depend on the efficiency of the reverse transcription, which complicates data interpretation. Here, we develop type III CRISPR based technology to directly detect and quantify RNA in biological samples. Target recognition by type III complexes activates polymerase domain in the Cas10 subunit that generates ~1000 cyclic oligoadenylates per bound RNA. The cyclic oligoadenylates trans-activate and allosterically regulate diverse multi-turnover ancillary nucleases that provide defense against invading genetic parasites (as shown in FIG. 19A below). FIG. 19A shows a schematic example of type III CRISPR RNA detection technology.

The rate of fluorescent signal released upon ssRNA reporter cleavage by ancillary nuclease Can2 is proportional to the amount of cyclic activator (i.e., cA4) in the 1-10 nM range (as shown in FIGS. 19B and 19C below). FIG. 19B shows a plot of kinetics of fluorescence ssRNA reporter cleavage by AaCan2 (300 nM) over a range of cyclic activator (i.e., cA4) concentrations (shown with gradients). Data is shown as the mean (center line) of three replicates±SD (ribbon). A linear fit of data (boxed) was used to calculate reaction rates shown in FIG. 19C. FIG. 19C shows a plot of reaction rates quantified in FIG. 19A vs. cyclic activator concentration.

There is a linear relationship between the amount of bound target, the cyclic oligoadenylate generated, and cleavage by the ancillary nuclease. Our data shows that fluorescence generated in a type III CRISPR detection reaction is proportional to the concentration of the input target RNA (as shown in FIGS. 19D and 19E below). FIG. 19D shows a plot of target RNA presence detected with TtCsm-complex (25 nM) in real time with AaCan2-based fluorometric readout. A linear fit of data (boxed) was used to calculate reaction rates shown in FIG. 19E. FIG. 19E shows a plot of reaction rates quantified in FIG. 19D vs. target RNA concentration (x-axis). Therefore, RNA of interest can be quantified using a standard curve generated with standards verified by an independent method. (as shown in FIG. 19E).

Titration of ATP to Tailor the Cyclic Oligoadenylate Profile Produced by Cas10

Figure 20B:
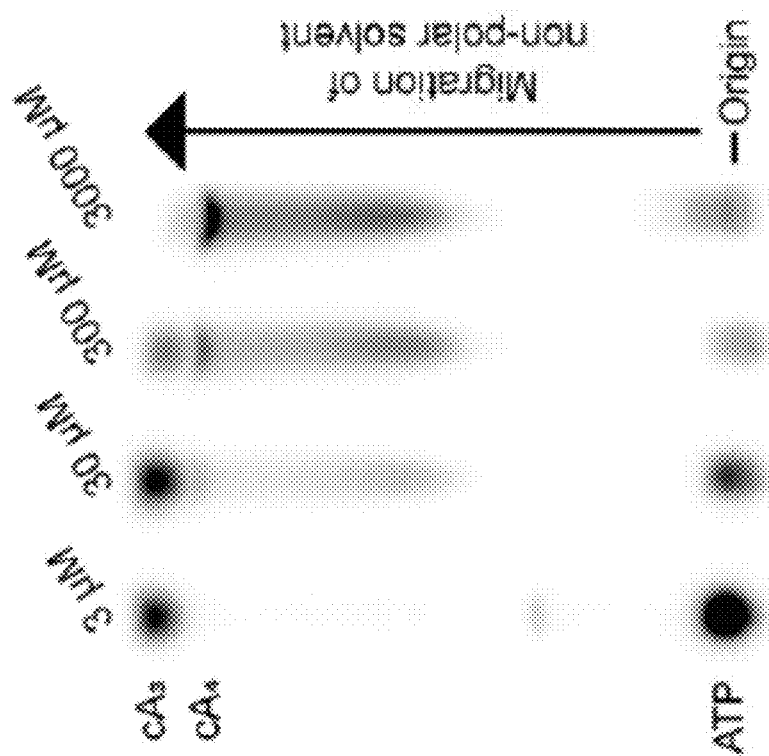
FIG. 20B shows an image of a TLC plate showing a mixture of cA3 and cA4 at intermediate ATP concentrations.
Figure 20A:
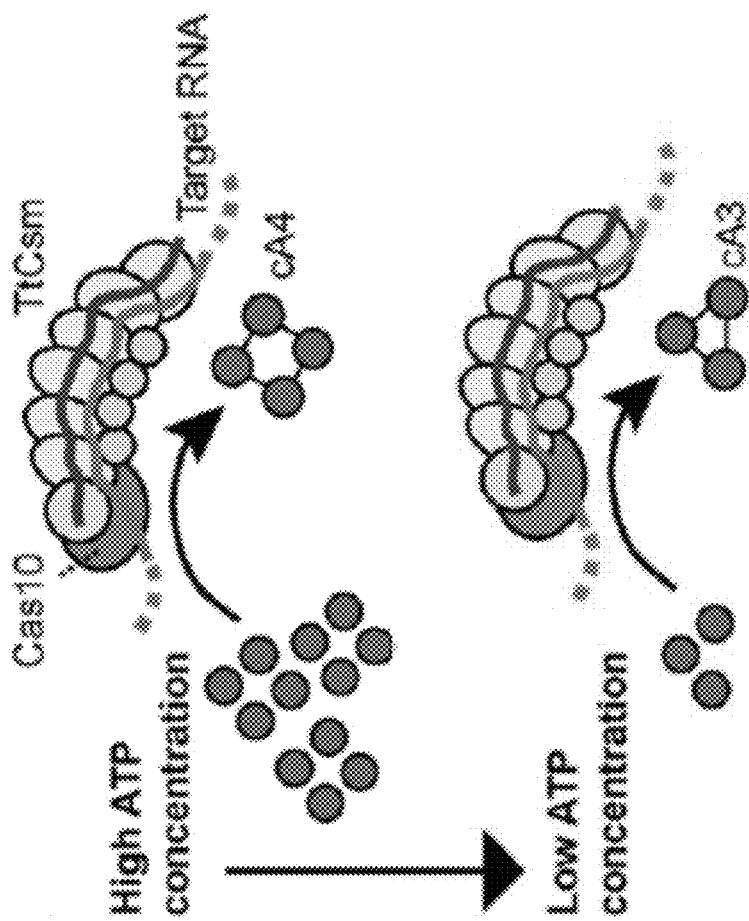
FIG. 20A shows a schematic example of an experiment to test impact of ATP concentration on cOA polymerization.

Target RNA-bound Type III surveillance complexes polymerize ATPs into a mixture of linear and cyclic oligoadenylates. However, the enzymatic effectors (e.g. nucleases, peptidases, pore-forming toxins) that are allosterically activated by cyclic oligoadenylates (cOAs) tend to be preferentially activated by specific oligoadenylate species. Therefore, a method to modify or tune the cOA profile produced by Type III surveillance complexes to match the preferred cOA activator of enzymatic effectors of interest is key to developing sensitive Type III CRISPR-based diagnostics. Here we show that titration of ATP enables tuning of the proportion of cA4 and cA3 produced by the TtCsm complex (as shown in FIGS. 20A and 20B). In this example higher concentrations of ATP (e.g. 3000 µM) lead to the polymerization of longer chains of cOAs (such as cA4).

TLC (Thin Layer Chromatography) Analysis of TtCsm-Polymerized cOAs Over a Range of ATP Concentrations FIG. 20A shows a schematic example of an experiment to test impact of ATP concentration on cOA polymerization.

FIG. 20B shows an image of a TLC plate showing a mixture of cA3 and cA4 at intermediate ATP concentrations. TtCsm complex was incubated with SARS-CoV-2 RNA at 60° C. for 1 hour, in the presence of an excess of unlabeled ATP (3, 30, 300 or 3000 µM) and a small amount of $\alpha$-$^{32}$P-ATP. These reactions were phenol-chloroform extracted to remove proteins, and the retained nucleic acids were spotted on TLC plates. The edge of the TLC plate nearest to the origin was dipped into non-polar solvent that migrates up the TLC plate. Non-polar molecules migrate furthest from the origin. TtCsm complex produces mostly cA4 at biologically relevant concentrations of ATP, produces a mixture of cA3 and cA4 at intermediate ATP concentrations, and produces mostly cA3 at low ATP concentrations.

Type III CRISPR Chain Reaction

The high sensitivity of PCR (Polymerase Chain Reaction) stems from the exponential amplification of DNA. Each newly polymerized DNA duplex is used as a template for further replication in successive extension steps, setting up the "chain reaction" of PCR.

Figures 21A, 21B, 21C:
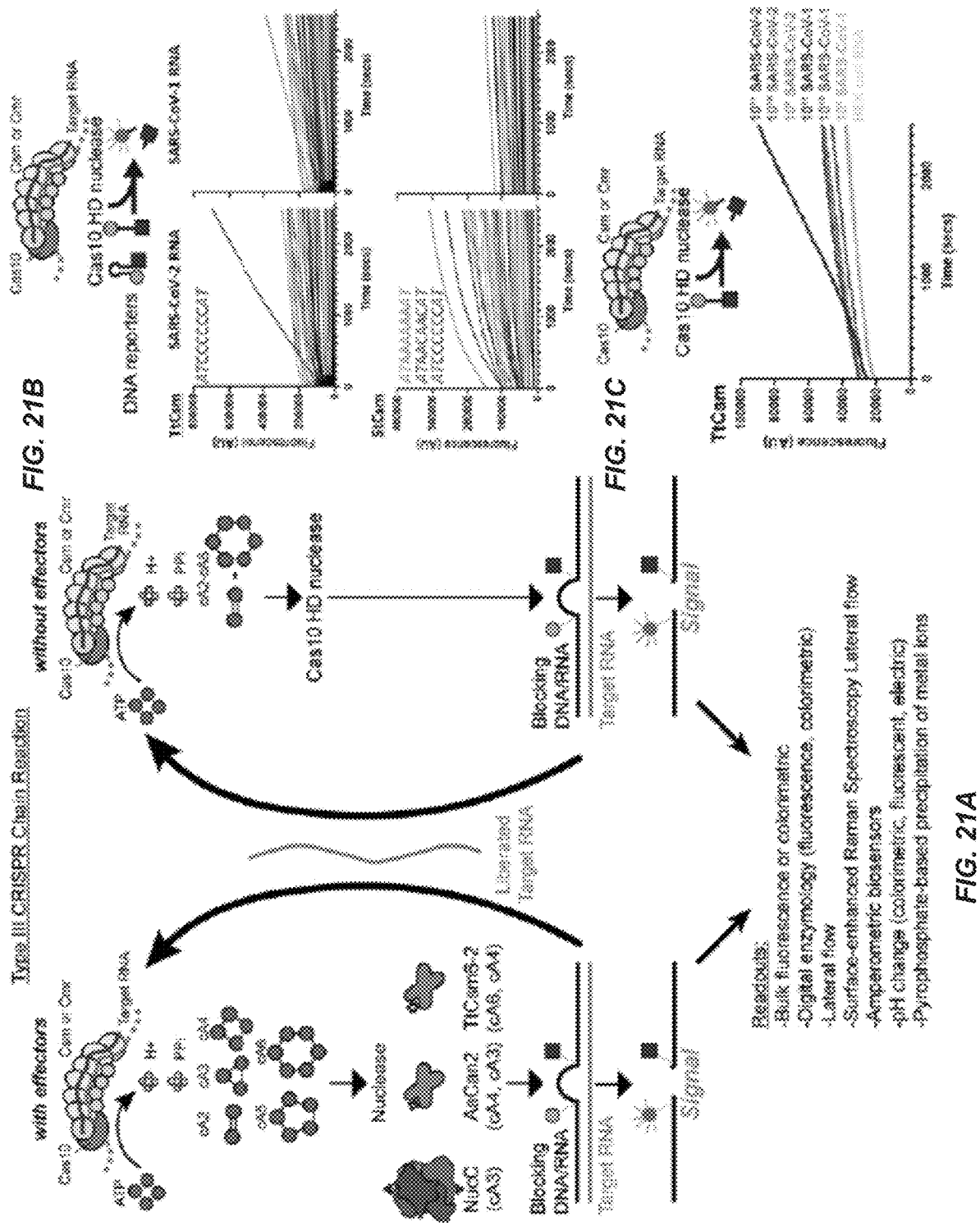
FIG. 21A shows a schematic of an example of a type III CRISPR Chain Reaction.
FIG. 21B shows a schematic of an assay to determine DNA cleavage preference of TtCsm and SthCsm complexes.
FIG. 21C shows an example of kinetics of TtCsm-mediated cleavage of the fluorescent reporter.

In the Type III CRISPR Chain Reaction, a target-bound Type III surveillance complex (e.g. Csm or Cmr) polymerizes ATP into cOAs. cOAs bind and activate enzymatic effectors, (e.g. nucleases). The cOA-activated DNase or RNase cleaves a "blocking" DNA or RNA that acts as both a i) fluorescent reporter, and ii) a physical obstruction that blocks access to a mimic of the target RNA sequence. Cleavage of the DNA relieves the previously blocked target RNA mimic to be accessible for binding by the Csm or Cmr complex, which becomes activated and generates more cOAs. This sets off a chain reaction, where more type III effectors are activated (i.e., target bound), more cOAs are generated, more nucleases are activated, blocking reporters are cleaved, and more of the blocked RNA target is liberated, which continues to feed the chain reaction (as schematically shown in FIG. 21A).

In another version of Type III CRISPR Chain Reaction, a target-bound Csm/Cmr complex directly cleaves the blocking DNA or RNA via the Cas10 HD domain. A similar chain reaction is set off, that does not require ATP or an ancillary enzyme effector. This format also allows for multiplexing against different targets. Using Csm/Cmr complexes that have HD domains with different nucleotide specificities, individual blocking DNA or RNA containing different reporters (e.g. fluorophores), that are base paired with an RNA target can be programmed for simultaneous detection of multiple RNAs in a single reaction. The DNase activity of Cas10 from either TtCsm and SthCsm complexes is specifically activated when bound to a complementary RNA target, and these two type III complexes possess different ssDNA sequence cleavage preferences (as shown in FIGS. 21B and 21C).

In all versions of the Type III CRISPR Chain Reaction, all three Cas10 products can be measured for sensitive detection of RNA.

Pyrophosphates can be measured by methods that detect the precipitation of insoluble complexes formed between pyrophosphates and divalent metal ions, for example Calcein-based assays [References 1,2].

The protons produced by target RNA-bound Type III surveillance complexes reduces the pH. The decrease in pH can be measured by colorimetric pH indicators (e.g., Phenol Red), fluorescent pH indicators (e.g., BCECF-AM) [Reference 5] or by field-effect transistors—including ion-sensitive field-effect transistors (U.S. Pat. No. 9,365,904, issued on Jun. 14, 2016, which is incorporated by reference in its entirety for all purposes) and graphene field-effect transistors [Reference 6]. Colorimetric pH indicator color change can be detected by eye, or absorbance plate reader. Fluorescent pH indicator change can be detected by a fluorescent plate reader. Field-effect transistors can be used to make quantitative and sensitive readouts of proton concentration.

Cyclic oligoadenylates can be indirectly measured by the activation of effectors with different enzymatic activities (e.g. nucleases, peptidases, pore-forming toxins). The activity of nucleases [References 1-4] and peptidases can be measured by cleavage of an RNA, DNA or peptide tether that is labelled i) on either end with a fluorophore-quencher pair (cleavage detected by bulk fluorescence or digital enzymology), ii) on either end with a fluorophore and/or digoxigenin and/or biotin (cleavage detected by lateral flow, surface-enhanced Raman spectroscopy lateral flow), iii) with multiple gold nanoparticles (cleavage detected by bulk colorimetric or digital enzymology), iv) on one end with a redox-active molecule (e.g., methylene blue) and linked on the other end to a gold electrode (cleavage detected by amperometric bio sensor).

FIG. 21A shows a schematic of an example of a type III CRISPR Chain Reaction. The type III CRISPR Chain Reaction utilizes ancillary effector nucleases activated by cOA generated by target RNA-bound Csm or Cmr (left), or a similar chain reaction that utilizes the nuclease activity of the HD domain of Cas10 (right). Cleavage of a blocking nucleic acid liberates a target RNA that is bound by free Csm or Cmr complex in the solution, thereby exponentially amplifying the detection of a single target molecule in solution. Labeling of the blocking nucleic acid with different functional groups enables diverse readout methodologies, listed in figure. Further the chain reaction increases the number of protons and pyrophosphates generated by type III CRISPR-based diagnostics, which can also be readout using diverse methodologies. The preferences of thermostable CtNucC (dsDNA with GAACT motif), AaCan2 (ssRNA with ACGACG motif) and TtCsm6-2 (ssRNA with CGU-CGU motif) enzymes have been recently determined (FIGS. 12 and 15), and are incorporated into the blocking DNA or RNA sequences. Sequence preferences are important to design nucleic acid tethers that are efficiently cleaved by nucleases to release the fluorescent signal. Target RNA with and without phosphorothioate modifications will be tested.

FIG. 21B shows a schematic of an assay to determine DNA cleavage preference of TtCsm and SthCsm complexes. TtCsm complex cleaves a C-rich ssDNA fluorescent reporter when bound to SARS-CoV-2 in vitro transcribed RNA, but not in the presence of SARS-CoV-1 in vitro transcribed RNA that has been spiked into 1×TE buffer.

FIG. 21C shows an example of kinetics of TtCsm-mediated cleavage of the fluorescent reporter. The kinetics of TtCsm-mediated cleavage of the fluorescent reporter with sequence 5'-ATCCCCCCAT-3' is different when SARS-CoV-2 and SARS-CoV-1 in vitro transcribed RNAs are spiked into total HEK cell RNA, but remains specific.

Chimeric Type III CRISPR Surveillance Complexes of a Defined Length and Tethered Nuclease Type III surveillance complexes that are purified from expression in native or heterogeneous host bacteria or archaea are often contain guides crRNA-guides of various lengths. Precise control over the size of the guide RNA will improve homogeneity and consistent performance of this diagnostic, where the "seed" regions changes along with the length of the crRNA-guide. We developed a strategy to control the size of the type III surveillance complexes that involves the design of a chimeric type III and type I CRISPR system (FIG. 4). The CRISPR array contains chimeric repeats in which the 5' end of the *Pseudomonas aeruginosa* I-F repeat (5'-GTTCACTGCCGTGTAGGCAG) that is bound and cleaved by Csy4, is fused to the 3' end of the *Thermus thermophilus* III-A repeat (5'-ATTGCGAC) that is bound by Csm4. Further, 5 nucleotides were added between the spacer sequence and the chimeric repeat sequence to provide room for both Csm5 and Csy4 to simultaneously bind the mature guide RNA. During in vivo bacterial protein expression, Csy4 is co-expressed in addition to all the subunits needed to form a mature type III surveillance complex (i.e. Csm1-Csm5 for TtCsm complex). Csy4 cleaves and processes in vivo transcribed chimeric CRISPR loci, and a chimeric TtCsm-Csy4 complex is produced. The chimeric TtCsm-Csy4 complex is active for specific detection of SARS-CoV-2 RNA.

In addition, to adding a type I CRISPR RNA processing enzyme (Cas6 family protein) to the type III Csm or Cmr complexes, we are also fusing ancillary nucleases to these type III complex as a way to increase the concentration and proximity to the nucleases to the type III complexes (FIG. 5). This approach is anticipated to improve the sensitivity of target RNA detection.

Type III CRISPR Surveillance Complexes of a Defined Length.

FIG. 22A shows a schematic of the RNA spacer and guide design. The RNA spacer and guide design may express and purify a chimeric type III-type I surveillance complex containing either six subunits of Csm3 (6×Csm3 chimera) or four subunits of Csm3 (4×Csm3 chimera).

FIG. 22B shows an example plot of results of size exclusion chromatography of wildtype TtCsm complex (blue) overlayed with 6×Csm3 and 4×Csm3 chimeric complexes. The chimeric type III-type I surveillance complex elute from the SEC in a more monodispersed peak than the wildtype TtCsm complex.

FIG. 22C shows SDS-PAGE and Urea-PAGE gels of the proteins and RNAs present in fractions A and B of the three different protein complexes. 6×Csm3 and 4×Csm3 chimeric complexes have all the proteins expected in a Csm complex, and include Csy4. There are several lengths of nucleic acids present in the fraction B aliquots of all protein complex preparations. There are also bands of nucleic acid seen at the expected sizes for both 6×Csm3 and 4×Csm3 chimeric complexes.

FIG. 22D shows a schematic and plots of 4×Csm3 and 6×Csm3 chimeric complexes. The 6×Csm3 and 4×Csm3 chimeric complexes detect SARS-CoV-2 RNA with comparable sensitivity to wildtype TtCsm complex, and do not strongly detect SARS-CoV-1 RNA.

Fusion of TtCsm Complex with AaCan2 Ancillary Nuclease to Increase the Sensitivity of Type-III-Based Detection.

Figures 23A, 23B:
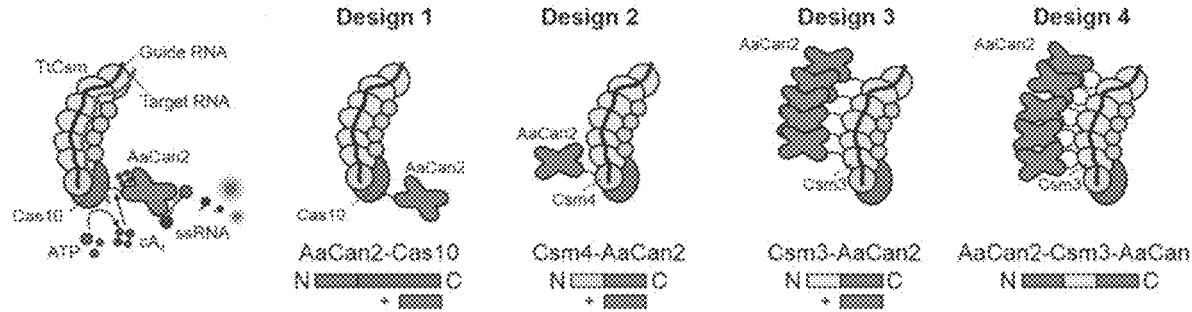
FIG. 23A shows a schematic example of a Cas10 subunit of TtCsm complex that polymerizes ATP into cyclic oligoadenylates (such as cA4) when the complex binds target RNA.
FIG. 23B shows schematic examples of TtCsm-AaCan2 fusions designs.

FIG. 23A shows a schematic example of a Cas10 subunit of TtCsm complex that polymerizes ATP into cyclic oligoadenylates (such as cA4) when the complex binds target RNA. Dimeric ancillary nuclease Can2 from Archaeoglobi archaeon JdFR-42 (AaCan2) is activated by cA4 and cleaves ssRNA reporter, which releases a fluorescent signal. AaCan2 is fused to TtCsm-complex and has immediate access to the produced cA4. Physical proximity to cA4-producing Cas10 subunit boosts AaCan2 activity and enhances sensitivity of target RNA detection.

FIG. 23B shows schematic examples of TtCsm-AaCan2 fusions designs. Designs 1-3: Single AaCan2 copy is fused to TtCsm1, TtCsm4, or TtCsm3. Csm4 can be fused at either the N- or C-terminus. Untagged AaCan2 will be co-expressed to supply the second subunit for dimerization. Design 4: Two copies of AaCan2 are fused to Csm3 (and/or Csm2 and Csm4) to enable dimerization without expressing extra protein Detection of Small RNAs (miRNA, siRNA, piRNA, Etc.)

MicroRNAs (miRNAs) are important early biomarkers of cancer, glaucoma and infectious diseases [References 7-10]. However, the small size (~22 nucleotides) and sequence homology (e.g. single-nucleotide variation) of these biomarkers makes them difficult to detect using traditional PCR, Cas13 or isothermal amplification methods [References 11-13]. Small type III surveillance complexes can be produced with guide RNAs that are shorter (i.e., 20-30 nts) than the median size of spacers sequences typically seen in type III CRISPR systems (~40 bp) (FIG. 3), to enable facile, sensitive and specific detection of small RNA biomarkers critical to human health. Type III CRISPR concentration followed by buffer exchange is expected to enable testing for small RNA biomarkers directly from complex patient samples (i.e., saliva, urine, blood) that typically require upstream purification before similar diagnostic tests (i.e., PCR).

Discussion of Results

Type III-Mediated Sequence-Specific Enrichment of RNA

Type III CRISPR RNA-guided complexes (i.e., Csm and Cmr) bind and cleave complementary single-stranded RNA (ssRNA) targets [Reference 25]. Complementary RNA is cleaved in six-nucleotide increments by metal-independent nucleases (Csm3 or Cmr4) that form the oligomeric "backbone" of the complex26. Type III complexes release fragments of the cleaved target, which inactivates ATP polymerization by the Cas10 subunit26. Previously, we mutated residues in the Csm3 subunit responsible for target RNA cleavage (D34A), purified the RNase-dead complex (TtCsm$^{Csm3-D34A}$), and showed that the mutant complex provides more sensitive detection of viral RNA than the wild-type complex [Reference 16]. To further increase the sensitivity, we set out to determine if TtCsm$^{Csm3-D34A}$ could be used to concentrate sequence-specific RNAs. To test this approach, we mixed P32-labeled target or non-target RNAs with TtCsm$^{Csm3-D34A}$, incubated for 20 minutes, and concentrated the His-tagged complex using nickel-derivatized magnetic beads (FIGS. 5A and 9A). The beads were concentrated using a magnet, and RNAs were extracted from the bound and unbound fractions. The type III complex captured most of the radiolabeled target RNA (76±5.8%), while non-target RNA primarily remains in the supernatant (FIGS. 5B, 9B, and 9C). To determine whether type III CRISPR-based RNA capture and concentration results in the synthesis of more cyclic nucleotides, we mixed Csm-beads with 120 µL, of a sample containing SARS-CoV-2 RNA and total RNA extracted from HEK293T cells (FIG. 5C and also the "Methods" section below). After concentrating the beads with a magnet, we resuspended the pellet in a buffer containing $\alpha$-$^{32}$P-ATP and analyzed the reactions using thin-layer chromatography (TLC). The results demonstrate that type III CRISPR-based concentration increases levels of cA3 and cA4, as compared to the reaction performed without RNA concentration (FIGS. 5C, 5D, AND 9D).

Previously, we repurposed TtCsm6, a cA4-activated ribonuclease, to generate a real-time fluorescent readout for Csm-based RNA detection16 (FIG. 5E, top). We reasoned that increased cA4 levels after RNA enrichment will boost the nuclease activity of TtCsm6 and therefore increase the sensitivity of the RNA detection. To test this hypothesis, we titrated $10^8$ to $10^5$ copies/µL of SARS-CoV-2 N-gene RNA into total RNA extracted from HEK293T cells, concentrated the target RNA using TtCsm$^{Csm3-D34A}$, resuspended the beads in a buffer containing ATP, and then transferred the polymerization products to a reaction containing TtCsm6 and a fluorescent RNA reporter (i.e., FAM-RNA-Iowa Black FQ). Csm-based RNA enrichment increased the sensitivity of the assay 100-fold compared to the assay without the pull-down (FIG. 5E). Taken together, these results demonstrate how type III-A CRISPR-complexes are used to capture sequence-specify RNAs, resulting in a higher concentration of cyclic nucleotides, which improves the sensitivity of sequence-specific RNA detection.

CARF-Nucleases Can1 and Can2 Exhibit cA3- and cA4-Specific Nuclease Activities

Csm6 proteins contain an amino-terminal CARF (CRISPR-associated Rosman Fold) and a carboxy-terminal HEPN (Higher Eukaryotes and Prokaryotes Nucleotide-binding) domains [References 10, 12]. Csm6 family proteins form homodimers, and the two CARF-domains bind cA4 [References 23,27] or cA6 [Reference 22], which activate the C-terminal HEPN nuclease domain. However, the CARF domain of Csm6 proteins also degrades the cyclic nucleotide, which inactivates the nuclease and limits the sensitivity of Csm6-based assays [Reference 28]. To improve sensitivity, we sought to identify and incorporate a CARF-nuclease that is activated by but does not degrade cA4.

CRISPR ancillary nucleases (Can) are another family of recently identified proteins that are activated by cyclic oligoadenylates and lack ring nuclease activity. [References 29-31]. Like Csm6 proteins, these proteins also contain amino-terminal CARF domains, but the carboxy-terminal nucleases are distinct. The Can1 protein from *Thermus thermophilus* (TtCan1) has a unique monomeric architecture with two non-identical CARF domains, one nuclease-like domain (NLD) and one restriction endonuclease domain (PD-[D/E]XK) [Reference 31], while Can2 nucleases contain a single CARF domain and form symmetrical homodimers [Reference 29,30] (FIG. 6A).

To identify Can1 and Can2 orthologs compatible with the TtCsm complex, we generated profile Hidden Markov models (HMMs) to query publicly available microbial genomes and metagenomes from NCBI and JGI. This analysis identified 204 Can1 and 3,121 Can2 proteins. Based on this analysis, we selected TtCan1 and three Can2 orthologs from thermophilic organisms for cloning and expression (FIG. 6B). While previous research demonstrated metal-dependent nicking of supercoiled DNA by TtCan1 that is dependent on activation by cA431, the impact of other cyclic oligoadenylates on TtCan1 activity has not been reported. We purified TtCan1 and tested nuclease activity against plasmid DNA in the presence of five different cyclic oligoadenylates (cA2-cA6) (FIGS. 14A-C). To our surprise, TtCan1 robustly degrades plasmid DNA to ~100 bp fragments in the presence of cA3 and Mn$^{2+}$, while cleavage with cA4 is comparable to the background activity in the absence of an activator (FIGS. 6C, left and 10D). To determine whether the TtCan1 nuclease has any sequence preference, we deep-sequenced cleavage fragments, aligned resulting reads to the plasmid sequence, and identified cut sites. This analysis failed to identify common sequence motifs, suggesting that TtCan1 DNase activity is non-sequence specific (FIG. 10E). Based on the unexpected activation of TtCan1 with cA3, we tested several other substrates and discovered that TtCan1 is a cA4-dependent single-stranded RNase (ssRNA) but does not cleave ssDNA (FIGS. 6C, 10F, and 10G). Taken together, our in vitro assays show that TtCan1 is a non-sequence specific double-stranded DNase when activated with cA3 and a single-stranded RNase when activated with cA4.

Can2 genes from *Clostridium thermobutyricum*, *Thermus thermophilus*, and Archaeoglobi archaeon JdFR-42 were cloned and expressed in *E. coli*. However, only the Can2 protein from Archaeoglobi archaeon JdFR-42 (AaCan2) purified in quantities sufficient for biochemical assays (FIGS. 11A, 11B). We systematically tested the activities of AaCan2 against different substrates with a range of cyclic oligoadenylates (FIGS. 11C, 11D). Like TtCan1, AaCan2 is also a Mn$^{2+}$- and cA3-dependent dsDNase (FIGS. 6D, left gel; 11C), or a ssRNase when activated with cA4. The ssRNA activity of AaCan2 is supported by either Mn$^{2+}$ or Mg$^{2+}$ (FIGS. 6D and 11D). Reproducible cleavage of ssDNA is also detectable for AaCan2, but the activity is Mn$^{2+}$-specific, and robust cleavage requires a higher concentration of cA4 (i.e., 45 nM) (FIGS. 6D, 11D). Cleavage of ssDNA produces a discrete band suggesting that the enzyme processes ssDNA to a minimal cleavage product or that the activity is sequence-specific (FIGS. 6D, 11D). While cA4-dependent activities of AaCan2 are consistent with activities previously reported for the Can2 protein from *Treponema* succinifaciens29 (i.e., TsuCard1; FIG. 6B), cA3-dependent dsDNA cleavage has not been previously reported. Collectively, our results demonstrate that Can1 and Can2 have a broad spectrum of nuclease activities, which are determined by the cyclic nucleotide activator (i.e., cA3 or cA4).

Can2 Ancillary Nuclease Provides Sensitive Csm-Based SARS-CoV-2 Detection

To determine whether incorporating TtCan1 or AaCan2 improves sensitivity of the Csm-based RNA detection assay, we screened a library of synthetic RNA reporters designed to identify sequences that might be preferred by these nucleases (Table 1, SEQ ID NOS. 1-47, FIGS. 12A-C). Consistent with our gel-based assays, cA4-activated AaCan2 cleaves RNA reporters in the presence of either Mg$^{2+}$ or Mn$^{2+}$, but reactions with Mn$^{2+}$ consistently result in higher fluorescent signal (FIGS. 12A,B). While TtCan1 cleaves the same RNA reporters as AaCan2, cleavage by TtCan1 requires higher concentrations of cA4 and produces less fluorescent signal (FIG. 13).

Having established that AaCan2 is more active than TtCan1, we set out to compare AaCan2 to the sensitivity of TtCsm6, which we used previously. This comparison was performed by measuring cA4 concentration-dependent activity for AaCan2 and TtCsm6 using the preferred RNA reporter for each of the respective enzymes (FIGS. 12A-C). AaCan2 produces a similar fluorescent signal to TtCsm6 when activated with 20-fold less cA4 (0.5 nM versus 10 nM) (FIG. 6E). Moreover, AaCan2 exhibits an incremental decrease in cleavage rates with decreasing cA4, while TtCsm6 exhibits a dramatic (non-linear) drop in the activity.

The distinction in activity between these enzymes is consistent with the ring-nuclease activity of TtCsm6 rapidly degrading its activator, while AaCan2 binds and preserves the cyclic nucleotide (FIG. 11E).

Finally, we incorporated AaCan2 into the type III-based detection assay and benchmarked this combination against TtCsm6-based detection (FIGS. 6F, 6G). The TtCsm6-based assay reliably detects $10^6$ copies/μL of target RNA (FIG. 6F), while AaCan2-based reactions are more sensitive ($10^5$ copies/μL) (FIG. 6G). While coupling TtCsm-detection to AaCan2 results in significantly higher sensitivity, it also results in higher background, but this background is only evident in the presence of the TtCsm-complex (FIGS. 6F, 6G), whereas AaCan2 alone demonstrates very little non-specific cleavage (FIG. 6E). This disparity suggests that non-sequence specific activation of the Cas10 polymerase may generate low levels of cA4, which stably activates AaCan2, whereas the ring-nuclease of TtCsm6 rapidly degrades cA4 limiting the background signal. Collectively, these results demonstrate that coupling AaCan2 with TtCsm$^{Csm3-D34A}$ provides more sensitive RNA detection.

Incorporating cA3-Dependent Nuclease Activity does not Provide Additional Sensitivity of Viral RNA Detection While our assay uses cA4-activated collateral cleavage of ssRNA reporters, the TtCsm$^{Csm3-D34A}$-complex also produces cA3 (FIGS. 5D, 9D). We hypothesized that combining cA3- and cA4-sensing nucleases might enhance the sensitivity of TtCsm-based detection (FIG. 7A). NucC (Nuclease, CD-NTase associated) endonucleases are activated by cA3 and found next to CBASS (cyclic oligonucleotide-based anti-phage signaling system) [References 32, 33] and type III CRISPR/Cas immune systems [Reference 24].

Unlike CARF-nucleases, NucC nucleases adopt a homotrimeric structure forming a 3- fold symmetric pocket for cA3 binding. Binding to cA3 triggers dimerization of NucC homotrimers positioning restriction endonuclease-like domains for dsDNA cleavage [References 32, 33]. We purified three thermophilic NucC orthologs and tested cA3-dependent dsDNA cleavage (FIGS. 14A-F). The NucC from *Clostridium tepidum* (CtNucC) has the highest dsDNase activity and digests plasmid DNA into 300-400 bp fragments in the presence of cA3 (FIGS. 7B, left, 15). Deep sequencing of cleavage fragments determined that all purified NucC nucleases have a preference for 5'-ANNT-3' sequence motif, which is consistent with previously published work33 (FIG. 7B, right, FIGS. 15B-E).

Next, we set out to determine if CtNucC and AaCan2 could be combined into a single reaction to improve the sensitivity of detection with TtCsm$^{Csm3-D34A}$. To perform fluorescent assays with CtNucC, we designed a 31-bp dsDNA probe comprising six repeats of the optimal cleavage site (Table 1, SEQ ID NOS. 1-47). The lowest concentration of cA3 detected by CtNucC is 0.5 nM, which is 10-fold more sensitive than TtCan1 and 100-fold more sensitive than AaCan2 (FIG. 7C). However, TtCsm$^{Csm3-D34A}$ coupled with CtNucC and dsDNA reporter only detects high concentrations of target RNA (i.e., $10^7$ copies/μL; FIG. 7D). Further, combining CtNucC with AaCan2 and matching fluorescent probes (i.e., dsDNA and ssRNA, respectively) (FIG. 7A) into a single reaction does not improve the sensitivity compared to detection with AaCan2 alone (FIGS. 7D, 16A). While CtNucC is sensitive to cA3 activation, the TtCsm-complex may not produce sufficient concentrations of this cyclic nucleotide.

Type III CRISPR Based RNA Capture and Detection from Patient Samples

RNA extracted from nasopharyngeal swabs of COVID-19 patients are complex mixtures of nucleic acids derived from the host, the virus, and microbial communities residing in the upper respiratory tract. To determine if TtCsm complex can capture SARS-CoV-2 RNA in such mixtures, we extracted total RNA from nasopharyngeal swabs of 17 positive and 6 negative patients diagnosed with RT-qPCR (FIG. 17A).

We used 3 μL of each RNA sample to perform the TtCsm-AaCan2 reaction and 120 μL as input for Csm-based RNA capture followed by a polymerization reaction and fluorometric detection with AaCan2. Only samples with the highest viral RNA load (Ct<17) tested positive in TtCsm-AaCan2 reaction, while Csm-based RNA capture assay detected RNA of SARS-CoV-2 in 10 samples (60% of the qPCR positive samples) (FIGS. 8A, 8B, 17B). Csm-based RNA capture increases the sensitivity ~100-fold and allows to reliably detect SARS-CoV-2 in patient samples with Ct values ≤23.2, which corresponds to ~$10^4$ copies/μL of viral RNA (FIGS. 17B, 17C).

RNA extraction kits are expensive, time-consuming, and require specialized equipment. To eliminate this step, we tested if the TtCsm complex can capture and concentrate target RNA directly from a nasopharyngeal swab sample without prior RNA extraction. To identify lysis conditions that do not inhibit activity of the TtCsm-complex, we tested 10 lysis buffer compositions with varying concentrations of detergents (i.e., Triton X-100 or NP-40) and chelators (i.e., EDTA or EGTA) (FIG. 17D). We mixed Csm-beads with a mock sample made by spiking SARS-CoV-2 RNA fragment into SARS-CoV-2 negative nasopharyngeal swab, added lysis buffer, and incubated for 20 min at 65° C. This heat treatment inactivates SARS-CoV-2, promotes lysis, and allows RNA binding by TtCsm-complex and its downstream activities [References 34, 35]. After pulling down Csm-beads with a magnet, we discarded the supernatant and performed polymerization reactions followed by a TtCsm6-based fluorescent readout. TtCsm complex detects spiked-in RNA in the presence of Triton X-100 (0.025-0.1%) and EGTA (1 mM), while other buffers significantly inhibited Csm-based detection (FIG. 17D).

Finally, to assess the sensitivity of the direct viral detection in swab samples with RNA capture and AaCan2-based readout (FIG. 4c), we used a patient sample positive for SARS-CoV-2 RNA (Ct ~13.6) that was 10-fold serially diluted in a negative swab sample (FIG. 8D). In this assay, we used lysis buffer supplemented with 0.05% Triton X-100 and 1 mM EGTA. Csm-based RNA capture assay detects SARS-CoV-2 in unprocessed samples (i.e., no RNA purification) with Ct>21.2 (FIGS. 8D, 17F), which corresponds to $5 \times 10^4$ copies/μL and ~5-fold less sensitive compared to detection performed using purified RNA (FIGS. 8B, 17E). To compare the efficiency of the direct detection from the lysed nasopharyngeal swab relative to detection from extracted RNA, we used three nasopharyngeal swab samples that previously tested positive for SARS-CoV-2 using RT-qPCR (FIG. 17F). All three samples tested positive using direct detection from nasal swabs, however direct detection from patient samples resulted in a higher signal-to-noise ratio. This difference suggests that further optimization of the lysis conditions may lead to higher sensitivity (FIG. 17F).

Discussion

CRISPR-based diagnostics have been progressing at a remarkable pace since the start of the COVID-19 pandemic

[Reference 4]. However, most CRISPR-based SARS-CoV-2 diagnostics described to date still require nucleic acid extraction and pre-amplification to reach clinically relevant sensitivity [Reference 4]. Ongoing efforts focus on improving the sensitivity, ease of execution, and speed of the viral detection. Previous efforts have leveraged the intrinsic signal amplification of type III CRISPR systems to detect SARS-CoV-2 in RNA extracted from clinical samples [References 16-18, 24]. Here, we demonstrate how type III CRISPR systems can be used for viral RNA capture and detection directly from unprocessed patient samples. This approach, coupled with a Can2-based fluorescent readout, allows direct detection of $5 \times 10^4$ viral RNA copies per μL in clinical samples without RNA extraction and pre-amplification steps.

The natural capacity and programmability of Cas9 have been previously adopted for target DNA capture and concentration [References 36-38]. In addition, Cas9 was repurposed to bind and pull down specific mRNAs with a protospacer adjacent motif (PAM) grafted in trans on a complementary DNA oligonucleotide [Reference 39]. While such approaches seem preordained to be incorporated in molecular testing, CRISPR-based nucleic acid enrichment has not been previously explored to increase the sensitivity and streamline CRISPR-based diagnostics. Cas13-based CRISPR diagnostics rely on collateral nuclease activity triggered by nucleic acid binding [References 8, 40]. However, the same metal-independent HEPN (Higher Eukaryotes and Prokaryotes Nucleotide-binding domain) nuclease domain that executes collateral activity also cleaves the bound target [Reference 41]. These activities cannot be decoupled, making Cas13-based RNA capture and subsequent detection unavailable. In type III CRISPR systems, target binding and collateral RNase activities are performed by separate proteins and coordinated through a secondary messenger signaling mechanism. Binding target RNA triggers Cas10 subunit of type III Csm and Cmr complexes to convert ATP to cyclic oligoadenylates (cOAs) licensing indiscriminate cleavage by trans-acting nucleases [References 10, 12]. Target cleavage acts as an off switch for cyclase activity and downstream effectors. Mutations in the catalytic site of backbone RNase (i.e., Csm3) subunit abolish target RNA cleavage and boost target-dependent cOA synthesis [Reference 13]. We have taken advantage of this feature and developed a Csm-based RNA enrichment method using RNase-dead (TtCsm$^{Csm3-D33A}$) TtCsm complex.

Incorporating RNA capture increases the sensitivity of type III CRISPR-based diagnostic and allows direct detection in clinical samples without RNA extraction prerequisite for most current platforms. To further improve sensitivity, we identify and test ancillary nucleases Can1, Can2, and NucC. Most ancillary nucleases in type III CRISPR have a single CARF domain fused to the C-terminal effector and homodimerize to bind cyclic oligoadenylates (cOAs) with two-fold symmetry, i.e., cA4 and cA6 [References 27, 29, 30, 42]. TtCan1 is an exception to this pattern and has a monomeric structure with two non-identical CARF domains forming an allosteric pocket accommodating cyclic oligoadenylates [Reference 31]. Contrary to previous work, our biochemical data suggest that nuclease activities of TtCan1 are primarily regulated by cA3 rather than cA4. TtCan1 is proposed to emerge as Can2 gene duplication, fusion, and subsequent divergent evolution [References 30, 31]. Similar fusion of two ancient CARF-like domains into a SAVED (SMODS-Associated and fused to Various Effector Domains) domain was recently discovered in Cap4 nucleases that are part of CBASS (Cyclic oligonucleotide-Based Antiphage Signaling System) immunity and are activated by cyclic trinucleotides [Reference 43]. We hypothesize that duplication and subsequent fusion of Can2 genes exemplifies an evolutionary mechanism for diversifying cyclic nucleotide signaling in bacterial immune systems. Our phylogenetic comparison of Can1 and Can2 nucleases identifies that the emergence of Can1 proteins follows a polyphyletic fashion and appears multiple times over the evolutionary timeline.

The genome of *T. thermophilus* (i.e., HB8 and HB27 strains) encodes both Csm6 and Can1 CARF-nucleases [Reference 31]. While the Cas10 cyclase subunit in the type III-A TtCsm complex primarily produces cA4, which is sensed by TtCsm6 RNase, we also detected substantial synthesis of cA3. We hypothesize that in vivo, this secondary product activates TtCan1 DNase, providing an additional layer of immune defense. RNA cleavage by Csm6 nucleases results in host cell senescence facilitating phage clearance [References 15,44]. We further hypothesize that failure to clear the infection results in continuous polymerization by Cas10 and accumulation of cA3 licensing TtCan1 to degrade dsDNA in the cell. Our data shows that TtCan1 has no sequence preference, suggesting that this nuclease might degrade the host genome leading to cell suicide. Therefore, cOA ratios generated by type III complexes might have evolved as a fine-tuned immune mechanism regulating ancillary nuclease activities and infection outcomes.

In the second iteration of the TtCsm-based SARS-CoV-2 diagnostic presented here, we increase the sensitivity of amplification-free viral detection 1000-fold and eliminate the RNA extraction step, significantly limiting sample handling. The improved assay detects SARS-CoV-2 directly in nasopharyngeal swabs at concentrations as low as $5 \times 10^4$ viral RNA copies per μL (Ct~21.2). Recent works have repurposed type III complexes of *Lactococcus lactis* (L1Csm) [Reference 18] and the *Vibrio metoecus* (VmeCmr) [Reference 24] to achieve ~2-4 fM ($1-2 \times 10^3$ copies/μL) sensitivity of SARS-CoV-2 detection in RNA samples. While these levels of sensitivity are still inferior to RT-qPCR, they are sufficient to identify infected individuals capable of spreading the virus [Reference 45] and comparable to rapid antigen tests [Reference 2]. We anticipate that further incorporating Type III-based RNA pull-down technique to bypass RNA extraction, optimizing sample lysis conditions, and using the next generation of readouts will further boost the sensitivity and minimize time-to-result, bringing type III CRISPR diagnostic to current standards of rapid molecular testing.

Methods (Examples)

Human Clinical Sample Collection and Preparation

Clinical samples were obtained with local IRB approval (protocol #DB033020) and informed consent from patients undergoing testing for SARS-CoV-2 Bozeman Health Deaconess Hospital. Nasopharyngeal swabs from patients that either tested negative or positive for SARS-CoV-2 were collected in viral transport media. RNA was extracted from all patient samples using QIAamp Viral RNA Mini Kit (QIAGEN).

Nucleic Acids

Sodium salt of cyclic di-, tri-, tetra-, penta- and hexaadenosine monophosphates (cA2-6) were purchased from Biolog Life Science Institute. Fluorescent reporters (RNA and DNA) were purchased from IDT (Table 1, SEQ ID NOS. 1-47). dsDNA reporter was made by heating and slow cooling of the 5'-FAM- and 3'-BHQ-labelled strands. Target and non-target RNAs of SARS-CoV-2 N-gene were in vitro transcribed with MEGAscript T7 (THERMO FISHER SCIENTIFIC) from PCR products generated from pairs of synthesized overlapping DNA oligos (Table 1, SEQ ID NOS. 1-47) (EUROFINS). Transcribed RNAs were purified by denaturing PAGE. Total RNA from HEK 293T cells was extracted using TRIzol reagent.

Non-Targeting Control (NTC)

Total RNA extracted from nasopharyngeal swabs previously tested negative for SARS-CoV-2 with RT-qPCR or total RNA extracted from HEK 293T cells were used as negative controls. RNA extracted from HEK 293T cells was diluted to match the average Ct level (~27) obtained for RNAseP mRNA in RNA samples extracted from nasopharyngeal swabs (Table 2). The RT-qPCR for RNase P mRNA was performed using CDC RP primers and probe (2019-nCoV CDC EUA Kit, IDT #10006606).

Plasmids

Plasmids pCDF-5xT7-TtCsm (Addgene #128572) and pACYC-TtCas6-4xcrRNA4.5 (Addgene #127764) encoding for *Thermus thermophilus* type III-A csm1-csm5 genes and CRISPR locus, respectively, were a gift from Jennifer Doudna. Vector pCDF-5xT7-TtCsm was used as a template for site-directed mutagenesis to mutate the D33 residue in Csm3 to alanine (D33A) and inactivate Csm3-mediated cleavage of target RNA (pCDF-5xT7- TtCsm$^{Csm3-D34A}$) [Reference 35]. The CRISPR array in pACYC-TtCas6-4xcrRNA4.5 was replaced with a synthetic CRISPR array (GeneArt) containing five repeats and four identical spacers, designed to target the N-gene of SARS-CoV-2 (i.e., pACYC-TtCas6-4xgCoV2N1) [Reference 16]. TtCas6 was PCR was PCR-amplified from the pACYC-TtCas6-4xcrRNA4.5 plasmid and cloned between the NcoI and XhoI sites in the pRSF-1b backbone (Millipore Sigma) (pRSF-TtCas6). Expression vector encoding TtCsm6 nuclease, pC0075 TtCsm6 His6-TwinStrep-SUMO-BsaI, was a gift from Feng Zhang (Addgene plasmid #115270) [Reference 46].

*E. coli* codon optimized dsDNA gene fragments encoding for Can1 from *Thermus thermophilus* (TtCan1; NCBI accession=WP_011229147.1), Can2 from Archaeoglobi archaeon JdFR-42 (AaCan2; (JGI) IMG gene accession=2730024700), *Clostridium thermobutyricum* (CtCan2; NCBI accession=WP_195972101.1), and *Thermus thermophilus* (TtCan2; NCBI accession=WP_143585921.1) were synthesized (GenScript) and cloned into pC0075 vector (Addgene #) in frame with the N-terminal His6- TwinStrep-SUMO tag using NcoI and XhoI restriction sites to replace the TtCsm6 gene. NucC from *Clostridium tepidum* BSD2780120874b_170522_A10 (CtNucC; NCBI accession=WP_195923598.1), *Elioraea* sp. Yellowstone (EsNucC; NCBI accession=WP_141855040.1) and Acidimicrobiales bacterium mtb01 (Amtb01NucC; NCBI accession=TEX45487.1), were cloned into pC0075 backbone using the same restriction sites as for Can1 and Can2 genes.

Protein Expression and Purification

Expression and purification of the TtCsm$^{Csm3-D34A}$ complex and TtCsm6 were performed as previously described [Reference 16]. To express and purify ancillary nucleases (TtCan1, AaCan2, CtCan2, TtCan2, CtNucC, EsNucC, and Amtb01NucC) the following protocol was used. The protein expression vector was transformed into *Escherichia coli* BL21(DE3) cells and grown in LB Broth (Lennox) (Thermo Fisher Scientific) at 37° C. to an OD600 of 0.5. Cultures were then incubated on ice for 1 hour, and then induced with 0.5 mM IPTG for overnight expression at 16° C. Cells were lysed with sonication in Lysis buffer (20 mM Tris-HCl pH 8, 500 mM NaCl, 1 mM TCEP) and lysate was clarified by centrifugation at 10,000 g for 25 mins, 4° C. The lysate was heat-treated at 55° C. for 45 minutes and clarified by centrifugation at 10,000 g for 25 minutes at 4° C. His6-TwinStrep-tagged protein was bound to StrepTrap HP column (Cytiva) and washed with Lysis buffer. The protein was eluted with Lysis buffer supplemented with 2.5 mM desthiobiotin and concentrated (10 k MWCO Corning Spin-X concentrators) at 4° C. Affinity tags were removed from the protein using His-tagged SUMO protease (100 µL of 2.5 mg/mL protease per 20 mg of protein) during dialysis against SUMO digest buffer (30 mM Tris-HCl pH 8, 500 mM NaCl,1 mM DTT, 0.15% Igepal) at 4° C. overnight. To remove the tag and the protease, dialyzed protein was applied to HisTrap HP column (Cytiva), and the flow-through was concentrated using Corning Spin-X concentrators at 4° C. Finally, the protein was purified using a HiLoad Superdex 200 26/600 size-exclusion column (Cytiva) in storage buffer)20 mM Tris-HCl pH 7.5, 1 mM DTT, 400 mM monopotassium glutamate, 5% glycerol). Fractions containing the target protein were pooled, concentrated, aliquoted, flash frozen in liquid nitrogen, and stored at −80° C.

P32-Labeling of RNA Oligos

Target (SARS-CoV-2 N1) and non-target RNAs were transcribed from PCR extended duplex oligos using homemade T7 RNA polymerase (Table 1, SEQ ID NOS. 48-51) (EUROFINS). The IVT RNAs were gel purified and dephosphorylated with Quick CIP (NEB) for 20 min at 37° C. in 1× CutSmart Buffer (NEB). The phosphatase was inactivated by heating at 80° C. for 5 min before 5' end-labeling the RNAs with T4 polynucleotide kinase (NEB) and [γ-$^{32}$P]-ATP (PerkinElmer) for 30 min at 37° C. The kinase was heat inactivated by heating at 65° C. for 20 minutes.

Binding and pull-down of RNA oligos with TtCsm. For the experiments shown in FIGS. 5B and 9B, 9C, P32-labeled RNA oligos (25 nM) were incubated with TtCsm$^{Csm3-D34A}$ (160 nM) targeting SARS-CoV-2 N-gene in 1× Binding Buffer (25 mM HEPES, pH 7.5, 150 mM NaCl, 1 mM TCEP) for 20 min at 65° C. The reaction mixtures were added to 10 µL of HisPur Ni-NTA Magnetic beads (ThermoFisher) equilibrated in Binding Buffer and incubated on ice 30 min with vortexing every 10 minutes. The beads were separated from the supernatant using a magnet and washed with 50 µL 1× binding buffer. The RNA was extracted from supernatant (unbound fraction) and beads (bound fraction) using Acid Phenol: chloroform (Ambion). Extracted RNA was resolved using UREA-PAGE, exposed to a phosphor screen, and imaged on Typhoon imager (Amersham). Bands corresponding to the IVT RNAs were quantified using ImageJ and the percent bound calculated [bound/(bound+free)*100%].

Complexing of TtCsm with Magnetic Beads

The HisPur Ni-NTA Magnetic beads (ThermoFisher) were washed two times with a 1× Binding Buffer (25 mM HEPES, pH 7.5, 150 mM NaCl, 1 mM TCEP). For one reaction, 5 µL of equilibrated beads were mixed with TtCsm$^{dead}$ complex (25 nM) in 1× Binding Buffer (V=50 µL) and incubated for 30 min on ice. The beads with the complex (Csm-beads) were concentrated with a magnet and resuspended in 5 µL of 1× Binding Buffer.

Thin-Layer Chromatography (TLC)

For the experiments shown in FIGS. 5C, 3 µL of positive sample (target RNA diluted in NTC, 10$^{10}$ copies/µL) or 3 µL of NTC were mixed with TtCsm Csm3-D34A complex (25 nM) and 250 uM ATP supplemented with [α-$^{32}$P]-ATP (PerkinElmer) in the reaction buffer (20 mM Tris-HCl pH 7.8, 250 mM monopotassium glutamate, 10 mM ammonium sulfate, 1 mM TCEP (tris(2-carboxyethyl)phosphine)), 5 mM magnesium sulfate). The reaction was incubated at 60° C. for 1 h. For the pull-down reactions, 120 µL of positive or negative samples were mixed with 5 µL of Csm-beads in Binding Buffer (25 mM HEPES, pH 7.5, 150 mM NaCl, 1 mM TCEP) for 10 min at 60° C. The Csm-beads were concentrated with a magnet and the supernatant was discarded. The Csm-beads pellets were resuspend in 30 µL of the reaction buffer 250 uM ATP supplemented with [α-$^{32}$P]-ATP (PerkinElmer). Reaction products were phenol-chloroform extracted and resolved on silica TLC plates (Millipore).

Samples (1 µL) were mixed with 100 mM sodium acetate, pH 5.2 (2 µL) and spotted 1.5 cm above the bottom of the TLC plate. The plate was placed inside a 2 L beaker filled to ~0.5 cm with developing solvent (0.2 M ammonium bicarbonate pH 9.3, 70% ethanol and 30% water) and capped with aluminum foil. The plate was run for 2 h at room temperature and dried. TLC plate was exposed to a phosphor screen and imaged with Typhoon phosphor imager. Chemically synthesized standards (2 uM) were resolved on the same TLC plate and visualized using UV shadowing.

To test cA3 and cA4 hydrolysis in the presence of ancillary nuclease, radiolabeled cA3 and cA4 produced above were mixed with nuclease (500 nM) in the reaction buffer and incubated for 1 hour at 55° C. Reaction products were phenol-chloroform extracted and resolved using thin-layer chromatography (TLC) for 45 min as described above.

Type III-Based RNA Detection

3 µL of RNA sample was mixed with 250 uM ATP, 25 nM TtCsm$^{dead}$ complex, 300 nM of nuclease (TtCsm6, AaCan2, or CtNucC) with corresponding reporter in a reaction buffer (20 mM Tris-HCl pH 7.8, 250 mM monopotassium glutamate, 10 mM ammonium sulfate, 1 mM TCEP (tris(2-carboxyethyl)phosphine)), 5 mM magnesium sulfate (for TtCsm6 and CtNucC) or 5 mM manganese(II) chloride (for AaCan2) in a 30 µL reaction. The reporter B8 (300 nM) was used for the reaction with TtCsm6, D7 (300 nM)—with AaCan2, and dsDNA probe (300 nM)—with CtNucC. Reactions were incubated at 55° C. Cleavage of fluorescent reporters was detected by measuring fluorescence every 10 sec in a real-time PCR instrument QuantStudio 3.

Type III-Based RNA Pull-Down and Detection

To bind TtCsm$^{dead}$ complex with the magnetic beads, the HisPur Ni-NTA Magnetic beads (ThermoFisher) were washed two times with a 1× Binding Buffer (25 mM HEPES, pH 7.5, 150 mM NaCl, 1 mM TCEP). For one reaction, 5 µL of equilibrated beads were mixed with TtCsm$^{dead}$ complex (30 nM) in 1× Binding Buffer (V=50 µL) and incubated for 30 min on ice. The beads with the complex (Csm-beads) were concentrated with a magnet and resuspended in 5 µL of 1× Binding Buffer.

Pull-down and detection from RNA sample: 120 µL of sample was mixed with 5 µL of Csm-beads in 1× Binding Buffer for 10 min at 60° C. The Csm-beads were concentrated with a magnet and the supernatant was discarded. The Csm-beads pellet was resuspended in 20 µL of the 1× reaction buffer (20 mM Tris-HCl pH 7.8, 250 mM monopotassium glutamate, 10 mM ammonium sulfate, 1 mM TCEP (tris(2-carboxyethyl)phosphine)), 5 mM magnesium sulfate/manganese(II) chloride) containing ATP (250 uM). The reaction was incubated 10 min at 60° C., the Csm-beads were pelleted, and the supernatant (10 µL) was transferred to a new reaction with TtCsm6 (300 nM) and B8 RNA Reporter (300 nM) or AaCan2 (300 nM) and D7 RNA Reporter (300 nM) in 1× reaction buffer (V=30 µL). Reactions were incubated at 55° C. Cleavage of the fluorescent RNA reporter was detected by measuring fluorescence every 10 sec in a real-time PCR instrument QuantStudio 3.

Pull-down and detection from nasopharyngeal swab: 120 µL of a nasopharyngeal swab was mixed with 5 µL of Csm-beads in 1× Lysis Buffer and incubated for 20 min at 65° C. Ten lysis buffers compositions were tested. All buffer contained 25 mM HEPES, pH 7.5, 150 mM NaCl, 1 mM TCEP and were supplemented with (A) 0.025% Triton X-100, (B) 0.025% Triton X-100 and 1 mM EDTA, (C1) 0.025% Triton X-100 and 1 mM EGTA, (C2) 0.05% Triton X-100 and 1 mM EGTA, (C3) 0.1% Triton X-100 and 1 mM EGTA, (I) 0.025% NP-40, (J) 0.025% NP-40 and 1 mM EDTA, (K1) 0.025% NP-40 and 1 mM EGTA, (K2) 0.05% NP-40 and 1 mM EGTA, or (K3) 0.1% NP-40 and 1 mM EGTA. The Csm-beads were concentrated with a magnet and the supernatant was discarded. The Csm-beads pellet was resuspended in 20 µL of the 1× reaction buffer (20 mM Tris-HCl pH 7.8, 250 mM monopotassium glutamate, 10 mM ammonium sulfate, 1 mM TCEP (tris(2-carboxyethyl)phosphine)), 5 mM magnesium sulfate/manganese(II) chloride) containing ATP (250 uM). The reaction was incubated 10 min at 65° C., the Csm-beads were pelleted, and the supernatant (10 µL) was transferred to a new reaction with TtCsm6 (300 nM) and B8 RNA Reporter (300 nM) or AaCan2 (300 nM) and D7 RNA Reporter (300 nM) in 1× reaction buffer (the final volume of a reaction 30 µL). Reactions were incubated at 55° C. Cleavage of fluorescent RNA reporter was detected by measuring fluorescence every 10 sec in a real-time PCR instrument QuantStudio 3.

RT-qPCR

RT-qPCR was performed using N1 and RP CDC primers (2019-nCoV CDC EUA Kit, IDT #10006606). RNA was extracted from patient samples with QIAamp Viral RNA Mini Kit (QIAGEN, #52906) and used for one-step RT-qPCR in ABI 7500 Fast Real-Time PCR Syste according to CDC guidelines and protocols (https[colon][doubleslash]www[dot]fda[dot]gov[slash]media[slash]134922[slash]download). In brief, 20 µL reaction included 8.5 µL of Nuclease-free Water, 1.5 µL of Primer and Probe mix (IDT, 10006713), 5 µL of TaqPath 1-Step RT-qPCR Master Mix (ThermoFisher, A15299) and 5 µL of the RNA. Nuclease-free water was used as negative template control (NTC). Amplification was performed as follows: 25° C. for 2 min, 50° C. for 15 min, 95° C. for 2 min followed by 45 cycles of 95° C. for 3 s and 55° C. for 30 s. To quantify viral RNA in the samples, standard curve for N1 primers was generated using a dilution series of a SARS-CoV-2 synthetic RNA fragment (RTGM 10169, NIST) spanning N gene with concentrations ranging from 10 to $10^6$ copies per µL. Three technical replicates were performed at each dilution. The NTC showed no amplification throughout the 45 cycles of qPCR.

Nanopore Sequencing of DNA Cleavage Fragments

DNA cleavage fragments were sequenced using Oxford Nanopore with Ligation Sequencing Kit (SQK-LSK109). After incubation with TtCan1 or NucC nucleases, cleavage fragments were column-purified using DNA Clean & Concentrator-5 kit (Zymo Research, D4004) as instructed. Next, for each sample 50 ng of purified DNA was used to prepare sequencing libraries with NEBNext® Ultra™ II DNA Library Prep Kit (NEB, E7645S). Briefly, DNA was end-repaired with NEBNext Ultra II End Prep Enzyme Mix, which fills 5'- and removes 3'-overhangs. Next, end-repaired fragments were barcoded with Native Barcoding Expansion kit (ONT, EXP-NBD104) using Ultra II Ligation Master Mix (NEB). Barcoded DNA fragments were pooled together and purified with magnetic beads (Omega Bio-tek, M1378-01). Freshly mixed 80% ethanol was used to wash magnetic bead pellet. Sequencing adapters (AMII) were ligated to barcoded DNA using NEBNext® Quick Ligation Module (NEB, E6056S). Ligation reactions were purified with magnetic beads. SFB buffer (ONT, EXP-SFB001) was used for washes. Resulting DNA library was eluted from the beads in 20 µL of EB buffer (QIAGEN, #19086). DNA concentration was measured with Qubit dsDNA HS Assay (ThermoFisher, Q32851), and 20 ng was loaded on the Nanopore MinION (R9.4.1 flow cell). The flow cell was primed, and library was loaded according to Oxford Nanopore protocol (SQK-LSK109 kit). The sequencing run was performed in the high-accuracy base calling mode in the MinKNOW software.

Sequencing Data Analysis

Base called reads were demultiplexed using guppy-barcoder (ONT) and aligned with minimap2 v2.17-r954-dirty (ax map-ont mode) to the reference plasmid sequence that was modified by adding 1000 bp overlaps at the 5'- and 3'-ends. Overlapping regions were introduced to account for circular nature of the plasmid. Resulting alignments (BAM files) were sorted and indexed using samtools v1.13. Next, bamtobed function in bedtools package was used to generate BED files and read coordinates were extracted. Oxford Nanopore platform reads through a more than a hundred kilobase pairs long DNA sequences47. Therefore, we regarded generated reads as complete sequences of cleavage fragments and read ends as cut sites. Read end coordinates were used to calculate cleavage fragment length distributions and map frequencies of cuts at specific locations (FIG. 15). To analyze sequence preference of nucleases, 14 bp windows surrounding read ends were extracted with getfasta function from bedtools package. Resulting fasta files were used to calculate position weigh matrices (PWMs) with getPwmFromFastaFile( ) function in DiffLogo R package. Finally, PWMs were plotted as sequence logos using ggseqlogo R package. Sequencing depth around the most frequent cut site for each nuclease was calculated with samtools depth function and plotted with ggplot2 package in RStudio.

RNA Reporter's Library

To determine the optimal RNA reporter for each cOA-activated nuclease, we constructed a library of variable RNA sequences tethering a FAM fluorophore to an Iowa Black quencher. These reporters were designed as single-stranded RNA molecules (i.e., 5'-FAM-AUNNNNNNAU-IABkFQ-3'; variable region underlined) or to produce a structured RNA (e.g., 5'-FAM-CGCGNNNNNNCGCG-IABkFQ-3'; variable region underlined). The Biostrings package in R was used to construct a library of reporter sequences containing each of the 64 unique trinucleotide combinations possible. Since multiple unique trinucleotides could be included in a single reporter (e.g. 5'-FAM-AUA-GAAGAAU-IABkFQ-3' contains AGA, GAA and AAG), we narrowed our initial library of 64 reporters to remove redundant sequences. This resulted in a library of 24 unique reporter sequences, each of which were integrated into both a single-stranded RNA reporter and a structured RNA reporter (Table 1). The R-script used to design these reporters is accessible on GitHub (WiedenheftLab/RNA_reporter_design).

In Vitro DNA and RNA Cleavage Assays

All reactions were performed in a buffer containing 20 mM Tris-HCl pH 7.8, 250 mM monopotassium glutamate, 10 mM ammonium sulfate, 1 mM TCEP, 5 mM magnesium sulfate or 5 mM manganese chloride. Plasmid DNA cleavage assays were performed by incubating 1 µg of Lenti-luciferase-P2A-Neo (Addgene #105621) plasmid with TtCan1, AaCan2 or CtNucC (15-200 nM) in the presence of cOAx (15-45 nM) in 10 µL reaction. After 5-15 min incubation at 60° C. for TtCan1 and 55° C. for both AaCan2 and CtNucC, Gel Loading Dye, Purple (6×) (NEB) was added and 4 µL was loaded on 1% agarose gel. For ssDNA and ssRNA cleavage assays, 0.425 uM of 71 nt DNA oligo (CGTCGTACCGGTTAGAG-GATGGTGCAAGCGTAATCTGGAA-CATCGTATGGGTATG CCCACGGTGTCCACGGCG, Eurofins) or 0.425 uM of 74 nt IVT RNA SARS-CoV-2 N-gene (Table 1, SEQ ID NOS. 48-51) were incubated with TtCan1 (200 nM) or AaCan2 (200 nM) in the presence of cOAx (20-45 nM) in 10 µL. After 5-15 min incubation at 60° C. for TtCan1 and at 55° C. for AaCan2, 2×RNA Loading Dye (NEB) was added and 10 µL was loaded on 12% UREA PAGE.

Phylogenetic Analysis of Can1 and Can2 Proteins

A DELTA-BLAST was initiated, using previously described Can1 and Can2 proteins as queries29-31 to generate individual lists of closely related proteins with an e-value cutoff of 10-4 and 50% query coverage. The resulting sequences were then used as queries to initiate a PSI-BLAST search with an e-value cutoff of 10-4 and 50% query coverage. This step was repeated until convergence and redundant sequences were removed with CD-HIT v4.748. Can1 sequences, which contain two CARF domains and a nuclease domain, were also retrieved from a previously published dataset14 and were merge with non-redundant sequences identified via PSI-BLAST to generate multiple sequence alignments. In total, 29 sequences of Can1-related proteins and 2,531 sequences of Can2-related proteins were used separately to generate multiple sequence alignment with a local version of MAFFT v7.42949 (--localpair --maxiterate 1000). The generated alignments for Can1 and Can2 were curated with MaxAlign v1.150 to remove misaligned or non-homologous sequences. The resulting dataset—comprised of 29 Can1-like and 1,283 Can2-like proteins, respectively—were then individually realigned with MAFFT and HMMbuild51 (HMMER v3.2.1) was used to generate HMM profiles from each alignment. The resulting profiles were used to search a local database of prokaryotic genomes from NCBI (downloaded on Jun. 11, 2021). An initial search performed with these HMM profiles identified 1,442 Can1 and 5,431 Can2 homologs, which were manually filtered according to the presence of domains that define each protein, as well as the presence of conserved residues found in CARF and nuclease domains. The resulting set of 204 Can1 and 3,121 Can2 proteins were merged into a single file and aligned in MAFFT (LINSI option) for downstream phylogenetic analyses. Next, Trimal v1.452 was used to remove columns in the alignment comprised of ≥70% gaps. ProtTest v3.4.253 was used to select an evolutionary model, and a phylogenetic tree was constructed in IQ-TREE v1.6.154 using the recommended model (i.e., LG+G+F). The phylogenetic tree was plotted using the ggTree package in R55.

Phylogenetic Analysis of NucC

A phylogenetic tree of NucC proteins was generated using the same methods as described above for Can1/Can2 proteins. Briefly, DELTA-BLAST and PSI-BLAST searches with previously identified NucC proteins [Reference 32]

generated a list of closely related proteins (e-value cutoff of 10-4 and minimum 50% query coverage). The resulting dataset was filtered with CD-HIT v4.7 to remove redundant sequences. The resulting 1,230 NucC sequences were aligned with MAFFT (--localpair --maxiterate 1000), and poorly aligned and highly gapped sequences were removed with MaxAlign. The resulting set of 896 NucC sequences were re-aligned with MAFFT as previously described, and the resulting alignment was used to generate a NucC HMM profile which we used to search within prokaryotic genomes from NCBI. This search identified 1,774 hits, which were filtered according to the presence of restriction endonuclease-like domain (i.e., IDx30EAK-motif containing), gate-loop and cA3 binding domains and were aligned with MAFFT. The resulting alignment of 1,510 NucC proteins was used to generate a phylogenetic tree with FastTree v2.1.1056 and was plotted using the ggTree package in R.

Quantification and Statistical Analysis

All statistical analyses were performed in RStudio. Analysis of Variance Models (ANOVA) were calculated with aov( ) function in stats R package. Multiple comparisons between positive samples and negative controls were performed using Dunnett's test with multcomp R package. Reaction slopes were determined by extracting coefficients from linear models fitted to fluorescence data with lm( ) function in R. The linear regions of the fluorescence curves were identified using rolling regression with auto_rate( ) function in respR package. Patient samples (n=17) for viral detection assays were randomly selected from a sample database (n=858) with base R function sample( ).

Statistical threshold for detecting SARS-CoV-2 in patient samples with Csm-based assay was set as mean of negative control ±2.33 SD, which captures 98% of variation in negative samples (2% false positive). Samples with z-score>2.33 were considered positive for SARS-CoV-2. Z-scores were calculated in R using following formula: $Z=(F_{sample}-\mu_{neg})/\sigma_{neg}$, where $F_{sample}$ is fluorescence measured in a sample, $\mu_{neg}$ is mean of negative control, $\sigma_{neg}$ is standard deviation of negative control. Statistical significance levels used in the figures are * $p<0.001$,  $p<0.01$, and * $p<0.05$.

Lateral-Flow Based Readouts of Type III CRISPR Diagnostics

Type III CRISPR-Based RNA Detection with Lateral-Flow Assay Readout.

Figure 24:
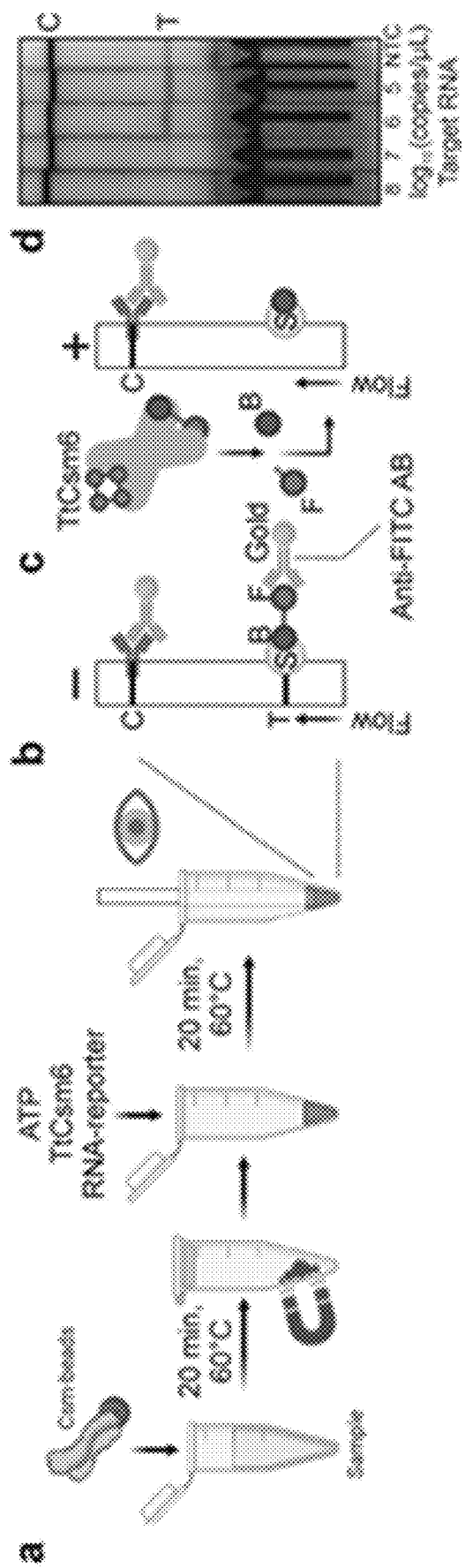
FIG. 24 shows a schematic flow of TtCsm-based RNA capture assay coupled with one-pot ATP polymerization and TtCsm6-based RNA reporter cleavage detected by lateral-flow paper-based readout.

FIG. 24 shows a schematic flow of TtCsm-based RNA capture assay coupled with one-pot ATP polymerization and TtCsm6-based RNA reporter cleavage detected by lateral-flow paper-based readout. At panel b, in a negative sample (-), RNA reporter labeled with FITC (F) and biotin (B) migrates through the dipstick and binds to streptavidin (S) embedded in the test strip (T). Gold-labeled anti-FITC antibodies (AB) bind FITC on the immobilized reporter and accumulate at the test line. Excess unbound gold particles conjugated to anti-FITC AB are captured by secondary antibodies at the control (C) line. Both C and T lines appear.

At panel c, if TtCsm$^{Csm3-D34A}$ detects target RNA (+) and polymerizes ATP, cA4-activated TtCsm6 cleaves RNA reporter and releases FITC (F) from biotin (B). All anti-FITC Abs migrate to the control line and the test line remains uncolored. At panel d, an lateral-flow assay is used to detect SARS-CoV-2 N-gene RNA diluted in total human RNA (HEK 293T cells) as shown in panel a.

Figures 25A, 25B:
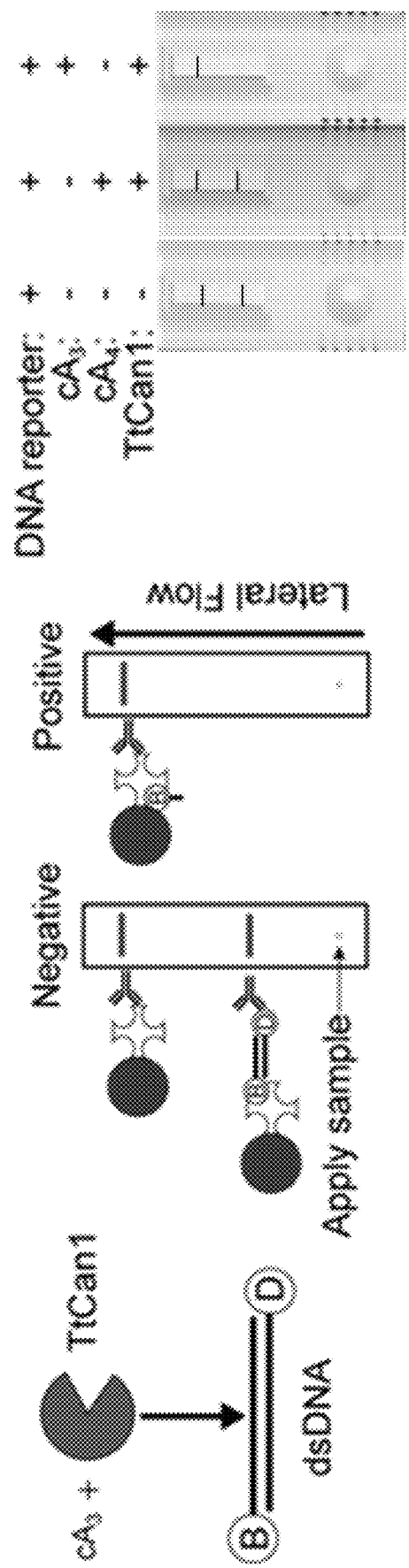
FIG. 25A shows a schematic of type III CRISPR-based RNA detection with lateral-flow assay readout using a DNA reporter.
FIG. 25B shows a proof of concept that shows a solution containing either DNA reporter alone, or a DNA reporter mixed with 10 nM cA4 and TtCan1 at 50° C. for 5 minutes, results in both a low and high band on the lateral flow strip, a negative result, but DNA reporter mixed with 10 nM cA3 and TtCan1 at 50° C. for 5 minutes gives a positive result instead.

FIG. 25A shows a schematic of type III CRISPR-based RNA detection with lateral-flow assay readout using a DNA reporter. Schematic of proof-of-concept that shows how cA3 produced by a type III CRISPR-based diagnostic activates the ancillary DNase TtCan1 to cleave a 2 Kb DNA reporter labelled biotin (B) and digoxigenin (D). In a negative (no cA3 produced) sample, the DNA reporter remains intact and indirectly tethers streptavidin-coated gold nanoparticles to a line of anti-digoxigenin antibodies embedded in the lateral flow strip, forming a deep purple line. Excess streptavidin-coated gold nanoparticles are wicked up the lateral flow strip and are captured by an embedded line of anti-streptavidin antibodies, forming a second deep purple line. In a positive sample, the DNA reporter is degraded, therefore all the streptavidin-coated gold nanoparticles are wicked upwards to the control line of anti-streptavidin antibodies.

FIG. 25B shows a proof of concept that shows a solution containing either DNA reporter alone, or a DNA reporter mixed with 10 nM cA4 and TtCan1 at 50° C. for 5 minutes, results in both a low and high band on the lateral flow strip, a negative result, but DNA reporter mixed with 10 nM cA3 and TtCan1 at 50° C. for 5 minutes gives a positive result instead. But incubation of the DNA reporter with 10 nM cA3 and TtCan1 at 50° C. for 5 minutes, results in rapid degradation of the DNA reporter and the disappearance of the low band on the lateral flow strip, a positive result.

FIG. 26A shows an example of a workflow to identify a conserved protospacer flanking sequence specific to a subset of type III CRISPR surveillance complexes. Type III CRISPR loci with repeats that are more than 80% similar to the repeat found in the CRISPR locus that is associated with the type III-A TtCsm complex were collated. Spacers in these similar type III CRISPR loci were extracted and the original protospacer target sequences were identified using the CRISPRTarget program. Redundant protospacer sequences were removed, and the 3' flanking regions were analyzed by the MEME motif discovery tool to identify a putative PFS.

FIG. 26B shows an example of the PFS identified by MEME for a subset of 157 protospacer sequences (left) and for all protospacer sequences (right).

The protospacer flanking sequence and length affects ATP polymerization by type III CRISPR surveillance complexes.

FIG. 27A shows a schematic of the Calcein-based assay to measure ATP polymerization by target-RNA bound type III CRISPR surveillance complexes. PPi (pyrophosphate) is a by-product of ATP polymerization. PPi chelates Manganese ions, which causes Calcein to bind to Magnesium ions instead, leading to an increase in fluorescent signal.

FIG. 27B shows plots of Calcein-based assays to measure ATP polymerization by the "N9" guided TtCsm complex mixed with $10^{10}$ copies of one of six different target RNA sequences.

FIG. 27C shows a schematic that describes the differences in the PFS between each of the otherwise identical six target RNA sequences.

Discussion of FIGS. 24-27

The Type III CRISPR-Cas systems have recently been repurposed for sequence-specific detection of SARS-CoV-2 genomic RNA. Here, we show that type III CRISPR diagnostics can be modified for a lateral-flow-based readout.

The binding of Type III surveillance complexes to target RNA, activates two activities in the Cas10 subunit, an HD nuclease activity and a polymerase activity. The activated Cas10 subunit polymerizes nucleotide triphosphates (e.g., ATP) into a mixture of linear (e.g., Ax, where "x" is the number of adenosines in the polymer) and cyclic oligonucleotides (cAx).

Cyclic oligoadenylates can be indirectly measured by the activation of effectors with different enzymatic activities (e.g. nucleases, peptidases, pore-forming toxins). The activity of nucleases [References 57-60] and peptidases can be measured by cleavage of an RNA, DNA or peptide tether that is labelled i) on either end with a fluorophore-quencher pair (cleavage detected by bulk fluorescence or digital enzymology), ii) on either end with a fluorophore and/or digoxigenin and/or biotin (cleavage detected by lateral flow, surface-enhanced Raman spectroscopy lateral flow), iii) with multiple gold nanoparticles (cleavage detected by bulk colorimetric or digital enzymology), iv) on one end with a redox-active molecule (e.g., methylene blue) and linked on the other end to a gold electrode (cleavage detected by amperometric bio sensor).

After type III CRISPR-based capture and concentration of target RNA from a complex sample (FIG. 24A), the beads containing type III surveillance complex bound to target RNA are resuspended in a buffer containing ATP, the cA4-activated nuclease TtCsm6 and an RNA reporter containing a Biotin label on one end and a FITC (Fluorescein isothiocyanate) label on the other end. The resuspension is incubated at 60° C. for 20 minutes, and then applied to the starting end of a lateral flow strip. The starting end of the lateral flow strip contains gold-labelled anti-FITC antibodies, which are wicked up the lateral flow strip along with RNA reporter. As the solution migrates up the lateral flow strip it passes through an embedded and immobile line of streptavidin protein (the test line), which captures any biotin and biotin-labelled RNA (FIG. 24B). Any intact RNA that has retained both a biotin label and a FITC label, thereby indirectly traps anti-FITC gold-labelled antibodies at the test line, which appears as a dark band. The solution continues to wick up the lateral flow strip and carries excess gold-labelled antibodies that are captured at an embedded and immobile line of antibodies that bind to the gold-labelled antibodies (the control line), which appears as a dark band.

There is often a concern of RNase contamination when non-experts perform diagnostic assays which may lead to a false positive result in diagnostics that rely on RNA reporters. To get around this issue we can repurpose ancillary DNases that are activated by the cyclic oligoadenylates synthesized by type III CRISPR surveillance complexes. As a proof-of-concept, we show that low amounts (10 nM) of pure cA3 activate TtCan1 to rapidly (5 minutes) cleave a DNA reporter labelled with biotin and digoxigenin (FIGS. 25A, 25B). In this design of the DNA reporter and lateral flow strip, a negative result is readout as both a low and high band appearing on the strip (FIG. 25A). Whereas when TtCan1 is activated by cA3 (one of the cyclic oligoadenylates produced by target RNA-bound type III CRISPR surveillance complexes), the DNA reporter is cleaved, and streptavidin-coated gold nanoparticles are no longer indirectly tethered to the lower line of anti-digoxigenin antibodies embedded in the lateral flow strip (FIG. 25B).

The sequence and length of the Protospacer Flanking Sequence impacts ATP polymerization by type III CRISPR surveillance complexes The sequence identity of nucleotides located downstream (3') of the protospacer sequence can impact the production of cyclic oligoadenylates by target RNA-bound type III CRISPR surveillance complexes [References 61, 62]. Here, we computationally predict the protospacer flanking sequences (PFS) for one type III CRISPR surveillance complex (TtCsm) and experimentally test the impact of PFS sequences on Cas10-mediated polymerization, by measuring pyrophosphate production using a Calcein-based assay.

A PFS motif that is predicted to stimulate the Cas10 polymerase of the TtCsm type III CRISPR surveillance complex was bioinformatically identified by collating a list of type III CRISPR arrays with repeats similar (80% sequence identity) to the CRISPR repeat associated with the TtCsm complex (FIG. 26A). The spacers found in these CRISPR loci that are similar to the TtCsm CRISPR locus were then extracted and the original targeted nucleic acid sequences (protospacers) were identified. Redundant protospacers were removed. The 3' ends of the protospacers were then analyzed using a motif discovery tool called MEME 7. A predicted stimulatory PFS for TtCsm complex is approximately six nucleotides long (FIG. 26B).

The polymerization of ATP into cyclic oligoadenylates by target RNA-bound type III CRISPR surveillance complexes can be measured with a Calcein-based assay 8 (FIG. 27A). To determine the effect of the PFS on ATP polymerization, Calcein-based assays were used to measure ATP polymerization by a single TtCsm complex (termed "N9") mixed with one of six different target RNAs (FIG. 27C). In an original biochemical screen of 10 TtCsm complexes purified with 10 different RNA guides, two RNA guides performed best, termed "N1" and "N9" [Reference 64]. However, the biochemical reason for why these two RNA guides performed best is unknown. Here we show that the original N9 target RNA has a PFS that stimulates robust ATP polymerization that is on par with targets containing two versions of the predicted PFS (either no base pairing, or base pairing at position—5). Conversely a target RNA with a PFS that corresponds to sequences that are not typically found downstream of the protospacers in natural systems, are not able to efficiently stimulate ATP polymerization by TtCsm. Both the lack of a flanking sequence 3' of the complementary region or a flanking sequence that is fully complementary to the 5' handle of the crRNA-guide inhibit ATP polymerization by TtCsm. Therefore, type III CRISPR-based diagnostics of small RNAs (e.g., miRNAs) require short guide RNAs be designed such that an approximately six nucleotide 3' PFS remains in the target RNA. Therefore, type III CRISPR-based diagnostics of small RNAs will require the use of natural or designed type III CRISPR systems that assemble around short guide RNAs.

Collectively, these results enable the design of sensitive crRNA-guides which target sequences with PFSs that stimulates robust cyclic oligoadenylate production by the type III CRISPR surveillance complex. Second, the design of specific guide RNA sequences will be assisted by ensuring that off-target RNAs have a PFS that inhibits cyclic oligoadenylate production. Third, robust detection of short RNA sequences (e.g., microRNAs, siRNAs, etc.) via methods that require Cas10-mediated polymerase activity will require a PFS.

TABLE 1

Sequence Listing. Fluorescent RNA and DNA reporters in which variable regions of sequence are underlined. All sequences each have 5-Carboxyfluorescein (FAM) dye at the 5' end. SEQ ID NOS. 1-46 each have Iowa Black FQ quencher (IABkFQ) at the 3' end. SEQ ID NO. 47 has Black Hole Quencher (BHQ) dye at the 3' end. SEQ ID NOS. 48-51 include oligonucleotide primers used to generate DNA templates for in vitro transcription with T7 polymerase.

| SEQ ID NO. | Sequence | Description |
|---|---|---|
| 1 | 5'-FAM-AU<u>AAAAAAA</u>AU-IABkFQ | ssRNA Reporter (Variable region underlined); Trinucleotides: AAA; class: non-structured |
| 2 | 5'-FAM-AU<u>AACAAC</u>AU-IABkFQ | ssRNA Reporter (Variable region underlined); Trinucleotides: AAC, ACA, CAA; class: non-structured |
| 3 | 5'-FAM-AU<u>AAGAAG</u>AU-IABkFQ | ssRNA Reporter (Variable region underlined); Trinucleotides: AAG, AGA, GAA; class: non-structured |
| 4 | 5'-FAM-AU<u>AAUAAU</u>AU-IABkFQ | ssRNA Reporter (Variable region underlined); Trinucleotides: AAU, AUA, UAA; class: non-structured |
| 5 | 5'-FAM-AU<u>ACCACC</u>AU-IABkFQ | ssRNA Reporter (Variable region underlined); Trinucleotides: ACC, CCA, CAC; class: non-structured |
| 6 | 5'-FAM-AU<u>ACGACG</u>AU-IABkFQ | ssRNA Reporter (Variable region underlined); Trinucleotides: ACG, CGA, GAC; class: non-structured |
| 7 | 5'-FAM-AU<u>ACUACU</u>AU-IABkFQ | ssRNA Reporter (Variable region underlined); Trinucleotides: ACU, CUA, UAC; class: non-structured |
| 8 | 5'-FAM-AU<u>AGCAGC</u>AU-IABkFQ | ssRNA Reporter (Variable region underlined); Trinucleotides: AGC, GCA, CAG; class: non-structured |
| 9 | 5'-FAM-AU<u>AGGAGG</u>AU-IABkFQ | ssRNA Reporter (Variable region underlined); Trinucleotides: AGG, GGA, GAG; class: non-structured |
| 10 | 5'-FAM-AU<u>AGUAGU</u>AU-IABkFQ | ssRNA Reporter (Variable region underlined); Trinucleotides: AGU, GUA, UAG; class: non-structured |
| 11 | 5'-FAM-AU<u>AUCAUC</u>AU-IABkFQ | ssRNA Reporter (Variable region underlined); Trinucleotides: AUC, UCA, CAU; class: non-structured |
| 12 | 5'-FAM-AU<u>AUGAUG</u>AU-IABkFQ | ssRNA Reporter (Variable region underlined); Trinucleotides: AUG, UGA, GAU; class: non-structured |
| 13 | 5'-FAM-AU<u>AUUAUU</u>AU-IABkFQ | ssRNA Reporter (Variable region underlined); Trinucleotides: AUU, UUA, UAU; class: non-structured |
| 14 | 5'-FAM-AU<u>CCCCCCC</u>AU-IABkFQ | ssRNA Reporter (Variable region underlined); Trinucleotides: CCC; class: non-structured |
| 15 | 5'-FAM-AU<u>CCGCCG</u>AU-IABkFQ | ssRNA Reporter (Variable region underlined); Trinucleotides: CCG, CGC, GCC; class: non-structured |
| 16 | 5'-FAM-AU<u>CCUCCU</u>AU-IABkFQ | ssRNA Reporter (Variable region underlined); Trinucleotides: CCU, CUC, UCC; class: non-structured |
| 17 | 5'-FAM-AU<u>CGGCGG</u>AU-IABkFQ | ssRNA Reporter (Variable region underlined); Trinucleotides: CGG, GGC, GCG; class: non-structured |

TABLE 1-continued

Sequence Listing. Fluorescent RNA and DNA reporters in which variable regions of sequence are underlined. All sequences each have 5-Carboxyfluorescein (FAM) dye at the 5' end. SEQ ID NOS. 1-46 each have Iowa Black FQ quencher (IABkFQ) at the 3' end. SEQ ID NO. 47 has Black Hole Quencher (BHQ) dye at the 3' end. SEQ ID NOS. 48-51 include oligonucleotide primers used to generate DNA templates for in vitro transcription with T7 polymerase.

| SEQ ID NO. | Sequence | Description |
|---|---|---|
| 18 | 5'-FAM-AU<u>CGUCGUA</u>U-IABkFQ | ssRNA Reporter (Variable region underlined); Trinucleotides: CGU, GUC, UCG; class: non-structured |
| 19 | 5'-FAM-AU<u>CUGCUG</u>AU-IABkFQ | ssRNA Reporter (Variable region underlined); Trinucleotides: CUG, UGC, GCU; class: non-structured |
| 20 | 5'-FAM-AU<u>CUUCUU</u>AU-IABkFQ | ssRNA Reporter (Variable region underlined); Trinucleotides: CUU, UUC, UCU; class: non-structured |
| 21 | 5'-FAM-AU<u>GGUGGU</u>AU-IABkFQ | ssRNA Reporter (Variable region underlined); Trinucleotides: GGU, GUG, UGG; class: non-structured |
| 22 | 5'-FAM-AU<u>GUUGUU</u>AU-IABkFQ | ssRNA Reporter (Variable region underlined); Trinucleotides: GUU, UUG, UGU; class: non-structured |
| 23 | 5'-FAM-AU<u>UUUUUU</u>AU-IABkFQ | ssRNA Reporter (Variable region underlined); Trinucleotides: UUU; class: non-structured |
| 24 | 5'-FAM-CGCG<u>AAAAAA</u>CGCG-IABkFQ-3 | ssRNA Reporter (Variable region underlined); Trinucleotides: AAA; class: Structured |
| 25 | 5'-FAM-CGCG<u>AACAAC</u>CGCG-IABkFQ-3' | ssRNA Reporter (Variable region underlined); Trinucleotides: AAC, ACA, CAA; class: Structured |
| 26 | 5'-FAM-CGCG<u>AAGAAG</u>CGCG-IABkFQ-3' | ssRNA Reporter (Variable region underlined); Trinucleotides: AAG, AGA, GAA; class: Structured |
| 27 | 5'-FAM-CGCG<u>AAUAAU</u>CGCG-IABkFQ-3' | ssRNA Reporter (Variable region underlined); Trinucleotides: AAU, AUA, UAA; class: Structured |
| 28 | 5'-FAM-AUAU<u>ACCACC</u>AUAU-IABkFQ-3' | ssRNA Reporter (Variable region underlined); Trinucleotides: ACC, CCA, CAC; class: Structured |
| 29 | 5'-FAM-AUAU<u>ACGACG</u>AUAU-IABkFQ-3' | ssRNA Reporter (Variable region underlined); Trinucleotides: ACG, CGA, GAC; class: Structured |
| 30 | 5'-FAM-CGCG<u>ACUACU</u>CGCG-IABkFQ-3' | ssRNA Reporter (Variable region underlined); Trinucleotides: ACU, CUA, UAC; class: Structured |
| 31 | 5'-FAM-AUAU<u>AGCAGC</u>AUAU-IABkFQ-3' | ssRNA Reporter (Variable region underlined); Trinucleotides: AGC, GCA, CAG; class: Structured |
| 32 | 5'-FAM-AUAU<u>AGGAGG</u>AUAU-IABkFQ-3' | ssRNA Reporter (Variable region underlined); Trinucleotides: AGG, GGA, GAG; class: Structured |
| 33 | 5'-FAM-CGCG<u>AGUAGU</u>CGCG-IABkFQ-3' | ssRNA Reporter (Variable region underlined); Trinucleotides: AGU, GUA, UAG; class: Structured |
| 34 | 5'-FAM-CGCG<u>AUCAUC</u>CGCG-IABkFQ-3' | ssRNA Reporter (Variable region underlined); Trinucleotides: AUC, UCA, CAU; class: Structured |

TABLE 1-continued

Sequence Listing. Fluorescent RNA and DNA reporters in which variable regions of sequence are underlined. All sequences each have 5-Carboxyfluorescein (FAM) dye at the 5' end. SEQ ID NOS. 1-46 each have Iowa Black FQ quencher (IABkFQ) at the 3' end. SEQ ID NO. 47 has Black Hole Quencher (BHQ) dye at the 3' end. SEQ ID NOS. 48-51 include oligonucleotide primers used to generate DNA templates for in vitro transcription with T7 polymerase.

| SEQ ID NO. | Sequence | Description |
|---|---|---|
| 35 | 5'-FAM-CGCGAUGAUGCGCG-IABkFQ-3' | ssRNA Reporter (Variable region underlined); Trinucleotides: AUG, UGA, GAU; class: Structured |
| 36 | 5'-FAM-CGCGAUUAUUCGCG-IABkFQ-3' | ssRNA Reporter (Variable region underlined); Trinucleotides: AUU, UUA, UAU; class: Structured |
| 37 | 5'-FAM-AUAUCCCCCCAUAU-IABkFQ-3 | ssRNA Reporter (Variable region underlined); Trinucleotides: CCC; class: Structured |
| 38 | 5'-FAM-AUAUCCGCCGAUAU-IABkFQ-3' | ssRNA Reporter (Variable region underlined); Trinucleotides: CCG, CGC, GCC; class: Structured |
| 39 | 5'-FAM-AUAUCCUCCUAUAU-IABkFQ-3' | ssRNA Reporter (Variable region underlined); Trinucleotides: CCU, CUC, UCC; class: Structured |
| 40 | 5'-FAM-AUAUCGGCGGAUAU-IABkFQ-3' | ssRNA Reporter (Variable region underlined); Trinucleotides: CGG, GGC, GCG; class: Structured |
| 41 | 5'-FAM-AUAUCGUCGUAUAU-IABkFQ-3' | ssRNA Reporter (Variable region underlined); Trinucleotides: CGU, GUC, UCG; class: Structured |
| 42 | 5'-FAM-AUAUCUGCUGAUAU-IABkFQ-3' | ssRNA Reporter (Variable region underlined); Trinucleotides: CUG, UGC, GCU; class: Structured |
| 43 | 5'-FAM-CGCGCUUCUUCGCG-IABkFQ-3' | ssRNA Reporter (Variable region underlined); Trinucleotides: CUU, UUC, UCU; class: Structured |
| 44 | 5'-FAM-AUAUGGUGGUAUAU-IABkFQ-3' | ssRNA Reporter (Variable region underlined); Trinucleotides: GGU, GUG, UGG; class: Structured |
| 45 | 5'-FAM-CGCGGUUGUUCGCG-IABkFQ-3' | ssRNA Reporter (Variable region underlined); Trinucleotides: GUU, UUG, UGU; class: Structured |
| 46 | 5'-FAM-CGCGUUUUUCGCG-IABkFQ-3' | ssRNA Reporter (Variable region underlined); Trinucleotides: UUU; class: Structured |
| 47 | 5'-FAM-TGAACTGAACTGAACTGAACTG AACTGAACTAGTTCAGTTCAGT TCAGTTCAGTTCAGTTCA-BHQ-3' | dsDNA Reporter |
| 48 | GATAATACGACTCACTATAGGG AACTGATTACAAACATTGGCCG CAAATTGCACAATT | SARS-CoV-2 N1 T7 template Forward; Oligonucleotide primer used to generate DNA templates for in vitro transcription with T7 polymerase |
| 49 | GCGCGACATTCCGAAGAACGCT GAAGCGCTGGGGGCAAATTGTG CAATTTGCGGCC | SARS-CoV-2 N1 T7 template Reverse; Oligonucleotide primer used to generate DNA templates for in vitro transcription with T7 polymerase |
| 50 | GATAATACGACTCACTATAGGG AACTGATTACAAACATTGGCCG CAAATTGCACAATT | SARS-CoV-1 N1 T7 template Forward; Oligonucleotide primer used to generate DNA templates for in vitro transcription with T7 polymerase |

TABLE 1-continued

Sequence Listing. Fluorescent RNA and DNA reporters in which variable regions of sequence are underlined. All sequences each have 5-Carboxyfluorescein (FAM) dye at the 5' end. SEQ ID NOS. 1-46 each have Iowa Black FQ quencher (IABkFQ) at the 3' end. SEQ ID NO. 47 has Black Hole Quencher (BHQ) dye at the 3' end. SEQ ID NOS. 48-51 include oligonucleotide primers used to generate DNA templates for in vitro transcription with T7 polymerase.

| SEQ ID NO. | Sequence | Description |
|---|---|---|
| 51 | GCGTGACATTCCAAAGAATGCA GAGGCACTTGGAGCAAATTGTG CAATTTGCGGCC | SARS-CoV-1 N1 T7 template Reverse; Oligonucleotide primer used to generate DNA templates for in vitro transcription with T7 polymerase |

TABLE 2

RNase P RNA levels in nasopharyngeal swab samples and diluted total RNA from HEK 293T cells used as negative control.

| Sample | Ct value (RP primers, 2019-nCoV CDC EUA Kit, IDT#10006606) |
|---|---|
| RNA patient sample 1 | 26.85 |
| RNA patient sample 2 | 24.73 |
| RNA patient sample 3 | 35.41 |
| RNA patient sample 4 | 28.29 |
| RNA patient sample 5 | 28.58 |
| RNA patient sample 6 | 20.36 |
| RNA patient sample 7 | 25.24 |
| RNA patient sample 8 | 25.14 |
| RNA patient sample 9 | 28.15 |
| RNA patient sample 10 | 30.37 |
| Total RNA from HEK293T (diluted) | 23.35 |

TABLE 3

Examples of nuclease sequences.

| Nuclease | Organism | Accession | SEQ ID NO: Gene sequence, codon optimized for expression in *E. coli* | SEQ ID NO: Protein sequence |
|---|---|---|---|---|
| Amtb01NucC (TexNucC) | Acidimicrobiales bacterium mtb01 | NCBI: TEX45487.1 | SEQ ID NO.: 52 atgACACCAGCCAATGGAC TTGAGGCTTATTTCGCGGC TCTTCAAGACCGTTTGCAG GCGTCGATTAAAGTTGCAG CAGTATTGGATCACCCGGG TGCGAAAGGAGATGAGAC GGAGATTAGTTGGGAACG CCTGTTGGACGGTCACCTT CCCCGCCGCTACCAAGTTG TACCGAAGTGCATGTTTGT TGATCATACCGGGAAGTTA TCACAAGAAGTAGACTTG GCACTTTGTGATCGTCAAT ATAGCACTCTGGCTCTGGA ATCTCAGTCGCGTACAGTC GTCCCTGCGGAAGCGGCTT ACGCCGTGTTTGAGGTAAA ACCGGAACTTAACCGTGAA AATGTTTTATATGCTGCGG AAAAAGCTGCTTCCGTGCG CGTTTTAGCCCGCACGTCT GCACCGATTACGGATGCTC GTGGTGTTATTGAGGAGC CCCGCCGTCCGTCGCCGAT TATTGCGGGACTTCTTACG ACGCGTGCAGGTTGGTCTC CTACTTTGGGCGATGCCTT CTCGGCGGCGCTTAAAGAT CAGAACAGCAATGGATTA CTGAACTTGGGCTGTGTAC TGGGAGAGATCGGCTGGG AGGTGAAATATGAAAACA ACATCCCACGCTGGGCCGC CTCGACTCCCAGTCGCGCG | SEQ ID NO.: 53 MTPANGLEAYFAALQD RLQASIKVAAVLDHPGA KGDETEISWERLLDGHL PRRYQVVPKCMFVDHT GKLSQEVDLALCDRQYS TLALESQSRTVVPAEAA YAVFEVKPELNRENVLY AAEKAASVRVLARTSAP ITDARGVIEEPRRPSPIIA GLLTTRAGWSPTLGDA FSAALKDQNSNGLLNLG CVLGEIGWEVKYENNIP RWAASTPSRALVFFYLR LLSALQRVGTVPAMDY DQWSAFLSHD |

TABLE 3-continued

Examples of nuclease sequences.

| Nuclease | Organism | Accession | SEQ ID NO: Gene sequence, codon optimized for expression in E. coli | SEQ ID NO: Protein sequence |
|---|---|---|---|---|
| | | | CTGGTGTTTTTTATTTGCG TCTGCTGTCCGCTCTTCAG CGTGTGGGCACAGTACCC GCTATGGACTACGACCAAT GGTCAGCATTTTTATCGCA TGACTGA | |
| CtNucC | Clostridium tepidum | NCBI: WP_195923598.1 | SEQ ID NO.: 54 atgAAATCCACAGGACGTC GTCTTTTTGGCAAGCAAGG GGGGTCGGACATGGGTCA GATTGATATCAAGAGCTTG TTCTATAGCCTTCAAACGC AGATGTGTGCAAAATTATC TACCAACCGTCAGCACATC CAACACCCTGGGATTAAAG GGGACTCATCCGAGTTGA ATTGGATTGAGTGGCTTAA AACGTACCTGCCTAAACGC TACAGTGTCGATAAAGCAT TTATCATTGATTGTGACGG AAATATGTCTGACCAAATC GACGTAGTAATCTACGATC AACAGTATTCGCCCTTCGT TTTCAACCAGGATAACGCC TATTATATCCCAGCCGAGT CGGTGTACGCTATTTTCGA AGTTAAGCAAGAAATCAA CAAAGAGAACATTATCTAC GCCGGTGATAAGACCAAG TCGGTCCGCAGTCTGAAAC GCACTTCCACGGCCATTCC TCACGCAGGAGGTTACTAT GCGCCTAAACCGCACAACA AAATCCTGAGCGGCATCTT AACTTTATCGAGCGTATGG AATCCGCCTTTAGGCAAGT CATTTGAAGAAGCTATCTA CTCTTTAGAAGATGAGTCA AAGTTAGATATCGGCTGTA TCTTAGCTGAAGGGTCATT CCTTGCAGATTATAAGAAT GATGTTCTGATGAAATCGA CCGAAGAAGAATCCTTGAT TTTTTTCTTTCTGAAATTAC TGATCGAGTTACAATCTCT GGGGACCACTCCGGCAAT TGATATTAATTGCTACGGT CGCGCCCTGGATTCAATTT AA | SEQ ID NO.: 55 MGQIDIKSLFYSLQTQM CAKLSTNRQHIQHPGIK GDSSELNWIEWLKTYLP KRYSVDKAFIIDCDGNM SDQIDVVIYDQQYSPFV FNQDNAYYIPAESVYAI FEVKQEINKENIIYAGDK TKSVRSLKRTSTAIPHAG GYYAPKPHNKILSGILTL SSVWNPPLGKSFEEAIY SLEDESKLDIGCILAEGSF LADYKNDVLMKSTEEES LIFFFLKLLIELQSLGTTP AIDINCYGRALDSI |
| EsNucC | Elioraea sp. | NCBI: WP_141855040.1 | SEQ ID NO.: 56 atgAGTGGTTTCAGTTTACC AAAGTTGCTGGCGGGGCT GCACGACACCATTGAACAT CGCCTTAAGCTGGCCCGTG AAACGATGGGACATCCGG TTAACAAAGGCGATGCTTC TGAGGCAGTATGGCTGGA TCTGTTACAAACGTATCTG CCCCGTCGCTACAAAGCGG CCAAGGCGCATGTAGTTG ATAGTACCGGGGCATTCTC CGAGCAGATTGATGTAGTC GTTTTCGATCGCCAGTACA GCCCATTGGTTTTCCAACA TGAGGGGCAAACAATCAT TCCAGCCGAAAGTGTATAT GCAGTCTTTGAGGCTAAGC AGAGTATTGCTGCACCTGA GATCACTTACGCACACCGC AAGGTAGCGAGCGTGCGC CGCTTGCATCGCACGAGCC | SEQ ID NO.: 57 MSGFSLPKLLAGLHDTI EHRLKLARETMGHPVN KGDASEAVWLDLLQTY LPRRYKAAKAHVVDST GAFSEQIDVVVFDRQYS PLVFQHEGQTIIPAESVY AVFEAKQSIAAPEITYAH RKVASVRRLHRTSLPIPH AGGTYPPKPLSRILAGLL TLESAWNPPLGQTLIDN LCAGDDDSRLDLGCVA AHGVFACDQAGVYWIR PQGKAATAFLFELIARL QETATVSMIDIRAYAR WLTAAPEQPST |

TABLE 3-continued

Examples of nuclease sequences.

| Nuclease | Organism | Accession | SEQ ID NO: Gene sequence, codon optimized for expression in E. coli | SEQ ID NO: Protein sequence |
|---|---|---|---|---|
| | | | TTCCGATCCCACATGCAGG CGGAACATATCCTCCGAAG CCGTTATCGCGTATCTTGG CAGGATTATTAACGTTGGA GTCGGCATGGAACCCGCC GCTTGGGCAAACGCTTATT GACAACTTGTGTGCCGGC GACGACGATTCCCGTCTTG ACTTAGGATGTGTTGCAGC ACATGGCGTCTTTGCCTGT GACCAGGCGGGTGTATAT TGGATTCGTCCGCAAGGG AAGGCGGCGACAGCATTC TTATTCGAGTTAATCGCCC GTTTGCAGGAGACGGCTA CCGTCTCGATGATCGACAT TCGCGCGTACGCTCGCTGG TTAACCGCTGCCCCAGAAC AGCCTTCCACCTGA | |
| AaCan2 | Archaeoglobi archaeon JdFR-42 | JGI: 2730024700 | SEQ ID NO.: 58 ATGAGTCACATTCATGTCT GTCTTGTATCTGACCAAGC AATTCCAAATCTGACAACA GCTCTTCAATTTAACCCCG ATACTACGGTGTTATATC CACAAACGAAATGAAGGA CAAAGCCAAACGTTTGGA AACCGTATTGAAGAACAA AGGTTTAAAGGTAAAAAC CTTGAAGATCTCGGCGTAT GACATCAACGACGTGATTA CAGTTTCGGAATCCTTGTT GAATGATTGTAAAGGCTG CAAAGTGTCCCTTAACATT ACAGGGGGCACTAAGATT GGGACGCTTGGTACCTTCC AGGTCTTTTACACTGCGAG CAAACCGATTTTTTATGTC AACACGAAGGACAACGAG ATCATTAAACTGTATCCCG AGAAAGAACAGCAGAAGT ACCCGATTGAGATTAGCAT TTCAATCAAGGACTATTTG GCAGTGTACGGATTCAAC GTTAAGAGTTATGTCAAGG ACGACTCCTACATCTACAA ACGTAAGAAGGTAACTGA CTATCTTGCAAATCTGGTA ATCCATCGTCCCAATATCA TCGGTGAAATCAACTATAA GTTACAAAATTTTGAAGAA AAGTCCTATCCTCTGAAGA TTAACATCACTAAAAATAA GCAGGTCATTAAGCTTTAT GATATTTTAAAGGATTCCG GCCTTGTTAAAATCCGCAA TAAAAGTACGATCGAAATC CCAGATGTTGAGACTGCAA AGTATTTGAATGGCATTTG GTTCGAGGAATATGTTTAT ATGATGGCTAAGTCCCTTG GCGCCGATGAAGTGAAAT TGAATGTGAAAGGGGTAT GGGACACAGTCGGAAAGC ATCCGCCGACTAACGAGTT TGATATTTTGATTAGCAAG GGTAACCGTTTATTTTATA TCAGTTGTAAGACTGCGAA TCCGGATCGTAAGATTGAT GATACGGATGAGACAATC GGGAAGGAATACCTGTAC GAACTTGACTCAATTAGCG | SEQ ID NO.: 59 MSHIHVCLVSDQAIPNL TTALQFNPDTTVLLSTN EMKDKAKRLETVLKNK GLKVKTLKISAYDINDVI TVSESLLNDCKGCKVSL NITGGTKIGTLGTFQVFY TASKPIFYVNTKDNEIIKL YPEKEQQKYPIEISISIKD YLAVYGFNVKSYVKDDS YIYKRKKVTDYLANLVIH RPNIIGEINYKLQNFEEK SYPLKINITKNKQVIKLY DILKDSGLVKIRNKSTIEI PDVETAKYLNGIWFEEY VYMMAKSLGADEVKLN VKGVWDTVGKHPPTN EFDILISKGNRLFYISCKT ANPDRKIDDTDETIGKE YLYELDSISDSALGLFGK RMLASARAIKNDYVRK RAEILKIDIADGQNIATL KGKLQQWLSK |

TABLE 3-continued

Examples of nuclease sequences.

| Nuclease | Organism | Accession | SEQ ID NO: Gene sequence, codon optimized for expression in E. coli | SEQ ID NO: Protein sequence |
|---|---|---|---|---|
| | | | ATTCAGCGTTGGGGCTTTT<br>TGGTAAACGTATGCTGGCT<br>TCAGCCCGCGCGATTAAGA<br>ATGACTACGTCCGTAAGCG<br>TGCAGAGATCCTGAAGATC<br>GACATTGCCGACGGCCAA<br>AACATCGCCACTCTGAAGG<br>GGAAACTTCAACAGTGGCT<br>TTCGAAATGA | |
| TthCan1 | Thermus thermophilus | NCBI: WP_011229147.1 | SEQ ID NO.: 60<br>ATGCAAGCCCCGGTGTATC<br>TGTGCTTGCTGGGAAACG<br>ACCCAGCTCCTGCCTACCT<br>GGGTCTGAAGGTTGTGGA<br>ACGTGAGGCTGGCCGCGT<br>GGCGAAGGCCGTGTTCTAT<br>TCCTTTCCCGCATGGAATG<br>AGGAATATGGGAAGAAAC<br>GCCAGGCTTTCTTCCGTTT<br>ATTGTCGGAGAAGGGGGT<br>GTTATATGAGGAACGTCCT<br>TTGGAGAAAGGTCTTGAA<br>GAGGCGGAGGCCCGTGAA<br>GTCTGGGTTAATCTTACGG<br>GTGGGGCTAAGTATTGGG<br>CGGTCCGCTTTTTGGGTCA<br>CTGGCGCCGTCCTGGTGC<br>GCGTGTATTCTTGGTCGAA<br>GGCCACCGCGCTCTGGAG<br>GCACCGCGTGCGCTTTTCC<br>TTTGGCCGCGCGAAGAGG<br>AGCGCTCATTGGAGGCGG<br>AAGCGCTTACTCTTGAAGA<br>GTATGCCCGCTTATATCTT<br>GAGCCCTTGGGCGAAGCC<br>TGGGAGCGTGTCTCTCCGC<br>CAGGAGCTTTTCCGCCCGG<br>AGCGCAGGCTGCGCGTCTT<br>CCGGGCCGCGAGGGCGGT<br>GTTTTCGTTGTACACCGCG<br>GCCTGCCGTACTGGTATTG<br>GGTGCGTCCTCACTTGGGC<br>GGCGAAGCAAAAGACATG<br>TCCCGTAAAGCTCTGAGTG<br>CTTTCAGCGGTGAGGCGA<br>AGCGCCTGGGGGGACAGT<br>TATGTCTTCCTGTCGTTCCC<br>TATCACAAAGCGCATTTGC<br>GCTCCCGCCACCCGAAGG<br>AACGTGAAAATGTTTTTGC<br>TCGCTGGCGTGCATGGGC<br>GCGTGAATACGGGGTATTT<br>TTAGTAGATCCAGGGCGTC<br>CCCTGGAGGAAGAAGTCG<br>CGTCCCTGATCAAGGGTAA<br>AGCCTCCAAGAAAGCTTTG<br>CCGCTGCCCCAGGAAGGT<br>CCGCTGTTACTTGCGCTGG<br>TGTCGGAGCAAGCCGTGC<br>CCCTTTATGCCGCCTATCT<br>GCACGCAGGACCTCGTGA<br>AGTCTATCTGTTGACGACA<br>CCCGAAATGGAATCACGTC<br>TGCGTTGGGCCGAAGCCTT<br>CTTCCGTGGAAAGGGTGT<br>ACGTGTCCATCGTTCTTTCC<br>TTTCCGGTCCTTGGGCGTT<br>GCGCGAGGTCCGTGACTT<br>GTTGGCACCGGTGGTAGA<br>AGAAGCGTTGCGTCGTGG<br>CCATCCAGTACACGCCAAT<br>CTTAACAGTGGAACAACTG | SEQ ID NO.: 61<br>MQAPVYLCLLGNDPAP<br>AYLGLKVVEREAGRVAK<br>AVFYSFPAWNEEYGKK<br>RQAFFRLLSEKGVLYEER<br>PLEKGLEEAEAREVWV<br>NLTGGAKYWAVRFLGH<br>WRRPGARVFLVEGHRA<br>LEAPRALFLWPREEERS<br>LEAEALTEEYARLYLEPL<br>GEAWERVSPPGAFPPG<br>AQAARLPGREGGVFVV<br>HRGLPYWYWVRPHLG<br>GEAKDMSRKALSAFSG<br>EAKRLGGQLCLPVVPYH<br>KAHLRSRHPKERENVFA<br>RWRAWAREYGVFLVD<br>PGRPLEEEVASLIKGKAS<br>KKALPLPQEGPLLLALVS<br>EQAVPLYAAYLHAGPRE<br>VYLLTTPEMESRLRWAE<br>AFFRGKGVRVHRSFLSG<br>PWALREVRDLLAPVVEE<br>ALRRGHPVHANLNSGT<br>TAMALGLYLALRDGAR<br>AHYLDGDRLLLLDGGEA<br>EVPWEEGRPEDLLALR<br>GYRFEEEYPDARPDPGL<br>LALAEEILRRWDEVQTS<br>WEASPLVRRFLKFWKK<br>RFGQAFPPKRLSRLKGL<br>PLEYAVYSHLNAHLAPK<br>GGQARMGGHLVPLGG<br>NEALAPQSTEVDGVFF<br>HRGALWFVECKPTDEG<br>LRERAPIMAELVRSVGG<br>VEARGLMVARRWRGA<br>PPPASPNLVYMALEGG<br>EGVGVYRFPEELEKALS<br>RNPAPRRG |

TABLE 3-continued

Examples of nuclease sequences.

| Nuclease | Organism | Accession | SEQ ID NO: Gene sequence, codon optimized for expression in E. coli | SEQ ID NO: Protein sequence |
|---|---|---|---|---|
| | | | CAATGGCCTTGGGCCTGTA<br>TCTGGCATTACGTGATGGA<br>GCCCGCGCGCATTATCTGG<br>ATGGAGATCGTTTATTGCT<br>TTTAGACGGGGAGAGGC<br>GGAGGTCCCATGGAAGA<br>GGGCCGCCCAGAGGATCT<br>TCTTGCTCTGCGTGGTTAC<br>CGTTTTGAGGAGGAATATC<br>CCGACGCTCGCCCCGATCC<br>TGGCTTATTGGCGCTGGCA<br>GAGGAGATCTTACGTCGCT<br>GGGATGAGGTTCAAACTA<br>GTTGGGAGGCTTCTCCACT<br>GGTTCGTCGTTTTCTTAAG<br>TTCTGGAAAAAACGTTTTG<br>GACAAGCGTTTCCCCCGAA<br>GCGTTTAAGCCGCCTGAAG<br>GGGTTACCGTTGGAATATG<br>CAGTGTACTCTCATTTAAA<br>TGCACATTTAGCTCCCAAG<br>GGCGGCCAGGCTCGTATG<br>GGCGGACACCTTGTACCTT<br>TGGGTGGGAATGAAGCCC<br>TTGCTCCCCAATCGACTGA<br>AGTAGATGGCGTCTTCTTT<br>CACCGCGGCGCGTTATGGT<br>TCGTCGAGTGCAAGCCCAC<br>GGATGAAGGACTTCGTGA<br>GCGTGCTCCGATCATGGCG<br>GAGTTGGTCCGTAGCGTA<br>GGCGGCGTTGAAGCTCGC<br>GGTTTAATGGTCGCACGCC<br>GTTGGCGCGGGCACCCC<br>CTCCTGCCTCTCCAAACTTA<br>GTTTATATGGCACTGGAAG<br>GCGGAGAAGGAGTAGGG<br>GTATACCGCTTCCCAGAAG<br>AATTAGAGAAAGCACTTTC<br>TCGTAATCCTGCACCACGC<br>CGTGGGTAA | |

REFERENCE LISTING

1. Drain, P. K. Rapid Diagnostic Testing for SARS-CoV-2. https://doi.org/10.1056/NEJMcp2117115 (2022) doi: 10.1056/NEJMCP2117115.
2. Allan-Blitz, L. T. & Klausner, J. D. A Real-World Comparison of SARS-CoV-2 Rapid Antigen Testing versus PCR Testing in Florida. Journal of Clinical Microbiology 59, (2021).
3. Jessica L. Prince-Guerra, P. O. A. et al. Evaluation of Abbott BinaxNOW Rapid Antigen Test for SARS-CoV-2 Infection at Two Community-Based Testing Sites—Pima County, Arizona, Nov. 3-17, 2020. https://www.cdc.gov/mmwr/volumes/70/wr/pdfs/mm7003e3-H.pdf.
4. Kaminski, M. M., Abudayyeh, O. O., Gootenberg, J. S., Zhang, F. & Collins, J. J. CRISPR-based diagnostics. Nature Biomedical Engineering 2021 5:7 5, 643-656 (2021).
5. Abudayyeh, O. O. & Gootenberg, J. S. CRISPR diagnostics. Science 372, 914-915 (2021).
6. Pardee, K. et al. Rapid, Low-Cost Detection of Zika Virus Using Programmable Biomolecular Components. Cell 165, 1255-1266 (2016).
7. Jiao, C. et al. Noncanonical crRNAs derived from host transcripts enable multiplexable RNA detection by Cas9. Science 372, 941-948 (2021).
8. Gootenberg, J. S. et al. Nucleic acid detection with CRISPR-Cas13a/C2c2. Science 356, 438-442 (2017).
9. Chen, J. S. et al. CRISPR-Cas12a target binding unleashes indiscriminate single-stranded DNase activity. Science (New York, N.Y.) 360, 436 (2018).
10. Kazlauskiene, M., Kostiuk, G., Venclovas, a., Tamulaitis, G. & Siksnys, V. A cyclic oligonucleotide signaling pathway in type III CRISPR-Cas systems. Science 357, 605-609 (2017).
11. Kazlauskiene, M., Tamulaitis, G., Kostiuk, G., Venclovas, C. & Siksnys, V. Spatiotemporal Control of Type III-A CRISPR-Cas Immunity: Coupling DNA Degradation with the Target RNA Recognition. Molecular cell 62, 295-306 (2016).
12. Niewoehner, O. et al. Type III CRISPR-Cas systems produce cyclic oligoadenylate second messengers. Nature 2017 548:7669 548, 543-548 (2017).
13. Athukoralage, J. S. et al. The dynamic interplay of host and viral enzymes in type iii crispr-mediated cyclic nucleotide signalling. eLife 9, (2020).
14. Makarova, K. S. et al. Evolutionary and functional classification of the CARF domain superfamily, key sensors in prokaryotic antivirus defense. Nucleic Acids Research 48, 8828-8847 (2020).
15. Rostol, J. T. & Marraffini, L. A. Non-specific degradation of transcripts promotes plasmid clearance during type III-A CRISPR-Cas immunity. Nature Microbiology 2019 4:4 4, 656-662 (2019).
16. Santiago-Frangos, A. et al. Intrinsic signal amplification by type III CRISPR-Cas systems provides a sequence-specific SARS-CoV-2 diagnostic. Cell Reports Medicine 2, 100319 (2021).
17. Steens, J. A. et al. SCOPE enables type III CRISPR-Cas diagnostics using flexible targeting and stringent CARF ribonuclease activation. Nature Communications 2021 12:1 12, 1-12 (2021).
18. Sridhara, S., Goswami, H. N., Whyms, C., Dennis, J. H. & Li, H. Virus detection via programmable Type III-A CRISPR-Cas systems. doi:10.1038/s41467-021-25977-7.
19. Smalakyte, D. et al. Type III-A CRISPR-associated protein Csm6 degrades cyclic hexa-adenylate activator using both CARF and HEPN domains. Nucleic Acids Research 48, 9204-9217 (2020).
20. Athukoralage, J. S., Graham, S., Grüschow, S., Rouillon, C. & White, M. F. A Type III CRISPR Ancillary Ribonuclease Degrades Its Cyclic Oligoadenylate Activator. Journal of Molecular Biology 431, 2894-2899 (2019).
21. Athukoralage, J. S., Rouillon, C., Graham, S., Grüschow, S. & White, M. F. Ring nucleases deactivate type III CRISPR ribonucleases by degrading cyclic oligoadenylate. Nature 2018 562:7726 562, 277-280 (2018).
22. Garcia-Doval, C. et al. Activation and self-inactivation mechanisms of the cyclic oligoadenylate-dependent CRISPR ribonuclease Csm6. Nature Communications 2020 11:1 11, 1-9 (2020).
23. Jia, N., Jones, R., Yang, G., Ouerfelli, O. & Patel, D. J. CRISPR-Cas III-A Csm6 CARF Domain Is a Ring Nuclease Triggering Stepwise cA4 Cleavage with ApA>p Formation Terminating RNase Activity. Molecular Cell 75, 944-956.e6 (2019).
24. Grüschow, S., Grüschow, G., Adamson, C. S. & White, M. F. Specificity and sensitivity of an RNA targeting type III CRISPR complex coupled with a NucC endonuclease effector. Nucleic Acids Research (2021) doi:10.1093/NAR/GKAB 1190.
25. Hale, C. R. et al. RNA-Guided RNA Cleavage by a CRISPR RNA-Cas Protein Complex. Cell 139, 945-956 (2009).
26. Rouillon, C., Athukoralage, J. S., Graham, S., Grüschow, S. & White, M. F. Control of cyclic oligoadenylate synthesis in a type III CRISPR system. eLife 7, (2018).
27. Molina, R. et al. Structure of Csx1-cOA4 complex reveals the basis of RNA decay in Type III-B CRISPR-Cas. Nature Communications 2019 10:1 10, 1-14 (2019).
28. Liu, T. Y. et al. Accelerated RNA detection using tandem CRISPR nucleases. Nature Chemical Biology 2021 17:9 17, 982-988 (2021).
29. Rostol, J. T. et al. The Card1 nuclease provides defence during type III CRISPR immunity. Nature 2021 590:7847 590, 624-629 (2021).
30. Zhu, W. et al. The CRISPR ancillary effector Can2 is a dual-specificity nuclease potentiating type III CRISPR defence. Nucleic Acids Research 49, 2777-2789 (2021).
31. McMahon, S. A. et al. Structure and mechanism of a Type III CRISPR defence DNA nuclease activated by cyclic oligoadenylate. Nature Communications 2020 11:1 11, 1-11 (2020).
32. Ye, Q. et al. HORMA Domain Proteins and a Trip13-like ATPase Regulate Bacterial cGAS-like Enzymes to Mediate Bacteriophage Immunity. Molecular Cell 77, 709-722.e7 (2020).
33. Lau, R. K. et al. Structure and Mechanism of a Cyclic Trinucleotide-Activated Bacterial Endonuclease Mediating Bacteriophage Immunity. Molecular Cell 77, 723-733.e6 (2020).
34. Batéjat, C., Grassin, Q., Manuguerra, J.-C. & Leclercq, I. Heat inactivation of the severe acute respiratory syndrome coronavirus 2. Journal of Biosafety and Biosecurity 3, 1 (2021).
35. Liu, T. Y., Iavarone, A. T. & Doudna, J. A. RNA and DNA Targeting by a Reconstituted Thermus thermophilus Type III-A CRISPR-Cas System. PLOS ONE 12, e0170552 (2017).
36. Lee, J. et al. CRISPR-Cap: multiplexed double-stranded DNA enrichment based on the CRISPR system. Nucleic acids research 47, (2019).
37. Schultzhaus, Z., Wang, Z. & Stenger, D. CRISPR-based enrichment strategies for targeted sequencing. Biotechnology Advances 46, 107672 (2021).
38. Lee, J. et al. CRISPR-Cap: multiplexed double-stranded DNA enrichment based on the CRISPR system. Nucleic Acids Research 47, el-el (2019).
39. O'Connell, M. R. et al. Programmable RNA recognition and cleavage by CRISPR/Cas9. Nature 516, 263 (2014).
40. East-Seletsky, A. et al. Two distinct RNase activities of CRISPR-C2c2 enable guide-RNA processing and RNA detection. Nature 2016 538:7624 538, 270-273 (2016).
41. Liu, L. et al. The Molecular Architecture for RNA-Guided RNA Cleavage by Cas13a. Cell 170, 714-726.e10 (2017).
42. Jia, N., Jones, R., Sukenick, G. & Patel, D. J. Second Messenger cA4 Formation within the Composite Csm1 Palm Pocket of Type III-A CRISPR-Cas Csm Complex and Its Release Path. Molecular Cell 75, 933-943.e6 (2019).
43. Lowey, B. et al. CBASS Immunity Uses CARF-Related Effectors to Sense 3 0-5 0- and 2 0-5 0-Linked Cyclic Oligonucleotide Signals and Protect Bacteria from Phage Infection In Brief. Cell 182, 38-49 (2020).
44. Jiang, W., Samai, P. & Marraffini, L. A. Degradation of Phage Transcripts by CRISPR-Associated RNases Enables Type III CRISPR-Cas Immunity. Cell 164, 710-721 (2016).
45. Larremore, D. B. et al. Test sensitivity is secondary to frequency and turnaround time for COVID-19 screening. Science Advances 7, (2021).
46. Gootenberg, J. S. et al. Multiplexed and portable nucleic acid detection platform with Cas13, Cas12a and Csm6. Science 360, 439-444 (2018).
47. Jain, M. et al. Nanopore sequencing and assembly of a human genome with ultra-long reads. Nature Biotechnology 2018 36:4 36, 338-345 (2018).
48. Li, W. & Godzik, A. Cd-hit: a fast program for clustering and comparing large sets of protein or nucleotide sequences. Bioinformatics 22, 1658-1659 (2006).
49. Katoh, K. & Standley, D. M. MAFFT Multiple Sequence Alignment Software Version 7: Improvements in Performance and Usability. Molecular Biology and Evolution 30, 772— 780 (2013).
50. Gouveia-Oliveira, R., Sackett, P. W. & Pedersen, A. G. MaxAlign: Maximizing usable data in an alignment. BMC Bioinformatics 8, 1-8 (2007).

51. Finn, R. D., Clements, J. & Eddy, S. R. HMMER web server: interactive sequence similarity searching. Nucleic Acids Research 39, W29—W37 (2011).
52. Capella-Gutiérrez, S., Silla-Martinez, J. M. & Gabaldón, T. trimAl: a tool for automated alignment trimming in large-scale phylogenetic analyses. Bioinformatics 25, 1972-1973 (2009).
53. Darriba, D., Taboada, G. L., Doallo, R. & Posada, D. ProtTest 3: fast selection of best-fit models of protein evolution. Bioinformatics 27, 1164-1165 (2011).
54. Minh, B. Q. et al. IQ-TREE 2: New Models and Efficient Methods for Phylogenetic Inference in the Genomic Era. Molecular Biology and Evolution 37, 1530-1534 (2020).
55. Yu, G., Lam, T. T. Y., Zhu, H. & Guan, Y. Two Methods for Mapping and Visualizing Associated Data on Phylogeny Using Ggtree. Molecular Biology and Evolution 35, 3041-3043 (2018).
56. Price, M. N., Dehal, P. S. & Arkin, A. P. FastTree 2— Approximately Maximum-Likelihood Trees for Large Alignments. PLOS ONE 5, e9490 (2010).
57. Steens, J. A. et al. SCOPE enables type III CRISPR-Cas diagnostics using flexible targeting and stringent CARF ribonuclease activation. Nat. Commun. 12, 1-12 (2021).
58. Santiago-Frangos, A. et al. Intrinsic signal amplification by type III CRISPR-Cas systems provides a sequence-specific SARS-CoV-2 diagnostic. Cell Rep. Med. 2, 100319 (2021).
59. Grüschow, S., Adamson, C. S. & White, M. F. Specificity and sensitivity of an RNA targeting type III CRISPR complex coupled with a NucC endonuclease effector. Nucleic Acids Res. 49, 13122-13134 (2021).
60. Sridhara, S., Goswami, H. N., Whyms, C., Dennis, J. H. & Li, H. Virus detection via programmable Type III-A CRISPR-Cas systems. Nat. Commun. 12, 1-10 (2021).
61. Foster, K., Grüschow, S., Bailey, S., White, M. F. & Terns, M. P. Regulation of the RNA and DNA nuclease activities required for *Pyrococcus furiosus* Type III-B CRISPR—Cas immunity. Nucleic Acids Res. 48, 4418-4434 (2020).
62. Grüschow, S., Adamson, C. S. & White, M. F. Specificity and sensitivity of an RNA targeting type III CRISPR complex coupled with a NucC endonuclease effector. Nucleic Acids Res. 49, 13122-13134 (2021).
63. Bailey, T. L. & Elkan, C. Fitting a mixture model by expectation maximization to discover motifs in biopolymers. Proc. Int. Conf. Intell. Syst. Mol. Biol. 2, 28-36 (1994).
64. Santiago-Frangos, A. et al. Intrinsic signal amplification by type III CRISPR-Cas systems provides a sequence-specific SARS-CoV-2 diagnostic. Cell Rep. Med. 2, 100319 (2021).

Target nucleic acid such as RNA and/or DNA may be obtained from a subject. For example, target RNA may be an RNA of an organism that infects a host organism. In particular, the target RNA may be an RNA genome of a virus that has infected the subject. In another example, the target RNA may be the RNA of the subject. A subject may refer to an animal, such as a mammalian species (preferably human) or avian (e.g., bird) species, or other organism, such as a plant. More specifically, a subject can be a vertebrate, e.g., a mammal such as a mouse, a primate, a simian or a human. Animals include farm animals, sport animals, and pets. A subject can be a healthy individual, an individual that has symptoms or signs or is suspected of having a disease or a predisposition to the disease, or an individual that is in need of therapy or suspected of needing therapy.

A genetic modification or mutation in the context of an engineered system may refer to an alteration, variant or polymorphism in a nucleic acid that may result in altered or disabled functionality of a corresponding protein. Such alteration, variant or polymorphism can be with respect to a reference genome, the subject or other individual. Variations include one or more single nucleotide variations (SNVs), insertions, deletions, repeats, small insertions, small deletions, small repeats, structural variant junctions, variable length tandem repeats, and/or flanking sequences, CNVs, transversions, gene fusions and other rearrangements may also be considered forms of genetic variation. A variation can be a base change, insertion, deletion, repeat, copy number variation, transversion, or a combination thereof.

A "polynucleotide", "nucleic acid", "nucleic acid molecule", or "oligonucleotide" may each refer to a polymer of nucleosides (including deoxyribonucleosides, ribonucleosides, or analogs thereof) joined by inter-nucleosidic linkages. Typically, a polynucleotide comprises at least three nucleosides. Oligonucleotides often range in size from a few monomeric units, e.g. 3-4, to hundreds of monomeric units. Whenever a polynucleotide is represented by a sequence of letters, such as "AUGCCUG," it will be understood that the nucleotides are in 5' to 3' order from left to right and that "A" denotes adenosine, "C" denotes cytidine, "G" denotes guanosine, and "U" denotes uracil, unless otherwise noted. The letters A, C, G, and U (or "T" denoting thymine in DNA) may be used to refer to the bases themselves, to nucleosides, or to nucleotides comprising the bases, as is standard in the art.

All patent filings, websites, other publications, sequence listings, accession numbers and the like cited above or below are incorporated by reference in their entirety for all purposes to the same extent as if each individual item were specifically and individually indicated to be so incorporated by reference.

If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the disclosure can be used in combination with any other unless specifically indicated otherwise. Although the present disclosure has been described in some detail by way of illustration and example for purposes of clarity and understanding, it will be apparent that certain changes and modifications may be practiced within the scope of the appended claims.

What is claimed is:

1. A method of programmatically capturing and detecting target nucleic acid in a sample based on an engineered type III Clustered Regularly Interspaced Short Palindromic Repeat (CRISPR) complex, the method comprising:
   capturing the target nucleic acid in the sample using the engineered type III CRISPR-Cas complex, the engineered type III CRISPR-Cas complex comprising: a CRISPR guide comprising a CRISPR guide sequence engineered to be complementary to the target nucleic acid;
   concentrating the captured target nucleic acid to amplify detectable activity of the engineered type III CRISPR-Cas complex; and
   detecting the captured and concentrated target nucleic acid based on the detectable activity of the engineered type III CRISPR-Cas complex.

2. The method of claim 1, wherein the sample comprises a complex mixture and wherein the capturing and concentrating are performed without prior amplification of the target nucleic acid in the complex mixture.

3. The method of claim 1, wherein the detectable activity comprises generation of a linear or cyclic oligonucleotide.

4. The method of claim 3, wherein the generation of the linear or cyclic oligonucleotide is detectable via a nuclease that is activated by the linear or cyclic oligonucleotide.

5. The method of claim 4, wherein the nuclease comprises a Can nuclease and wherein the type III CRISPR system comprises the Can nuclease.

6. The method of claim 5, wherein the Can nuclease comprises Can1 and/or Can2.

7. The method of claim 4, wherein the nuclease comprises a NucC nuclease and wherein the type III CRISPR system comprises the NucC nuclease.

8. The method of claim 7, wherein contacting the nucleic acid in the sample with the engineered type III CRISPR-Cas complex comprises:
contacting the captured and concentrated nucleic acid with a fluorophore and a quencher tethered together by a nucleic acid tether, wherein the activated nuclease cleaves the nucleic acid tether to thereby release the fluorophore from the quencher; and
detecting a level of fluorescence of the released fluorophore.

9. The method of claim 8, wherein the tether comprises a ribonucleic acid and/or a deoxyribonucleic acid tether.

10. The method of claim 1, wherein the engineered type III CRISPR complex is Histidine-tagged (His-tagged), and wherein capturing the target nucleic acid comprises:
incubating the sample with the His-tagged engineered type III CRISPR complex to bind the His-tagged engineered type III CRISPR complex with the target nucleic acid; and
binding the His-tagged engineered type III CRISPR complex with bound target nucleic acid to magnetic particles.

11. The method of claim 10, wherein the magnetic particles comprise Ni-NTA beads.

12. The method of claim 10, wherein concentrating the captured target nucleic acid comprises:
applying a magnet to generate a pellet comprising the His-tagged engineered type III CRISPR complex bound to the target nucleic acid and the magnetic particles.

13. The method of claim 12, wherein the detectable activity comprises generation of a linear or cyclic oligonucleotide that is detectable via a nuclease activated by the linear or cyclic oligonucleotide, the method further comprising:
resuspending the pellet in a solution comprising reaction buffer containing ATP to activate polymerase activity of the His-tagged engineered type III CRISPR complex, wherein the polymerase activity generates the linear or cyclic oligonucleotide that activates the nuclease.

14. The method of claim 13, further comprising:
adding the nuclease, a fluorophore, and a quencher tethered together by a nucleic acid tether, wherein the activated nuclease cleaves the nucleic acid tether to release the fluorophore; and
detecting a level of fluorescence of the released fluorophore.

15. The method of claim 14, wherein the linear or cyclic oligonucleotide comprises cA3 and/or cA4 that activates a NucC nuclease.

16. The method of claim 14, wherein the linear or cyclic oligonucleotide comprises cA3 and/or cA4 that activates Can nuclease.

17. The method of claim 1, wherein the sample is a complex mixture obtained from a subject.

18. The method of claim 17, wherein the sample comprises a nasopharyngeal swab sample.

19. The method of claim 1, wherein the target nucleic acid in the sample comprises ribonucleic acid (RNA).

20. The method of claim 19, wherein the RNA comprises at least a portion of an RNA genome of a virus.

21. The method of claim 20, wherein the viral RNA comprises an RNA from the genome of severe acute respiratory syndrome coronavirus 2 (SARS-CoV-2).

22. The method of claim 1, wherein the CRISPR guide further comprises a 3' protospacer flanking sequence that activates or enhances generation of linear or cyclic oligonucleotides.

* * * * *